(12) United States Patent
Binmoeller et al.

(10) Patent No.: US 9,060,835 B2
(45) Date of Patent: *Jun. 23, 2015

(54) CONFORMATIONALLY-STABILIZED INTRALUMINAL DEVICE FOR MEDICAL APPLICATIONS

(75) Inventors: Kenneth F. Binmoeller, Rancho Santa Fe, CA (US); James T. McKinley, Redwood City, CA (US); Matthew Yurek, San Diego, CA (US); Fiona M. Sander, Los Altos Hills, CA (US)

(73) Assignee: Endosphere, Inc., Columbus, OH (US)

( * ) Notice: Subject to any disclaimer, the term of this patent is extended or adjusted under 35 U.S.C. 154(b) by 276 days.

This patent is subject to a terminal disclaimer.

(21) Appl. No.: 12/174,337

(22) Filed: Jul. 16, 2008

(65) Prior Publication Data

US 2009/0187206 A1    Jul. 23, 2009

Related U.S. Application Data

(63) Continuation-in-part of application No. 11/807,107, filed on May 25, 2007, now Pat. No. 8,585,771.

(60) Provisional application No. 60/950,071, filed on Jul. 16, 2007, provisional application No. 60/808,820, filed on May 26, 2006.

(51) Int. Cl.
*A61F 2/04* (2013.01)
*A61F 5/00* (2006.01)

(52) U.S. Cl.
CPC ......... *A61F 5/0036* (2013.01); *A61F 2002/045* (2013.01); *A61F 5/0013* (2013.01);
(Continued)

(58) Field of Classification Search
CPC ... A61F 5/0013; A61F 5/0036; A61F 5/0076; A61F 2002/045
USPC ........ 623/1.43, 23.64–23.71; 606/191; 604/8, 604/9
See application file for complete search history.

(56) References Cited

U.S. PATENT DOCUMENTS 2,773,502 A    12/1956 Kaslow et al.
3,546,961 A    12/1970 Marton
(Continued)

FOREIGN PATENT DOCUMENTS

DE    4012642 A1    10/1991
JP    01 015063 A2    1/1989
(Continued)

OTHER PUBLICATIONS

Burnett, Daniel R.; U.S. Appl. No. 60/490,421 entitled "Pyloric valve corking device and method," filed Jul. 28, 2003.
(Continued)

*Primary Examiner* — Thomas J Sweet
*Assistant Examiner* — Megan Wolf
(74) *Attorney, Agent, or Firm* — Shay Glenn LLP

(57) ABSTRACT

The invention relates to devices that are stabilized at an intraluminal residence site in the gastrointestinal tract by their conformation, including dimensions of length and curvature. The device as a whole corresponds to the conformation of the residence site; more particularly, the curved or angled portions correspond to the curved or angled portions of the residence site and do not conform to an immediately proximal or distal site. In some embodiments, the conformationally stabilized device may effect a change in the residence site shape that contributes to stability of the device. Some embodiments are directed toward curbing appetite and/or reducing food intake, other embodiments may be directed toward other therapeutic ends. Some embodiments of the device are designed to reside wholly in the duodenum; others reside principally within the duodenum but extend proximally into the gastric antrum, while other embodiments are designed to reside elsewhere within the gastrointestinal tract.

53 Claims, 49 Drawing Sheets

(52) U.S. Cl.
CPC ... *A61F2210/009* (2013.01); *A61F 2210/0019* (2013.01); *A61F 2210/0014* (2013.01); *A61F 5/003* (2013.01); *A61F 5/0076* (2013.01); *A61F 2002/044* (2013.01)

(56) References Cited

U.S. PATENT DOCUMENTS

| | | |
|---|---|---|
| 4,133,315 A | 1/1979 | Berman et al. |
| 4,134,405 A | 1/1979 | Smit |
| 4,315,509 A * | 2/1982 | Smit ................. 606/108 |
| 4,416,267 A | 11/1983 | Garren et al. |
| 4,485,805 A | 12/1984 | Foster, Jr. |
| 4,501,264 A | 2/1985 | Rockey |
| 4,648,383 A | 3/1987 | Angelchik |
| 4,694,827 A | 9/1987 | Weiner et al. |
| 4,878,905 A | 11/1989 | Blass |
| 4,899,747 A | 2/1990 | Garren et al. |
| 5,019,400 A | 5/1991 | Gombotz et al. |
| 5,084,061 A | 1/1992 | Gau et al. |
| 5,234,454 A | 8/1993 | Bangs |
| 5,259,399 A | 11/1993 | Brown |
| 5,329,942 A | 7/1994 | Gunther et al. |
| 5,396,880 A | 3/1995 | Kagan et al. |
| 5,439,476 A * | 8/1995 | Frantzides ................. 606/192 |
| 5,484,610 A | 1/1996 | Bae |
| 5,597,797 A | 1/1997 | Clark |
| 5,820,584 A | 10/1998 | Crabb |
| 5,868,141 A | 2/1999 | Ellias |
| 6,102,922 A | 8/2000 | Jakobsson et al. |
| 6,160,084 A | 12/2000 | Langer et al. |
| 6,187,330 B1 | 2/2001 | Wang et al. |
| 6,264,700 B1 | 7/2001 | Kilcoyne et al. |
| 6,267,988 B1 | 7/2001 | Meyer |
| 6,281,262 B1 | 8/2001 | Shikinami |
| 6,302,917 B1 | 10/2001 | Dua et al. |
| 6,306,163 B1 | 10/2001 | Fitz |
| 6,336,934 B1 | 1/2002 | Gilson et al. |
| 6,365,173 B1 | 4/2002 | Domb et al. |
| 6,388,043 B1 | 5/2002 | Langer et al. |
| 6,402,687 B1 * | 6/2002 | Ouchi ................. 600/139 |
| 6,540,789 B1 | 4/2003 | Silverman et al. |
| 6,579,301 B1 | 6/2003 | Bales et al. |
| 6,635,431 B1 | 10/2003 | Bihain et al. |
| 6,685,957 B1 | 2/2004 | Bezemer et al. |
| 6,716,444 B1 | 4/2004 | Castro et al. |
| 6,720,402 B2 | 4/2004 | Langer et al. |
| 6,740,121 B2 | 5/2004 | Geitz |
| 6,800,056 B2 | 10/2004 | Tartaglia et al. |
| 6,939,557 B2 | 9/2005 | Rowe et al. |
| 6,946,002 B2 | 9/2005 | Geitz |
| 6,953,560 B1 | 10/2005 | Castro et al. |
| 7,025,791 B2 | 4/2006 | Levine et al. |
| 7,037,344 B2 | 5/2006 | Kagan et al. |
| 7,111,627 B2 | 9/2006 | Stack et al. |
| 7,121,283 B2 | 10/2006 | Stack et al. |
| 7,122,058 B2 | 10/2006 | Levine et al. |
| 7,175,669 B2 | 2/2007 | Geitz |
| 7,223,277 B2 | 5/2007 | DeLegge |
| 7,335,210 B2 | 2/2008 | Smit |
| 7,476,256 B2 | 1/2009 | Meade et al. |
| 7,931,693 B2 * | 4/2011 | Binmoeller ................. 623/23.64 |
| 8,147,561 B2 * | 4/2012 | Binmoeller ................. 623/23.64 |
| 8,585,771 B2 * | 11/2013 | Binmoeller et al. ....... 623/23.64 |
| 8,603,186 B2 * | 12/2013 | Binmoeller ................. 623/23.64 |
| 8,623,095 B2 * | 1/2014 | Binmoeller ................. 623/23.64 |
| 2002/0002384 A1 | 1/2002 | Gilson et al. |
| 2002/0035347 A1 * | 3/2002 | Bagaoisan et al. ............. 604/35 |
| 2002/0035361 A1 * | 3/2002 | Houser et al. .................. 606/15 |
| 2002/0111648 A1 * | 8/2002 | Kusleika et al. ............. 606/200 |
| 2003/0040804 A1 * | 2/2003 | Stack et al. ................. 623/23.7 |
| 2003/0199990 A1 | 10/2003 | Stack et al. |
| 2004/0015187 A1 | 1/2004 | Lendlein et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0088022 A1 | 5/2004 | Chen |
| 2004/0092892 A1 | 5/2004 | Kagan et al. |
| 2004/0110285 A1 | 6/2004 | Lendlein et al. |
| 2004/0122456 A1 | 6/2004 | Saadat et al. |
| 2004/0153118 A1 * | 8/2004 | Clubb et al. ................. 606/200 |
| 2004/0219186 A1 | 11/2004 | Ayres |
| 2004/0267378 A1 | 12/2004 | Gazi et al. |
| 2005/0004681 A1 | 1/2005 | Stack et al. |
| 2005/0033331 A1 | 2/2005 | Burnett |
| 2005/0033332 A1 | 2/2005 | Burnett et al. |
| 2005/0038415 A1 | 2/2005 | Rohr et al. |
| 2005/0049718 A1 | 3/2005 | Dann et al. |
| 2005/0055014 A1 | 3/2005 | Coppeta et al. |
| 2005/0055039 A1 | 3/2005 | Burnett et al. |
| 2005/0075405 A1 | 4/2005 | Wilson et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0090873 A1 | 4/2005 | Imran |
| 2005/0119674 A1 | 6/2005 | Gingras |
| 2005/0125020 A1 | 6/2005 | Meade et al. |
| 2005/0125075 A1 | 6/2005 | Meade et al. |
| 2005/0183732 A1 | 8/2005 | Edwards |
| 2005/0192614 A1 | 9/2005 | Binmoeller |
| 2005/0238694 A1 | 10/2005 | Gerhardt et al. |
| 2005/0245719 A1 | 11/2005 | Mather et al. |
| 2005/0273060 A1 | 12/2005 | Levy et al. |
| 2005/0277975 A1 * | 12/2005 | Saadat et al. ................. 606/191 |
| 2006/0020278 A1 | 1/2006 | Burnett et al. |
| 2006/0064120 A1 | 3/2006 | Levine et al. |
| 2006/0079944 A1 | 4/2006 | Imran |
| 2006/0086362 A1 | 4/2006 | Solomon |
| 2006/0129237 A1 | 6/2006 | Imran |
| 2006/0142794 A1 | 6/2006 | Lendlein et al. |
| 2006/0155311 A1 | 7/2006 | Hashiba et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0247718 A1 | 11/2006 | Starkebaum |
| 2006/0259051 A1 | 11/2006 | Nissl |
| 2006/0265082 A1 | 11/2006 | Meade et al. |
| 2006/0282107 A1 | 12/2006 | Hashiba et al. |
| 2007/0005147 A1 | 1/2007 | Levine et al. |
| 2007/0010864 A1 | 1/2007 | Dann et al. |
| 2007/0010865 A1 | 1/2007 | Dann et al. |
| 2007/0027548 A1 | 2/2007 | Levine et al. |
| 2007/0083271 A1 | 4/2007 | Levine et al. |
| 2007/0110793 A1 | 5/2007 | Kantrowitz et al. |
| 2007/0135768 A1 | 6/2007 | Carlsen |
| 2007/0156159 A1 | 7/2007 | Gannoe et al. |
| 2007/0156248 A1 | 7/2007 | Marco et al. |
| 2007/0239284 A1 | 10/2007 | Skerven et al. |
| 2007/0265598 A1 | 11/2007 | Karasik |
| 2007/0282418 A1 | 12/2007 | Weitzner |
| 2007/0293885 A1 | 12/2007 | Binmoeller et al. |
| 2008/0065136 A1 | 3/2008 | Young |
| 2008/0097510 A1 * | 4/2008 | Albrecht et al. ............. 606/192 |
| 2008/0234834 A1 | 9/2008 | Meade et al. |
| 2013/0109912 A1 | 5/2013 | Binmoeller et al. |
| 2013/0165842 A1 | 6/2013 | Binmoeller |
| 2013/0178782 A1 | 7/2013 | McKinley et al. |
| 2014/0100513 A1 | 4/2014 | Binmoeller |
| 2014/0114228 A1 | 4/2014 | Binmoeller et al. |

FOREIGN PATENT DOCUMENTS

| | | |
|---|---|---|
| JP | 2004509714 | 4/2004 |
| WO | WO 89/00407 A1 | 1/1989 |
| WO | WO 03/094785 A1 | 11/2003 |
| WO | WO 2004/041133 A1 | 5/2004 |
| WO | WO 2004/093753 A2 | 11/2004 |
| WO | WO 2005/120363 A1 | 12/2005 |
| WO | WO 2006/044640 A1 | 4/2006 |
| WO | WO 2006/092789 A2 | 9/2006 |
| WO | WO 2006/102240 A2 | 9/2006 |
| WO | WO 2007/030829 A2 | 3/2007 |

(56) References Cited

FOREIGN PATENT DOCUMENTS

| WO | WO 2007/053556 A1 | 5/2007 |
| WO | WO 2007/053706 A1 | 5/2007 |
| WO | WO 2007/053707 A1 | 5/2007 |
| WO | WO 2007/075396 A2 | 7/2007 |
| WO | WO 2007/139920 A2 | 12/2007 |
| WO | WO2008/001381 A2 | 1/2008 |

OTHER PUBLICATIONS

Burnett, Daniel R.; U.S. Appl. No. 60/525,105 entitled "Intragastric therapeutic device and method," filed Nov. 28, 2003.
Asakawa et al., "Characterization of the effects of pancreatic polypeptide in the regulation of energy balance," Gastroenterology 124(5):1325-36 (May 2003).
Batterham et al., "Gut hormone PYY(3-36) physiologically inhibits food intake," Nature 418(6898): 650-4 (Aug. 8, 2002).
Batterham et al., "Inhibition of food intake in obese subjects by peptide YY3-36," N Engl J Med., 349(10):941-8 (Sep. 4, 2003).
Batterham et al., "Pancreatic polypeptide reduces appetite and food intake in humans," J Clin Endocrinol Metab. 88(8):3989-92 (Aug. 2003).
Caro et al., "Leptin: the tale of an obesity gene," Diabetes 45(11): 1455-62 (Nov. 1996).
Chapman et al., "Effects of small-intestinal fat and carbohydrate infusions on appetite and food intake in obese and nonobese men," Am J Clin Nutr, vol. 69, pp. 6-12 (1999).
Cohen et al., "Oxyntomodulin suppresses appetite and reduces food intake in humans," J Clin Endocrinol Metab., 88(10): 4696-4701 (Oct. 2003).
Collins et al., "Role of leptin in fat regulation," Nature, 380 (6576):677 (Apr. 25, 1996).
D'Alessio et al., "Activation of the parasympathetic nervous system is necessary for normal meal-induced insulin secretion in rhesus macaques," J Clin Endocrinol Metab., 86(3): 1253-9 (Mar. 2001).
Davis et al., "Distension of the small intestine, satiety, and the control of food intake," Am Journal of Clinical Nutrition, vol. 31, pp. S255-S258 (1978).
de Castro et al., "A general model of intake regulation," Neuroscience and Biobehavioral Reviews, vol. 26, pp. 581-595 (2002).
French et al.,"Is Cholecystokinin a Satiety Hormone? Correlations of Plasma Cholecystokinin with Hunger, Satiety, and Gastric Empyting in Normal Volunteers," Appetite, vol. 16, pp. 95-104 (1993).
Gao et al., "Sensory and biomechanical responses to ramp-controlled distension of the human duodenum," Am. J. Physiol. Gas., vol. 284, pp. G461-G471 (2003).
Geliebter et al., "Clinical trial of silicone rubber gastric balloon to treat obesity," Int J Obesity, 15(4): 259-266 (1991).
Ghatei et al., "Molecular forms of human enteroglucagon in tissue and plasma: plasma responses to nutrient stimuli in health and in disorders of the upper gastrointestinal tract," J Clin Endocrinol Metab, 57(3):488-95 (Sep. 1983).
Gibbs et al., "Cholecystokinin descreases food intake in rats," J Comp Physiol Psychol. 84(3):488-95 (Sep. 1973).
Havel, Peter, "Peripheral signals conveying metabolic information to the brain: Short-term and long-term regulation of food intake and energy homeostasis," Society for Experimental Biology and Medicine, vol. 226, pp. 963-977 (2001).
Havel, PJ, "Role of adipose tissue in body-weight regulation: mechanisms regulating leptin production and energy balance," Proc Nutr Soc. 59(3):359-71 (Aug. 2000).
Haynes et al., "Receptor-mediated regional sympathetic nerve activation by leptin," J Clin Invest. 100(2): 270-278 (Jul. 15, 1997).
Herrmann et al., "Glucagon-like peptide-1 and glucose-dependent insulin-releasing polypeptide plasma levels in response to nutrients," Digestion 56(2):117-26 (1995).
Kissileff et al., "Cholecystokinin and stomach distension combine to reduce food intake in humans," Am J Physiol Regul Integr Comp Physiol., 285(5):R992-8 (Nov. 2003).
Le Quellec et al., "Oxyntomodulin-like immunoreactivity: diurnal profile of a new potential entergastrone," J Clin Endocrinol Metab, 74(6): 1405-9 (Jun. 1992).
Levin et al., "Decreased food intake does not completely account for adiposity reduction after ob protein infusion," Proc Natl Acad Sci U.S.A., 93(4): 1726-30 (Feb. 20, 1996).
Liddle et al., "Cholecystokinin bioactivity in human plasma. Molecular forms, responses to feeding, and relationship to gallbladder contraction," J Clin Invest. 75(4):1144-52 (Apr. 1985).
Lindor et al., "Intragastric balloons in comparison with standard therapy for obesity—a randomized, double-blind trial," Mayo Clin Proc 62(11): 992-6 (Nov. 1987).
Malaisse-Lagae et al., "Pancreatic polypeptide: a possible role in the regulation of food intake in the mouse. (Hypothesis)" Experientia 15; 33(7):915-917 (Jul. 15, 1977).
Mathus-Vliegen et al., "Intragastric balloon in the treatment of supermorbid obesity. Double-blind, sham-controlled, crossover evaluation of 500-millimeter balloon,"Gastroenterology, 99(2): 362-369 (Aug. 1990).
Moran el al, "Neurobiology of cholecystokinin," Crit Rev Neurobiol. 9(1): 1-28 (1994).
Moran et al., "Gastrointestinal satiety signals," Am J Physiol Gastrointest Liver Physiol, vol. 286, pp. G183-G188 (2004).
Näslund et al., "GLP-1 slows solid gastric emptying and inhibits insulin, glucagon, and PYY release in humans," Am J Physiol 277 (3 Pt 2):R910-R916 (Sep. 1999).
Rayner et al., "Effects of cholecystokinin on appetite and pyloric motility during physiological hyperglycermia," Am. J. Physiol. Gastrointest. Liver Physiol. , vol. 278, pp. G98-G104 (2000).
Read et al., "The Role of the Gut in Regulating Food Intake in Man," Nutrition Reviews, vol. 52, pp. 1-10 (1994).
Read, N.W. "Role of gastrointestinal factors in hunger and satiety in man," Proceedings of the Nutrition Society, vol. 51, pp. 7-11 (1992).
Remington: The Science and Practice of Pharmacy, 20th Ed., Chap. 47, Controlled Release Drug Delivery Systems.
Remington's Pharmaceutical Sciences, 17th Ed., "Freeze-drying," p. 1538.-1539.
Rigaud et al., "Gastric distension, hunger, and energy intake after balloon implantation in severe obesity," Int J Obes Relat Metab Disor., Jul; 19(7):489-95 (1995).
Scarpace et al., "Leptin increases uncoupling protein expression and energy expenditure," Am J Physiol., 273 (1 Pt 1): E226-230 (Jul. 1997).
Schirra et al., Mechanisms of the antidiabetic action of subcutaneous glucagon-like peptide-1 (7-36)amide in non-insulin dependent diabetes mellitus, J Endocrinol. 156(1):177-86 (Jan. 1998).
Schwartz et al., "Central nervous system control of food intake," Nature, 404(6778): 661-671 (Apr. 6, 2000).
Schwartz et al., "Keeping hunger at bay," Nature, vol. 418, pp. 595-597 (2002).
Schwartz et al., "Model for the regulation of energy balance and adiposity by the central nervous system," Am J Clin Nutr., 69(4): 584-96 (Apr. 1999).
Standring, Susan (ed). Gray's Anatomy, 39th Ed. 1163-64 (2005).
Wilding, J. P. H., "Neuropeptides and appetite control," Diabetes U.K. Diabetic Medicine, vol. 19, pp. 619-627 (2002).
Woods et al., "The Regulation of Food Intake by Peptides," Annals of the New York Academy of Sciences, vol. 575. pp. 236-243 (1989).
Wynne et al., "Appetite control," Journal of Endocrinology, vol. 184, pp. 291-318 (2005).
McKinley et al.; U.S. Appl. No. 12/999,180 entitled "Methods and devices for delivering or delaying lipids within a duodenum," filed Jan. 31, 2011.
Wang et al.; Upper intestinal lipids trigger a gut-brain-liver axis to regulate glucose production; Nature; vol. 452; pp. 1012-1016; Apr. 24, 2008.
Ritter, Robert C.; Gastrointestinal mechanisms of satiation for food; Physiol Behav.; 81(2):249-73; Apr. 2004.

* cited by examiner

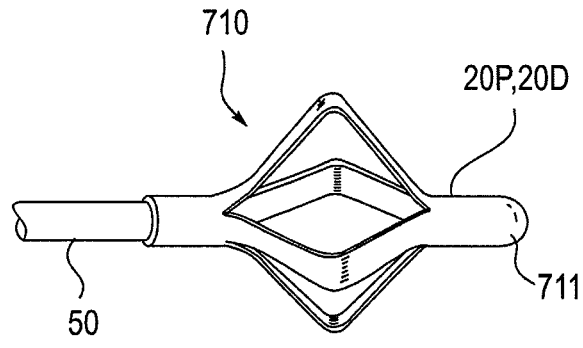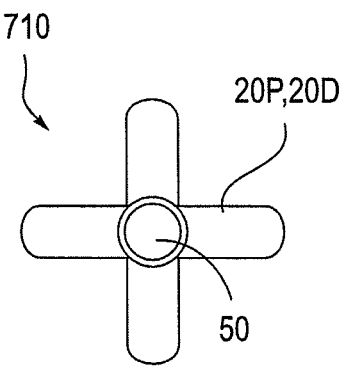
FIG. 49A  FIG. 49B
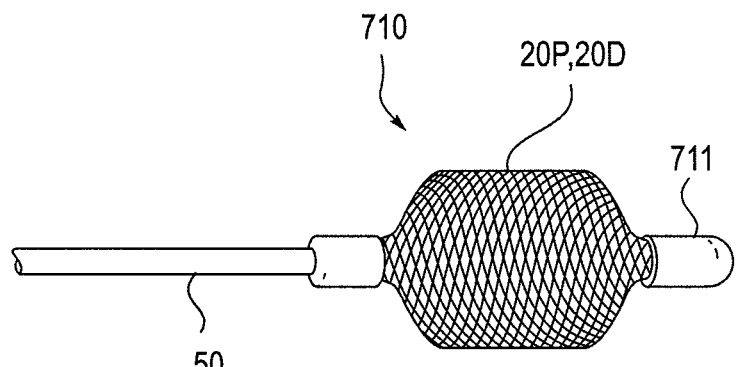
FIG. 49C
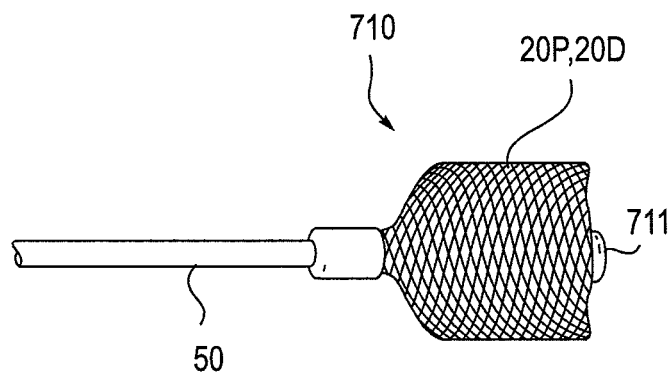
FIG. 49D

CONFORMATIONALLY-STABILIZED INTRALUMINAL DEVICE FOR MEDICAL APPLICATIONS

CROSS REFERENCE TO RELATED APPLICATIONS

This patent application claims the benefit of U.S. Provisional Patent Application No. 60/950,071 of Binmoeller et al., entitled "A Conformationally-Stabilized Intraluminal Device for Medical Applications", filed on Jul. 16, 2007. This patent application is also a continuation-in-part of U.S. patent application Ser. No. 11/807,107, now U.S. Pat. No. 8,585,771, entitled "Methods and Devices to Curb Appetite and/or Reduce Food Intake" of Binmoeller et al., which was filed on May 25, 2007, and which claimed priority under 35 U.S.C. § 119 to U.S. Provisional Patent Application No. 60/808,820 of Binmoeller, filed on May 26, 2006, entitled "Improvements in Methods and Devices to Curb Appetite and/or Reduce Food Intake."

INCORPORATION BY REFERENCE

All publications, patents and patent applications mentioned in this specification are herein incorporated by reference to the same extent as if each individual publication, patent or patent application was specifically and individually indicated to be incorporated by reference.

FIELD OF THE INVENTION

The invention is in the field of medical devices that reside within a lumen of the gastrointestinal tract and provide a platform for medical applications. More particularly, embodiments of the invention stabilize at a luminal residence site by virtue of their physical conformation.

BACKGROUND OF THE INVENTION

Obesity, defined as a body mass index (BMI) of greater than 30, is a major health concern in the United States and other countries; it has been estimated that one in three Americans and more than 300 million people world-wide are obese. Complications of obesity include many serious and life-threatening diseases including hypertension, diabetes, coronary artery disease, stroke, congestive heart failure, pulmonary insufficiency, multiple orthopedic problems, various cancers and a markedly decreased life expectancy. Intentional weight loss, however, can improve many of these medical complications associated with obesity.

While weight loss can improve many of the medical complications associated with obesity, its management as a health concern has proven troublesome. A variety of approaches including dietary methods, psychotherapy, behavior modification, and pharmacotherapy have each met with some success but as a whole failed to effectively control the rapid growth in the incidence and severity of obesity seen in the United States. The severity of problems associated with obesity also has led to the development of several drastic surgical procedures. One such procedure physically reduces the size of the stomach so that a person cannot consume as much food as was previously possible. These stomach reduction surgeries had limited early success, but now it is known that the stomach can stretch back to a larger volume over time, limiting the achievement of sustained weight loss in many individuals. Another drastic surgical procedure induces the malabsorption of food by reducing the absorptive surface of the gastrointestinal (GI) tract, generally via by-passing portions of the small intestine. This gastric by-pass procedure further has been combined with stomach reduction surgery. While these described surgical procedures can be effective to induce a reduction in food intake and/or overall weight loss in some, the surgical procedures are highly invasive and cause undue pain and discomfort. Further, the described procedures may result in numerous life-threatening postoperative complications. These surgical procedures are also expensive, difficult to reverse, and place a large burden on the national health care system.

Non-surgical approaches for the treatment of obesity also have been developed. For example, one non-surgical endoscopic approach to treating obesity includes the placement of a gastric balloon within the stomach. The gastric balloon fills a portion of the stomach, providing the patient with a feeling of fullness, thereby reducing food intake. This approach has yet to be convincingly shown to be successful, and a number of problems are associated with the gastric balloon device, however, including poor patient tolerance and complications due to rupture and/or migration of the balloon. Other non-surgical devices designed to induce weight loss limit the absorption of nutrients in the small intestine by funneling food from the stomach into a tube found within the small intestine so that the food is not fully digested or absorbed within the small intestine. While this type of device may be somewhat effective at limiting the absorption of consumed food, there is still room for a variety of improvements in non-surgical devices designed to induce weight loss and/or a reduction in food intake.

An understanding of biological events that contribute to the creation of satiety signals provides an opportunity to develop "smart" nonsurgical devices that can trigger such events. The amount of food that individuals consume is largely dependent on biological signals between the gut and the brain. Specifically, hormonal signals from the gut to the brain are correlated with both the onset and cessation of food intake. While increased levels of hormones such as ghrelin, motilin and agouti-related peptide are involved in the promotion of appetite and the onset of food intake, increased levels of a number of other hormones are involved in the cessation of food intake.

Various biologic events contribute to the physiologic cessation of food intake. Generally, as a meal is consumed, the ingested food and by-products of digestion interact with an array of receptors along the GI tract to create satiety signals. Satiety signals communicate to the brain that an adequate amount of food has been consumed and that an organism should stop eating. Specifically, GI tract chemoreceptors respond to products of digestion (such as sugars, fatty acids, amino acids and peptides) while stretch receptors in the stomach and proximal small intestine respond to the physical presence of consumed foods. Chemoreceptors respond to the products of digestion by causing the release of hormones or other molecular signals. These released hormones and/or other molecular signals can stimulate nerve fibers to send satiety signals to the brain. The arrival of these signals in the brain can trigger a variety of neural pathways that can reduce food intake. The released hormones and/or other molecular signals can also travel to the brain themselves to help create signals of satiety. Mechanoreceptors generally send satiety signals to the brain through stimulation of nerve fibers in the periphery that signal the brain. The present invention provides methods and devices that help to reduce food intake by providing non-surgical devices and methods that trigger the aforementioned biological events that contribute to the creation of satiety signals.

SUMMARY OF THE INVENTION

In one embodiment of the present invention, there is provided a duodenal device having a solid elongate body having a proximal end, a distal end and a central curved portion between the proximal end and the distal end. The length of the elongated body is selected such that, in use within the gastrointestinal tract, the proximal end is within the stomach proximal to the pylorus and the distal end is within the distal duodenum and in proximity to the proximal end. In one aspect, the length of the elongate body is selected to place the distal end adjacent to the duodenojejunal junction. In another aspect, at least the proximal end is sized for atraumatic passage through the pylorus. In another aspect, the device is configured to remain in position within the gastrointestinal tract without connecting to a wall of the gastrointestinal tract. In still another aspect, at least a portion of the central curved portion is configured to conform to the shape of the duodenum. In other aspects, the length of the elongate body is selected to position the proximal end in the stomach, near the distal end when the device is in use or the length of the elongate body is selected to position the proximal end in or against the stomach antrum when the device is in use. In still other alternatives, the elongate body comprises a tapered end portion near the proximal end or the distal end, or, alternatively the elongate body comprises at least one diameter reducing area and at least one diameter increasing area.

In still other alternative embodiments, the device includes an atraumatic feature on the proximal end or the distal end. The atraumatic feature is a coil, or includes a pad or a mesh or braided structure. In still other alternatives, an atraumatic feature on the proximal end with a tissue contact surface and an atraumatic feature on the distal end with a surface shaped to at least partially conform to the shape of the tissue contact surface. In one aspect, the atraumatic feature on the proximal end comprises a pad and the atraumatic feature on the distal end comprises a mesh structure. In one aspect, the pad is spoon shaped, or includes a convex surface or includes a concave surface.

In other aspects, the elongate body includes a bulbous tip on the proximal end or a bulbous tip on the distal end. In one alternative, the bulbous tip is formed from the elongate body. In another aspect, the elongated body comprises a shape memory material, and the material may be Nitinol or other suitable shape memory material metal or shape memory polymer. In still another aspect, the elongate body, the proximal end, the distal end and the central curved portion are formed from a single piece of shape memory material. There may also be a coating around the elongate body and the coating may be a tube formed from a biocompatible polymer.

In still another additional aspect, the device may also include at least one flow reduction element positioned on the elongate body central curved portion. In one embodiment, the at least one flow reduction element comprises a braided structure. In one aspect, the braided structure ranges from 8 picks per inch to 16 picks per inch. In another aspect, the portion of the braided structure is secured to the elongate body and a portion of the braided structure is freely slideable relative to the elongate body. In still another aspect, the braided structure assumes a preformed shape when the portion of the braided structure that is freely slideable moves towards the portion of the braided structure that is secured to the elongate body. In still another aspect, the preformed shape comprises a plurality of flow reduction forms. In another aspect, the braided structure comprises polymer filaments. In other aspects, the at least one flow reduction element is arranged around the elongate body. In another alternative, the at least one flow reduction element includes one or more radially expandable segments. In still another aspect, a portion of the flow reduction element is attached to the elongate body. In another aspect, a portion of the flow reduction element is freely slideable over the elongate body. In another aspect, the device includes a feature on the elongate body distal to the proximal end configured to engage a deployment device. In another alternative, the device includes a stopping feature on the elongate body adapted to prevent movement of the freely slideable portion of the at least one flow reduction element. In one aspect, the stopping feature is positioned on the elongate body proximal to the portion of the flow reduction element that is attached to the elongate body.

In another embodiment, there is a method of providing therapy in a gastrointestinal tract including the step of positioning the distal end of a device into a first portion of a gastrointestinal tract residence site. Next, there is the step of conforming a portion of the device proximal to the distal end of the device to a second portion of the gastrointestinal tract residence site. Next, there is the step of positioning the proximal end of the device into a third portion of the gastrointestinal tract residence site. In one aspect, the second portion of the gastrointestinal tract residence site includes at least one of: the transition from the duodenal bulb to the vertical duodenum; the transition from the vertical duodenum to the horizontal duodenum; the transition from the horizontal duodenum to the jejunum; the duodenojejunal flexure; and the portion of the duodenum adjacent to the Ligament of Treitz. In another aspect, the positioning the distal end of a device step includes deploying an atraumatic feature into contact with the first portion of a gastrointestinal tract residence site. In another aspect, the positioning the proximal end of a device step includes deploying an atraumatic feature into contact with the third portion of a gastrointestinal tract residence site. The method may also include aligning the atraumatic feature on the proximal end of the device with the atraumatic feature on the distal end of the device.

In other aspects, the first portion of a gastrointestinal tract residence site is distal to the vertical duodenum or the first portion of a gastrointestinal tract residence site is within to the horizontal duodenum. In another aspect, the first portion of a gastrointestinal tract residence site is within or distal to the horizontal duodenum and adjacent to the third portion of the gastrointestinal tract residence site. In still another aspect, the first portion of a gastrointestinal tract residence site is within or near the duodenojejunal flexure. In another aspect, the first portion of a gastrointestinal tract residence site is within or near the portion of the duodenum adjacent to the Ligament of Treitz. In another aspect, the third portion of a gastrointestinal tract residence site is proximal to the pylorus. In another aspect, the third portion of a gastrointestinal tract residence site is within the antrum of the stomach. In another alternative, after the deploying step, the atraumatic feature is in contact with the stomach wall in the antrum.

In another alternative, the method includes the step of maintaining the position of the device within the gastrointestinal residence site without impairing pyloric function or gastric emptying. In another aspect, the method includes the step of maintaining the position of the device within the gastrointestinal residence site while atraumatically withstanding peristaltic action. In still another aspect, after performing the steps of the method, the proximal end of the device is within 1 to 7 cm of the distal end of the device. In another aspect, the proximal end of the device is separated from the distal end of the device by a portion of the stomach wall and a portion of duodenal wall. In still another aspect, after performing the delivery step, the proximal end of the device is separated from the atraumatic feature by a portion of the stomach wall and a portion of duodenal wall. In still another aspect, after performing the delivery step, the distal end of the device is separated from the atraumatic feature by a portion of the stomach wall and a portion of duodenal wall.

In other embodiments, the conforming step also includes moving the device relative to the gastrointestinal residence site to assume a portion of a preformed device shape. Additionally, the conforming step may include moving the device relative to the gastrointestinal residence site to obtain a preselected alignment of the proximal end and the distal end of the device. In some embodiments, the force to accomplish a moving step is provided by a shape memory component of the device.

In still other aspects of the method, there is the additional step of providing therapy from the device. In one alternative, the step of providing therapy includes deploying at least one flow reduction element from the device to reduce the flow of chyme past the device. In another aspect, the providing therapy step includes providing electrical stimulation from the device to a portion of the gastrointestinal residence site. In one aspect, the electrical stimulation in the providing step produces a sensation of satiety in the patient. In still other aspects, the providing therapy step includes providing mechanical stimulation from the device to a portion of the gastrointestinal site. In one alternative, the mechanical stimulation in the providing step produces a sensation of satiety in the patient. In still another alternative, the providing therapy step includes providing a bioactive agent from the device to a portion of the gastrointestinal site. In one aspect, the step of providing a bioactive agent produces a sensation of satiety in the patient. In one aspect, the providing therapy step is selected to cause loss of excess weight in a patient. In still other aspects, the providing therapy step includes positioning the device to provide slowing of chyme flow through the duodenum.

BRIEF DESCRIPTION OF THE DRAWINGS

FIG. 27 depicts an embodiment of the central member of an insert that includes biodegradable elements and shape memory elements.

FIG. 28 depicts an embodiment of the central member of an insert that includes a biodegradable shape memory polymeric material.

FIG. 46A depicts a device with a relatively long separation between ends and a relatively large end-end cross over dimension. FIG. 46B depicts a device with a relatively short separation between ends and a relatively small end-end cross over dimension.

FIGS. 49A-49D show alternative atraumatic end features. FIG. 49A shows an end piece formed by shape memory material that radially expands in a lantern like fashion when released from linear constraint. FIG. 49B shows an end view of the end piece of FIG. 48A 49A. FIG. 49C shows an end piece in the form of an expandable braided sphere with a blunt distal end. FIG. 49D shows an end piece in the form of an expandable braided sphere with an invaginated distal end.

FIG. 50A shows a top view. FIG. 50B shows a side view. FIG. 50C shows an end view, depicting a curvature that reflects a rollable bias. FIG. 50D shows an end view of the spoon feature rolled into a stowable configuration for inclusion in an endoscope working channel or delivery sheath.

DETAILED DESCRIPTION

Embodiments of the Device In Situ

Figure 1:
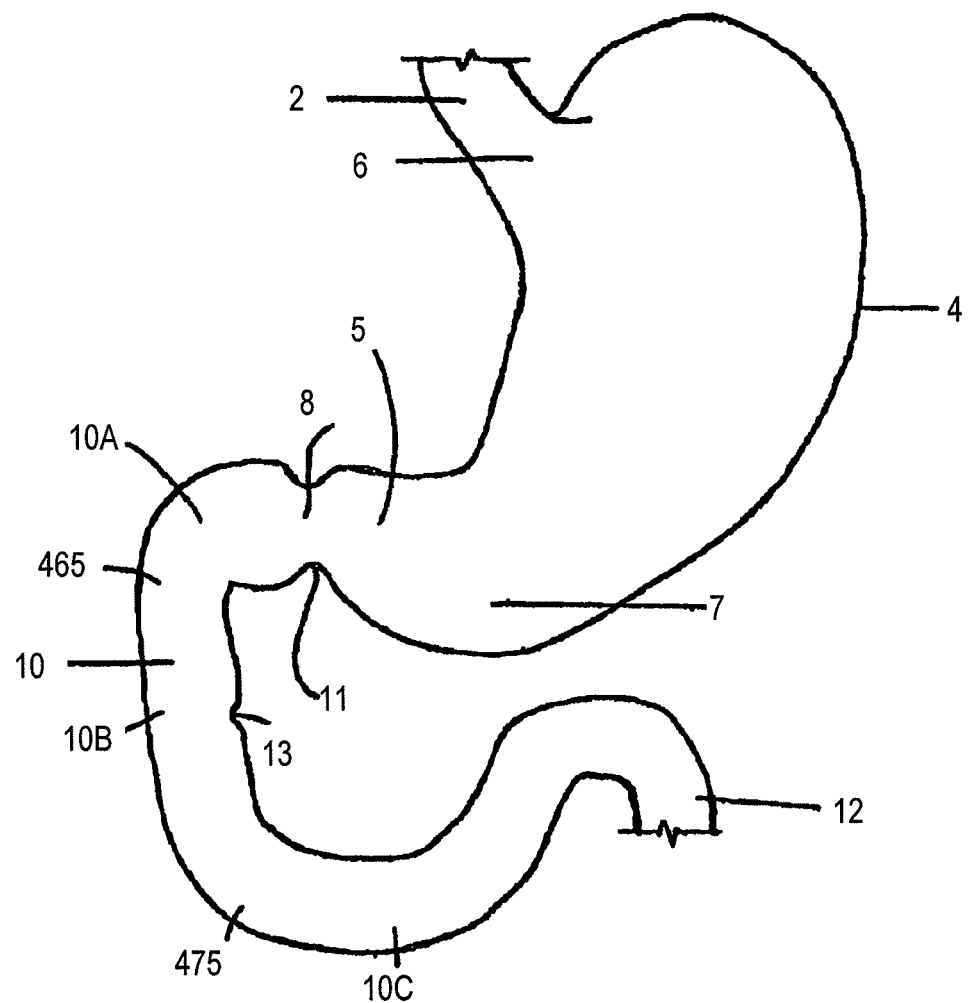
FIG. 1 is a general drawing of the stomach and duodenum of the small intestine.

FIG. 1 provides a view of the human gastrointestinal tract, including the stomach 4 and duodenum of the small intestine 10. Important features are the esophagus 2, stomach 4, antrum 7, pylorus 8, pyloric valve 11, duodenum 10, jejunum 12 and ampulla of Vater (or hepatopancreatic ampulla) 13, which is formed by the union of the pancreatic duct and the common bile duct. Functionally, the esophagus 2 begins at the nose or mouth at its superior end and ends at the stomach 4 at its inferior end. The stomach 4 encloses a chamber which is characterized, in part, by the esophageal-gastric juncture 6 (an opening for the esophagus 2) and the antrum-pyloric juncture 5 (a passageway between the antrum 7 through the pylorus 8 to the duodenum 10 of the small intestine). The pylorus 8 controls the discharge of contents of the stomach 4 through a sphincter muscle, the pyloric valve 11, which allows the pylorus 8 to open wide enough to pass sufficiently-digested stomach contents (i.e., objects of about one cubic centimeter or less). These gastric contents, after passing into the duodenum 10, continue into the jejunum 12 and on into the ileum (not shown). The duodenum 10, jejunum 12 and ileum make up what is known as the small intestine. However these individual portions of the alimentary canal are sometimes individually referred to as the small intestine. In the context of this invention the small intestine can refer to all or part of the duodenum, jejunum and/or ileum. The ampulla of Vater 13, which provides bile and pancreatic fluids that aid in digestion, is shown as a small protrusion on the medial wall of the duodenum 10.

Embodiments of the inventive device include various forms that provide stability in a residence site in the gastrointestinal tract, particularly the duodenum. Some embodiments of the device, which may be synonymously referred to as an intestinal insert, are stabilized in the intestine by way of an anchoring member that resides in the stomach and is too large to be swept through the pylorus. Other embodiments reside stably in the intestine not by virtue of a separate anchoring member in the stomach, but rather by virtue of the device as a whole fitting into the small intestine with angled portions that fit or correspond with angled portions of the intestine, and the device further having a sufficient structural integrity that it resists being moved distally because the distal location does not physically accommodate the shape of the device. Embodiments that are further described in a following section, rather than having angled sections per se, have instead, a curvilinear central portion. Aspects of the device that are adapted to provide anchorless stabilization at a target site in the intestine include physical dimensions of length and width, as well as angles of the device, all of which complement the target portion of intestine. In other embodiments, stabilizing features in the intestine may include expanded portions of the device in the duodenal bulb, which is larger than the more distal portion of the duodenum, and which thereby effectively prevents distal movement (as in FIG. 18, for example).

Some embodiments of the device and associated methods of using the device are directed toward reducing the rate of food transit through the intestine by physical mechanisms of intervening in the rate of food transit. In other aspects, embodiments of the invention act by eliciting satiety signals by way of physiological mechanisms, or, alternatively, by directly providing satiety signals through bioactive materials or agents, or by neuronal stimulation, thereby reducing food intake behaviorally. Some embodiments of the device are directed toward medical purposes broader than satiety and digestive physiology alone, although the satiety and food consumption functionalities of embodiments of the device and method will be described herein in greater detail. As an example of non-obesity or satiety-inducing medical use, some embodiments of the devise may be used as an eluting source for bioactive agents (described in greater detail below, and depicted in FIG. 25), and as such any medically appropriate drug could be delivered by such a device. In some aspects, embodiments of the device may contribute to slowing food transit and/or reducing food intake by the satiety signals generated by the intestine in direct response to the mere physical presence of the device. Such signals could, for example, be mediated by stretch-responsive neurons or mechanoreceptors in the intestinal wall. In other embodiments, satiety signals could be mediated by hormones that are responsive to physical presence of material in the intestine, or which are secondarily responsive to mechano-receptors. In other embodiments, the slowing of food or the increased residency time, and the consequent change in the chemical environment of the intestine, may elicit responses from chemoreceptors residing in the intestine to signal either neurally or hormonally in such a way that has a net effect of signaling satiety.

In still other embodiments of the invention, the device may convey bioactive material or agents that are released over time within the intestine, the bioactive agents conveying a net signal of satiety. In some embodiments, the bioactive agents with a net satiety signaling effect are passively released from sites such as coatings, depots, or reservoirs within the device. Bioactive materials or agents have been described in detail above, but briefly and in broad aspect may include any of hormones, drugs, or cells. In some embodiments, bioactive agents may be held in osmotic pumps and released by osmotic drive. Release mechanisms such as osmotic pumps provide a level of control and predictability to bioactive agent release, but the mechanism remains relatively passive and without means of intervention. Other embodiments of the invention, however, may include more active mechanisms for bioactive agents release or delivery, as could be provided by electrically driven pumps, or by piezoelectric elements that allow or promote the release stored bioactive agents in response to applied current. Such devices may include power storage elements, or may be provided power by external sources by wired or wireless approaches.

In still other embodiments of the invention, the device may include electrodes or conductive elements that provide electrical stimulation to nerves in the intestine, such resulting neural activity contributing to a net effect of signaling satiety to the brain. In some embodiments, satiety-related neuronal activity may further be mediated by endocrine mechanisms. As in embodiments of the invention with powered mechanisms for bioactive agent release, embodiments with electrical capability may include power storage devices, or be enabled to receive energy conveyed from external sources.

In other aspects of the invention, embodiments of the inserted device, with or without an anchor, may provide a platform for bioactive agent delivery, neural stimulus delivery, or radiation therapy delivery, for medical purposes more broad than inducing satiety, or intervening in food transit. For the delivery of some bioactive agents, there may be considerable advantage associated with local delivery of an agent to an intestinal site. Such advantages may include localization of dosing, lack of exposure to stomach acid as occurs in oral delivery or diminished exposure to the metabolic machinery of the liver and kidney that i.v. drug delivery, or any form of systemic delivery faces. Further, embodiments of the device may accommodate multiple drugs; in some embodiments the release of such multiple drugs may be independently controlled.

Digestive System Context of Invention

The description now addresses the digestive system, the digestive process, and aspects of the endocrinology and neurophysiology of satiety as they relate to embodiments of the invention. The adult duodenum is about 20-25 cm long and is the shortest, widest, and most predictably placed part of the small intestine. The duodenum forms an elongated C-shaped configuration that lies between the level of the first and third lumbar vertebrae in the supine position. Susan Standring (ed.), Gray's Anatomy, 39th Ed., 1163-64 (2005), provides a standard reference. Returning to FIG. 1 for reference and further detail of aspects of the digestive system, the first part of the duodenum, often referred to as the duodenal bulb 10a, is about 5 cm long and starts as a continuation of the duodenal end of the pylorus 8. This first part of the duodenum passes superiorly, posteriorly and laterally for 5 cm before curving sharply inferiorly into the superior duodenal flexure 465, which marks the end of the first part of the duodenum. The second part of the duodenum, often called the vertical duodenum 10b, is about 8-10 cm long. It starts at the superior duodenal flexure 465 and runs inferiorly in a gentle curve towards the third lumbar vertebral body. Here, it turns sharply medially into the inferior duodenal flexure 475 which marks its junction with the third part of the duodenum. The third part of the duodenum, often called the horizontal duodenum 10c, starts at the inferior duodenal flexure and is about 10 cm long. It runs from the right side of the lower border of the third lumbar vertebra, angled slightly superiorly, across to the left and ends in continuity with the fourth part of the duodenum in front of the abdominal aorta. The fourth part of the duodenum is about 2.5 cm in length; it starts just to the left of the aorta and runs superiorly and laterally to the level of the upper border of the second lumbar vertebra. It then turns antero-inferiorly at the duodenojejunal flexure and is continuous with the jejunum. Some embodiments of the present invention take advantage of this predictable configuration of the small intestine to provide duodenal/small intestinal implants that do not require anchoring within the pylorus or stomach, as described more fully below.

The digestive process starts when consumed foods are mixed with saliva and enzymes in the mouth. Once food is swallowed, digestion continues in the esophagus and in the stomach, where the food is combined with acids and additional enzymes to liquefy it. The food resides in the stomach for a time and then passes into the duodenum of the small intestine to be intermixed with bile and pancreatic juice. Mixture of the consumed food with bile and pancreatic juice makes the nutrients contained therein available for absorption by the villi and microvilli of the small intestine and by other absorptive organs of the body.

Robert C. Ritter, author of "Gastrointestinal mechanisms of satiation for food", published by Physiology & Behavior 81 (2004) 249-273, summarizes our understanding of the various means the gastrointestinal tract uses to control appetite. He states that the role of the stomach in satiation is to sense the volume of ingesta arriving from a meal and to produce a variety of signaling substances that may be involved in satiation. It is, however, the small intestine specifically that receives these signals. Further, it is the intestine that responds to the energy density of ingesta, limiting further gastric emptying and signally satiety when adequate calories have passed. Through analysis of the location of afferent nerves (p. 255), Ritter shows that vagal nerve afferents are most concentrated in the duodenum and least concentrated more distally in the ileum. This early concentration of afferents will moderate appetite early in the eating process. The timeliness of the response to nutrient intake has been further demonstrated by others in a variety of mammals including monkeys, rats and humans. It is clear that the reduction in food intake begins within minutes of the start of intake and that this reduction is not therefore a response to postabsorptive or systematic metabolic effects. These passages of Ritter are specifically incorporated herein by reference as relates to the positioning of the devices described herein or for the placement and size of flow reduction elements of embodiments of the present invention.

The presence of partially digested food within the stomach and small intestine initiates a cascade of biological signals that create satiety signals principally emanating from the proximal small intestine that contribute to the cessation of food intake. One such satiety signal is initiated by the release of cholecystokinin (CCK). Cells of the small intestine release CCK in response to the presence of digested foods, and in particular, in response to dietary fat, fatty acids, small peptides, and amino acids. Elevated levels of CCK reduce meal size and duration and may do so through a number of different mechanisms. For example, CCK may act on CCK-A receptors in the liver and within the central nervous system to induce satiety signals. CCK stimulates vagal afferent fibers in both the liver and the pylorus that project to the nucleus tractus solitarius, an area of the brain that communicates with the hypothalamus to centrally regulate food intake and feeding behavior. CCK also stimulates the release of enzymes from the pancreas and gall bladder and inhibits gastric emptying. Because CCK is a potent inhibitor of gastric emptying, some of its effects on limiting food intake may be mediated by the retention of food in the stomach.

Cells of the small intestine (particularly L cells) also release glucagon-like peptide 1 (GLP-1) and oxyntomodulin (OXM) in response to nutrient signals of digestion. Elevated levels of GLP-1 and OXM are associated with satiety signals and the cessation of food intake. These hormones may signal satiety by activating receptors on afferent vagal nerves in the liver and/or the GI tract and/or by inhibiting gastric emptying.

Pancreatic peptide (PP) is released in proportion to the number of calories ingested, and in response to gastric distension. Elevated levels of PP have been shown to reduce food intake and body weight. PP may exert some of its anorectic effects via vagal afferent pathways to the brainstem, as well as through more local effects, such as by suppression of gastric ghrelin production.

Peptide $YY_{3-36}$ ($PYY_{3-36}$) is another biological signal whose peripheral release may be correlated with reduced food intake and/or the cessation of eating. Specifically, low levels of $PYY_{3-36}$ have been correlated with obesity while its administration decreases caloric intake and subjective hunger scores. Intravenous administration of $PYY_{3-36}$ may reduce food intake through its effects of suppressing ghrelin expression, delaying gastric emptying, delaying various secretion from the pancreas and stomach and increasing the absorption of fluids and electrolytes from the ileum after a meal.

Insulin and leptin are two additional biological signals that regulate satiety and eating behavior. Through parasympathetic innervation, beta cells of the endocrine pancreas release insulin in response to circulating nutrients such as glucose and amino acids, and in response to the presence of GLP-1 and gastric inhibitory peptide (GIP). Insulin stimulates leptin production from adipose tissue via increased glucose metabolism. Increased insulin levels in the brain leads to a reduction in food intake. Elevated leptin levels also decrease food intake and induce weight loss. Insulin and leptin have also been implicated in the regulation of energy expenditure since their administration induces greater weight loss than can be explained by reduction in food intake alone. Both insulin and leptin act within the central nervous system to inhibit food intake and to increase energy expenditure, most likely by activating the sympathetic nervous system. Insulin's effects to decrease food intake also involve interactions with several hypothalamic neuropeptides that are also involved in the regulation of feeding behavior such as, by way of example, NPY and melanocortin ligands.

Other hormones or biological signals that are involved in the suppression or inhibition of food intake include, by way of example, GIP (secreted from intestinal endocrine K cells after glucose administration or ingestion of high carbohydrate meals; enterostatin (produced in response to dietary fat; amylin (co-secreted with insulin from pancreatic beta cells); glucagon, gastrin-releasing peptide (GRP), somatostatin, neurotensin, bombesin, calcitonin, calcitonin gene-related peptide, neuromedin U (NMU), and ketones.

In relation to embodiments of the present invention, when the passage of partially digested food or chyme is partially impeded within the duodenum of the small intestine and the flow rate through this area is reduced (or to express the same phenomenon in another way, as residency time is increased), the emptying of the stomach and the duodenum will occur more slowly. This slowing, by itself, may create extended feelings of satiety and thus lead to a decrease in food intake (due to the longer retention time of food in the stomach). The slowing of the passage of food also provides more time for the partially digested food to interact with chemoreceptors, stretch receptors, and mechanoreceptors along the GI tract so that stimulation of satiety signals may be increased and/or prolonged, which may, in turn, lead to a reduction in food intake during an eating period and/or longer periods between food intake.

In addition to keeping partially-digested food within the small intestine for an extended period of time, the methods and devices of the present invention may also enhance and/or prolong the release of satiety signals by releasing signals into the small intestine themselves. For example, in some embodiments, the methods and devices of the present invention may release nutrient products of digestion to stimulate chemoreceptors to cause the release of hormones and/or other molecular signals that contribute to the creation of satiety signals. In another embodiment, the methods and devices of the present invention may exert a small amount of pressure on the walls of the GI tract to stimulate stretch (mechanoreceptors) to generate and send satiety signals to the brain. In another embodiment, the methods and devices of the present invention may release signals, such as, by way of example, nutrient by-products of digestion of food, to stimulate chemoreceptors as described above and may exert a small amount of pressure on the walls of the small intestine as described above to contribute to the generation of satiety signals.

Device with Flow Reduction Elements, and Embodiments with an Anchoring Member

Figure 2:
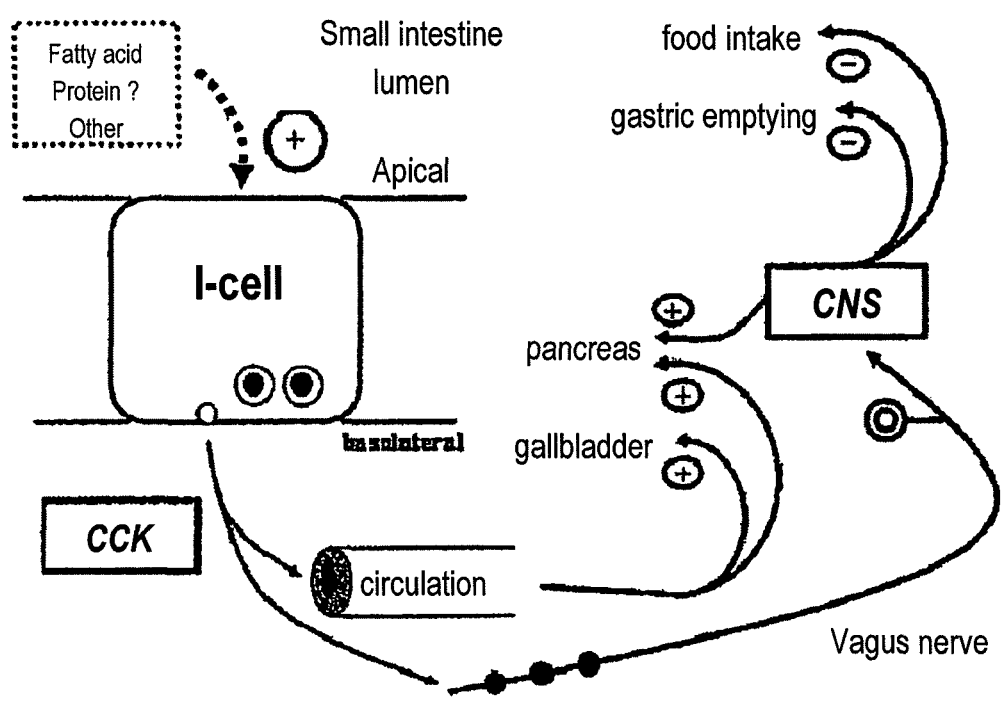
FIG. 2 depicts several exemplary mechanisms through which satiety signals may be generated.

FIG. 2 depicts several exemplary non-limiting mechanisms through which satiety signals may be generated. As shown FIG. 2, a by-product of digestion, such as a fatty acid or other protein, stimulates an L-cell of the small intestine to release CCK locally and into the circulation. CCK released locally may stimulate vagal afferent nerve fibers in the area to generate satiety signals to the central nervous system (CNS). CCK that enters the circulation may travel to the liver to stimulate vagal afferent nerve fibers in the liver to generate satiety signals to the CNS. CCK in the circulation may travel to the gall bladder and pancreas to upregulate the digestion-related activities of these organs. CCK in the circulation also may travel to the CNS itself to contribute to the creation of a satiety signal. Once satiety signals are received and integrated within the CNS, the CNS may trigger physiological effects that serve to contribute to a feeling of fullness and/or the cessation, slowing or reduction of food intake.

Figure 3:
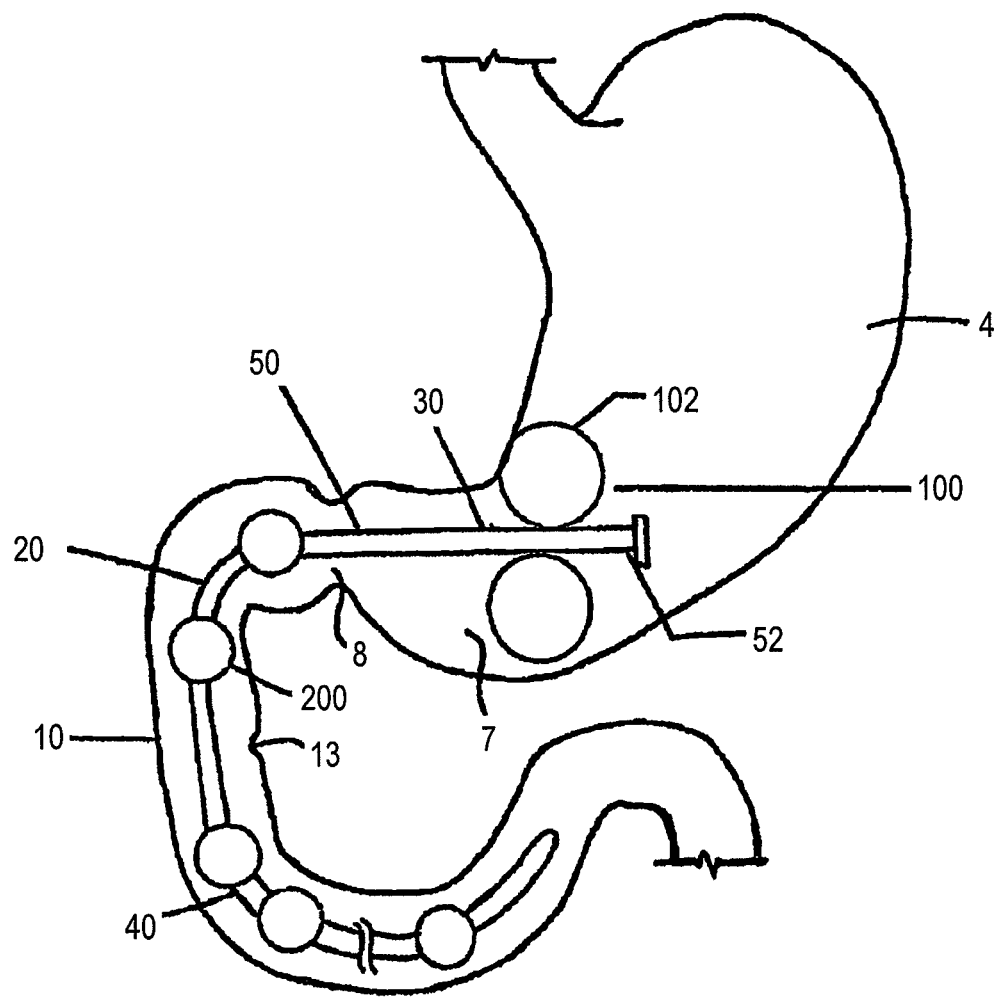
FIG. 3 is a perspective view of one embodiment of a duodenal/small intestinal insert in accordance with the present invention positioned inside the stomach and small intestine.

Turning now to embodiments of the invention, FIG. 3 shows an exemplary small intestinal insert 20 made in accordance with the present invention that may contribute to the creation of satiety signals. The insert 20 is positioned in the stomach 4 and small intestine 10. The insert 20 has a proximal portion 30 and a distal portion 40, and a central tube 50 that extends from the proximal portion 30 to the distal portion 40. One or more flow reduction elements 200 that are sized to fit within the small intestine 10 may be attached to the central tube 50. While not required, the portion of the central tube 50 near the ampulla of Vater 13 generally will not include a flow reduction element 200 so that the introduction of bile and pancreatic fluid into the small intestine is not impeded.

In some embodiments, the central tube 50 has an anchoring member 100 near its proximal end 52, with the anchoring member 100 securing the proximal end 52 of the central tube 50 in the antrum 7 of the stomach. The anchoring member 100 is sized so that it will not pass through the pylorus 8. In this way, embodiments of the present invention including an anchoring member anchor the flow reduction elements 200 within the small intestine. In some embodiments, the anchoring member may be established by one or more inflatable balloons 102 that when inflated are larger than the pylorus 8. The inflatable balloons 102 may be deflated for delivery into the stomach and then inflated inside the stomach. The inflatable balloons 102 may also be deflated for later removal using endoscopic techniques.

As will be described in further detail below, embodiments of flow reduction elements 200 may assume many configurations, and may vary further with regard to physical features such as composition, nature of the surface, and porosity of the bulk material. Some further exemplary embodiments of flow reduction elements 200 are depicted in FIGS. 16-25. In some embodiments, as depicted in FIG. 16, the central tube or member, also referred to as an elongated member, may, itself, be configured into a form that reduces chyme flow in the duodenum. A functional property that embodiments of flow reduction elements have in common is that they slow the transit of digesting food without blocking it, and within clinically appropriate guidelines. The process of slowing the transit rate may also have effects on the composition of the digesting food material, such as varying its biochemical profile with regard to the nutritional compounds being metabolized. Chemical receptors and nerves of the duodenum are sensitive to the biochemical profile of metabolites within the chyme, and participate in the coordination of physiology of digestion and satiety and hunger, accordingly. As such, by altering the flow rate and hence, the biochemical profile of chyme, embodiments of the inventive small intestinal insert contribute to the generation of signals associated with satiety. Flow reduction elements may further effect the composition of the digesting food material by the mixing action the flow reduction elements may provide.

Figure 4:
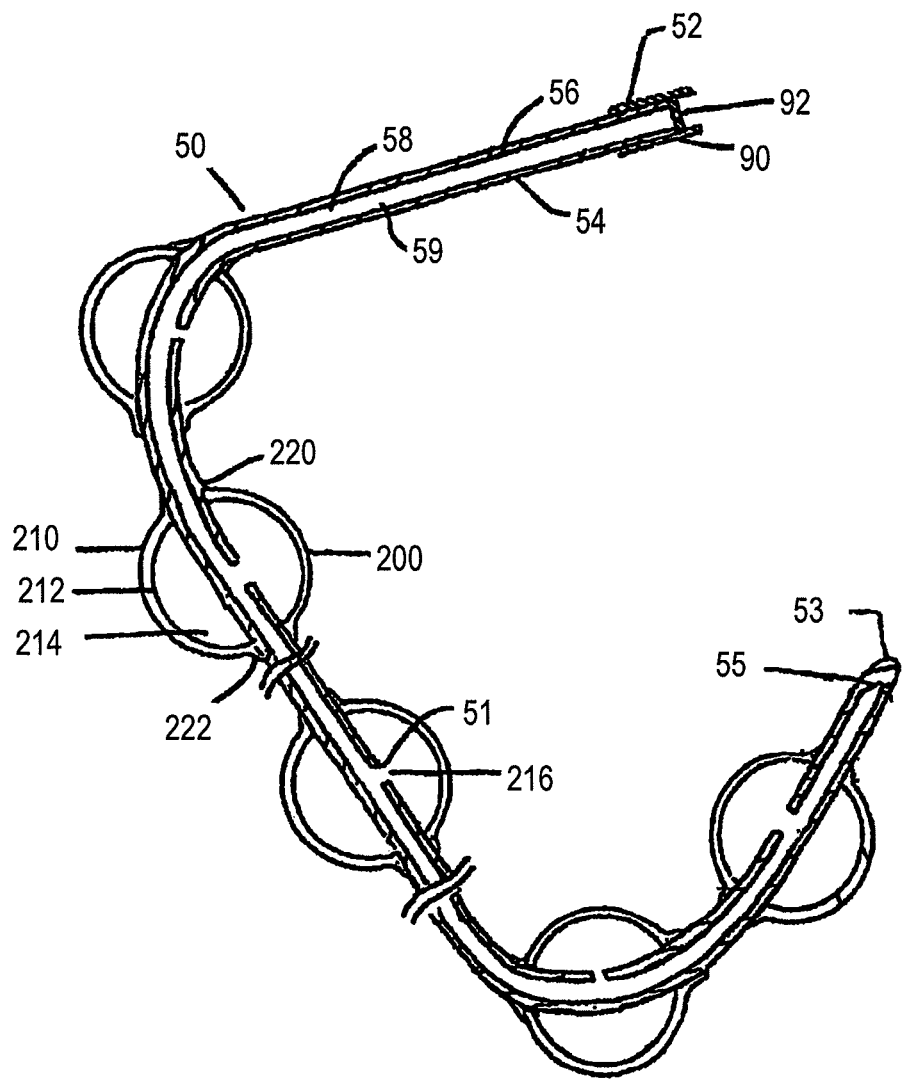
FIG. 4 is a partial section view of a central tube illustrating attached flow reduction elements and a central lumen.

FIG. 4 shows an embodiment of the invention with a central tube 50 that includes an outer wall 54 and an inner wall 56 that define an interior space 58. The interior space 58 forms an inner lumen 59 that may be continuous from the proximal end 52 of the central tube 50 to just short of the distal end 53 of the central tube 50. The distal end 53 of the central tube 50 is sealed at a point 55 so that fluid introduced into the central tube 50 does not leak out distally into the small intestine. In some embodiments a valve 90 may be located substantially at the proximal end of the inner lumen 59. The valve 90 may be a self sealing valve that has a septum 92 that may be accessed by a needle or blunt tip tube for introduction of fluid into the inner lumen 59. The valve 90 also may be accessed so that the fluid inside the inner lumen 59 of the central tube 50 may be aspirated for removal. It is to be understood that the valve type is not limited to a septum type valve only, and that other types of mechanical valves may also be used in place of the septum valve described. Particular embodiments of the present invention are adapted to accept fluids in this manner so that the devices of the present invention may be implanted in a deflated configuration and later expanded into an inflated configuration.

As shown in FIG. 4 and as mentioned above, one or more flow reduction elements 200 may be attached to the central tube 50. In some embodiments the diameter of each flow reduction element 200 may be concentric with the axis of the central tube 50. In the embodiment depicted in FIG. 4, each flow reduction element 200 has an outer wall 210, an inner wall 212, and an inner space 214. At or near its proximally-oriented surface 220 and also at or near its distally-oriented surface 222, each flow reduction element 200 may be attached to the central tube 50 with the inner space 214 of the flow reduction element 200 in fluid communication with the lumen 59 of the central tube 50, such that the inner space 214 surrounds the outer wall 54 of the central tube 50. Each flow reduction element 200 may be attached to the central tube 50 by, for example, adhesives, heat bonding, mechanical restraint or other suitable methods.

As also depicted in FIG. 4, the central tube 50 may be formed with plural inlet/exit ports 216 that are located inside respective flow reduction elements 200. More specifically, each port 216 is formed completely through the central tube wall 51 to establish a pathway for fluid communication between the inner lumen 59 of the central tube 50 and the inner space 214 of the respective flow reduction elements 200. Consequently, the inner lumen 59 of the central tube 50 may be used to introduce fluid into the inner spaces 214 of the flow reduction elements 200 and to inflate the flow reduction elements 200 from a collapsed configuration, in which insertion and removal of the flow reduction elements 200 is facilitated, to an inflated configuration shown in FIG. 4, in which resistance to food passage is increased to induce satiety. Thus, as suggested earlier, the flow reduction element or elements 200 in this embodiment act as balloons that may be deflated and collapsed around the central tube 50 for introduction into the small intestine and then inflated to the desired diameter once in position.

Embodiments of the flow reduction elements may assume other forms, such as coils, ribs, fans, baffles, either peripherally-mounted or centrally-mounted, as well as sleeves, mesh cages or baskets. Embodiments such as these are described further, below, in the section entitled "Further exemplary embodiments of the invention", which also includes description of embodiments with biodegradable components, active biomaterial release mechanisms, and nerve stimulation features, and as depicted in FIGS. 15-31.

In some embodiments, individual flow reduction elements 200 of the present invention may be elastic balloons or inelastic balloons. When an elastic balloon material is used to establish a flow reduction element 200, the flow reduction element 200 inflates to a diameter that is dependent on the volume of fluid introduced into the inner space of the flow reduction element. This embodiment permits adjustment of the balloon size as determined by the physician. If the balloon is too small, for instance, additional fluid could be introduced to enlarge the balloon diameter. Alternatively, if the balloon is too large, additional fluid could be removed to shrink the balloon diameter. It is understood that an alternate embodiment consisting of an inelastic balloon that inflates to a diameter that is independent of a volume of fluid introduced into its inner space is also included within the present invention. The diameter of this type of balloon is fixed when manufactured and does not permit in situ adjustment of the balloon size. However, this type of balloon prevents possible over inflation and rupture if too much fluid is introduced into the balloon.

The flow reduction elements 200 shown in FIG. 4 have the shape of a round sphere. However, other shapes are contemplated and any shape that effectively functions to inhibit the passage of partially digested food in the small intestine is acceptable in accordance with the present invention. It is understood that the ability of the small intestinal insert to remain within the small intestine may be affected by the shape, orientation and tautness of the flow reduction elements 200. For example alternate shapes such as ovoid, elliptical, elongated ellipse and even irregular non-geometrical shapes could be used in accordance with the present invention.

Figure 5:
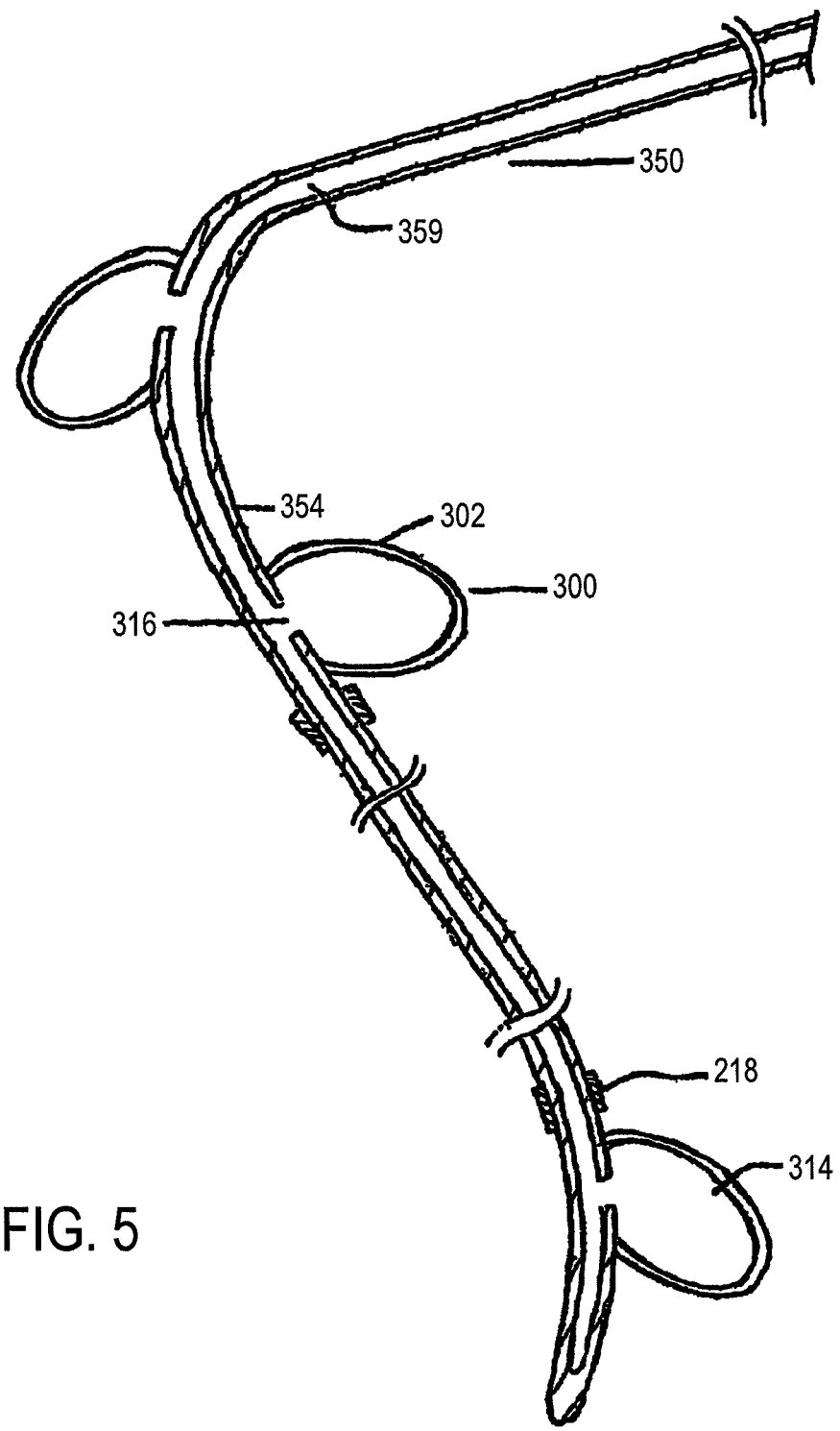
FIG. 5 is a partial section view of a central tube illustrating eccentrically attached flow reduction elements and a central lumen.

FIG. 5 illustrates an alternative embodiment of the present invention in which one or more flow reduction elements 300 are eccentrically attached to a central tube 350. In this embodiment the axis or diameter of the flow reduction element or elements 300 is not concentric with the axis of the central tube. The outer wall 302 of the flow reduction element is attached to the side of an outer wall 354 of the central tube 350. An inner space 314 of each flow reduction element 300 is eccentric relative to the axis of the central tube 350 and is in fluid communication with an inner lumen 359 of the central tube 350 through a respective opening 316. As was the case with the embodiment shown in FIG. 4, in the embodiment shown in FIG. 5 the inner lumen 359 may be used to introduce and remove fluid into the inner space 314 of the flow reduction element 300 to move the flow reduction element 300 between inflated and deflated configurations.

In some embodiments of the present invention, the flow reduction elements 300 may be inflated with a fluid, including a liquid and/or a gas. In some embodiments, the gas may be, for example, air, nitrogen or carbon dioxide. In another embodiment a liquid may be, for example, water or water mixed with other solutions. Any appropriate inflation medium may be modified to deliver bioactive materials or other signals that may diffuse from the insert of the present invention into the small intestine to trigger biological signals of satiety. When bioactive materials are delivered through an inflation medium, the central tube and/or flow reduction elements should be permeable to the bioactive materials. Porosity may be adjusted to control the diffusion rate of the bioactive materials.

When inflating the flow reduction elements of the present invention, it may be important for the physician to monitor the flow reduction element 300 location in the small intestine and the diameter of the flow reduction element relative to the diameter of the small intestine. For this purpose, the flow reduction element may be inflated with a radio opaque fluid that is visible on X-ray. When the flow reduction element contains radio opaque fluid, a physician may non-invasively visualize the size and placement of the flow reduction element(s) from outside the patient's body. This knowledge enables the physician to adjust the size and/or placement of the flow reduction element(s). Likewise radio opaque marker bands 218 as shown in FIG. 5 may be placed around the central tube to facilitate visualization of the central tube's location in the small intestine. The radio opaque marker bands 218 may be placed at predetermined intervals so that the distance inside the small intestine may be used as depth markers and may be measured from outside of the body.

The central tube and flow reduction elements of the present invention may be flexible. In some embodiments, they may be constructed of a polymeric material that may be easily formed or extruded and delivered with the aid of an endoscope by known techniques. A central tube 50 that is soft and flexible will contour to the anatomy of the gastrointestinal tract and provide less irritation of the stomach and intestinal lining.

Figure 6:
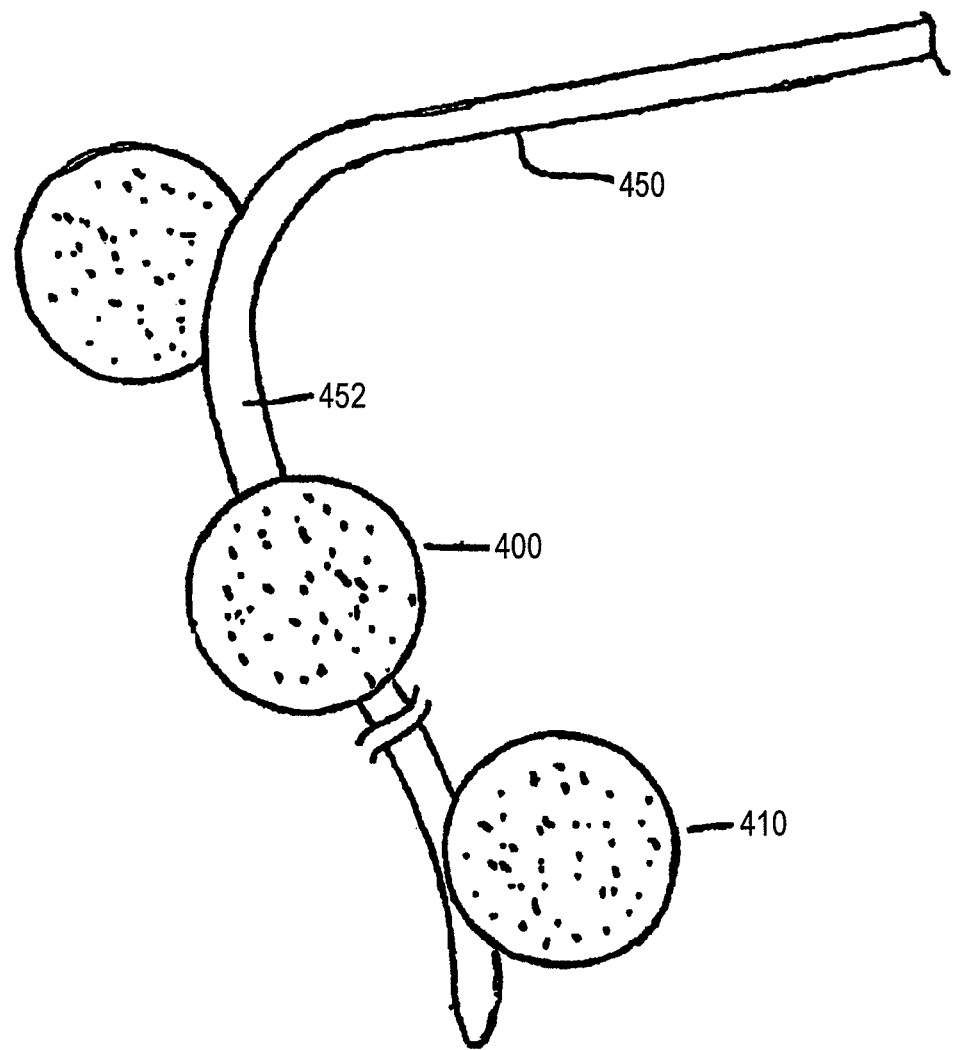
FIG. 6 is a perspective view of an alternative embodiment showing an elongated member and illustrating attached flow reduction elements.

FIG. 6 shows an alternative embodiment of the invention with flow reduction elements that are generally self-expanding, and do not necessarily include a central lumen. These embodiments include a central shaft 450 around which flow reduction elements are concentrically attached 400 and/or are eccentrically attached 410. The elements 400 and 410 may be attached to the central shaft 450 by, for example, heat fusing, adhesives or other suitable methods as known in the art. These flow reduction elements 400 may be made from material that may be folded or collapsed to a first volume suitable for insertion with the aid of an endoscope and then may self expand to a second volume suitable for restricting the flow of partially digested food according to the present invention. These flow reduction elements may be made from materials, or materials may be configured so as to take the form of such as, by way of example, a sponge, a foam, a hydrogel, or springs that may be compacted into a small volume and then self expand to a pre-determined shape and volume when unrestricted. Gel- or sponge-based embodiments may include open cell or closed cell forms. In addition to having features that allow such gel- or sponge-based embodiments to be collapsible and expandable for deployment, such embodiments typically have a high surface area which is beneficial in embodiments that may include bioactive agents, and may further be conducive for purposes of biodegradability. Another foam-related embodiment is described below in the section entitled "Further embodiments of the invention", and depicted in FIG. 21. Because the flow reduction elements self expand, the need for an inflation system is eliminated and this embodiment represents a simple mechanical design. These flow reduction elements may also be impregnated with bioactive materials or other signals that may trigger biological signals of satiety.

The central shaft 450 of an embodiment such as that depicted in FIG. 6 may be solid and without an inner lumen or inner space. In another embodiment the central shaft 450 may include a passageway for consumed food so that the food may pass through the small intestine without being fully absorbed.

Figure 7:
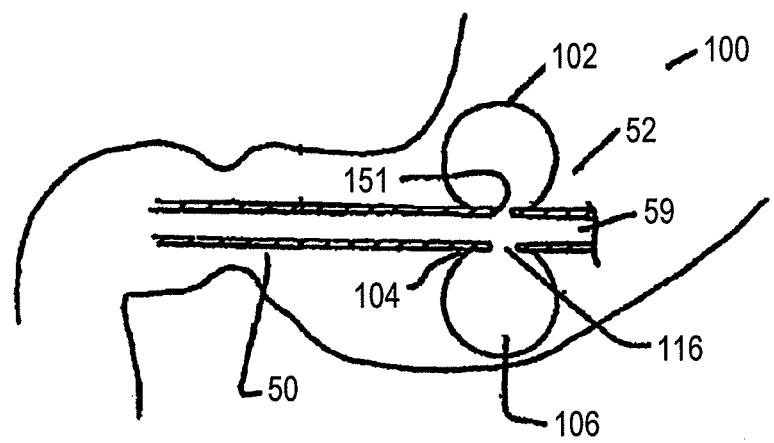
FIG. 7 is a perspective section view of a central tube and an anchoring member.

Turning now to various anchoring members that may be used in accordance with the present invention, FIG. 7 depicts one such member. In FIG. 7, the central tube 50 has an anchoring member 100 near its proximal end 52. As stated earlier, the anchoring member 100 may be established by one or more inflatable balloons 102. These balloons 102 may be eccentrically attached to the central tube at point 104 near the proximal end 52 of the central tube 50. These balloons may be formed in many shapes and are not limited to the spherical shape shown. The central tube may be formed with an opening 116 for each respective balloon 102 so that a pathway for fluid communication is established between the inner lumen 59 of the central tube 50 and the inner space of each balloon 106. The inner lumen 59 is used to introduce fluid into the inner space of the balloon 106 and inflate the balloon 102 from a first volume in a collapsed state to a second volume or inflated state.

When the one or more balloons 102 of the anchoring member 100 are fully inflated, they secure the proximal end of the central tube 52 within the antrum of the stomach. The one or more inflatable balloons 102 have a combined cross sectional diameter greater than the diameter of the pyloric valve to prevent migration across the pylorus. The inflatable balloons 102 may be inflated and deflated by adding or removing fluid from the central tube inner lumen 59. The inflatable balloons 102 may be connected to the same central tube inner lumen 59 as the one or more flow reduction elements attached to the central tube and may be inflated simultaneously with the flow reduction elements. The central tube 50 may also have more than one inner lumen so that the inflatable balloons 102 and individual one or more flow reduction elements may be inflated and deflated independently as well.

Figure 8:
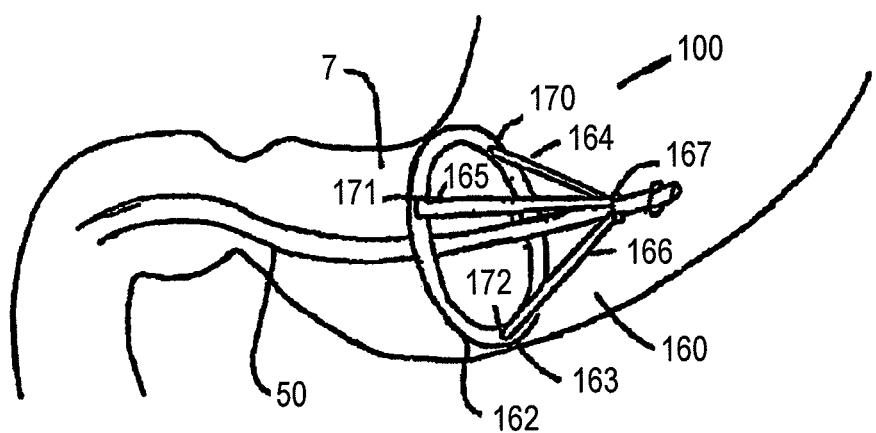
FIG. 8 is a perspective view of an alternative embodiment of a central tube and an anchoring member.

FIG. 8 illustrates another embodiment of the invention, wherein an anchoring member 100 of the present invention is deployed in the antrum 7. In this embodiment, a central tube 50 is attached to an inverted umbrella skeleton 160. This skeleton 160 has a ring 162 that surrounds the central tube 50 and is supported by struts. In the depicted embodiment the ring 162 is supported by three struts 164, 165, and 166, however more or fewer struts may be successfully employed. In the embodiment depicted in FIG. 8, the struts are joined together at the central tube 50 at point 167 and attached to the ring 162 at points 170, 171 and 172. The ring 162 of this anchor configuration may be made from, by way of example, flexible plastic material or flexible wire and has a diameter significantly larger than the diameter of the pyloric valve. This umbrella skeleton 160 may be collapsed around the central tube 50 for insertion into the stomach with the aid of an endoscope. As the device is released from the endoscope, the umbrella skeleton 160 may spring out and assume a configuration similar to that shown in FIG. 8. The struts 164, 165 and 166 may be made from, by way of example, plastic, metal or from plastic covered metal. The edge of the ring which is in contact with the antrum walls 163, may be constructed to assist in securing the umbrella ring 162 to the walls of the antrum.

Device Embodiments without an Anchoring Member

Figure 9:
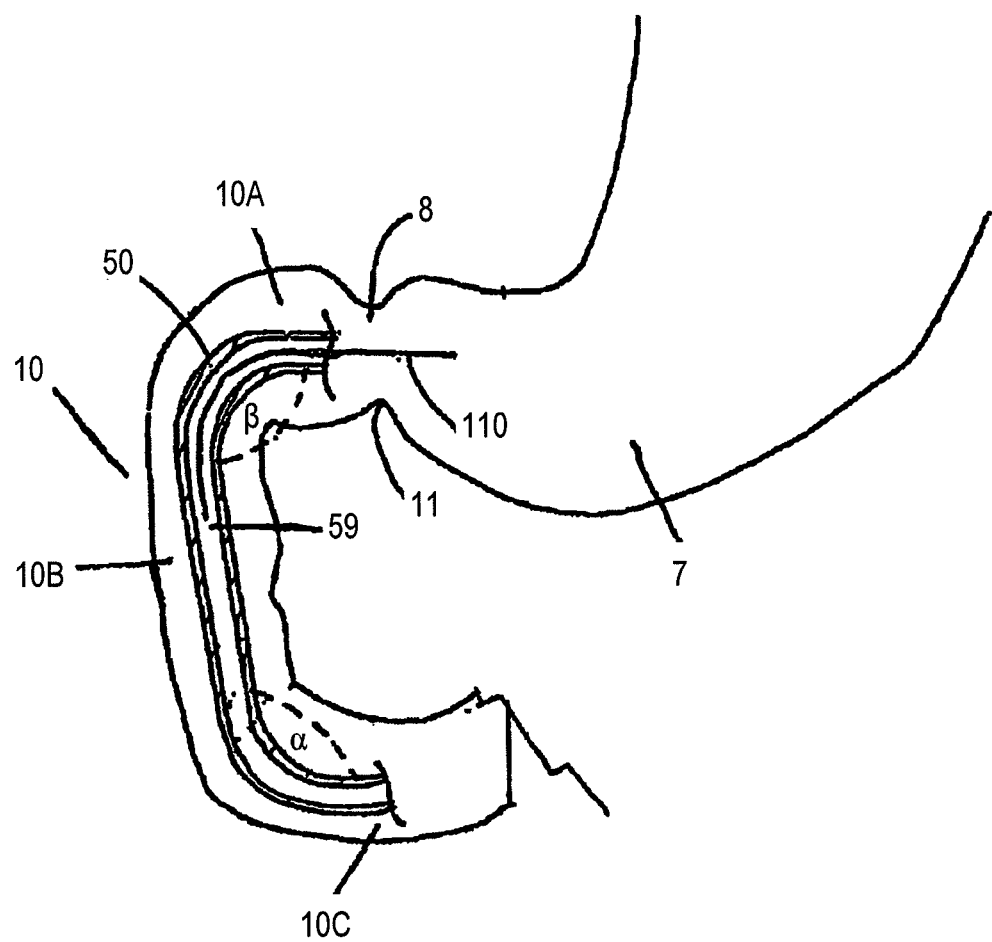
FIG. 9 is a section view of a central tube of the present invention that may lodge in the small intestine for a period of time without any anchoring to the stomach or pylorus.

FIG. 9 shows a central tube or elongated member 50 of the present invention that may lodge and remain in the small intestine for a period of time without any anchoring to the stomach or pylorus. Embodiments of the present invention that can lodge and remain within the small intestine for a period of time without any anchoring to the stomach or pylorus do so by (i) adopting a central tube with appropriately placed angles or curvilinear portions that mimic the contours of the small intestine; and (ii) flow reduction elements of an appropriate diameter that help to hold the intestinal insert in place. This particular section of the description focuses on angled sections, as exemplified by FIG. 9. Details and particulars of angles are described further below, in the context of illustrative example depicted in FIGS. 29 and 30.

In FIG. 9, the first three parts of the duodenum, including the duodenal bulb 10A, the vertical duodenum 10B, and the horizontal duodenum 10C are depicted. The flow reduction elements of the depicted embodiment have been removed for clarity. Distal to the pylorus 8 and immediately after entering the duodenum 10, the central tube 50 may assume a sharp bend of radius $\beta$ between the duodenal bulb 10A and the vertical duodenum 10B, and a sharp bend of radius a between the vertical duodenum 10B and horizontal duodenum 10C. In some embodiments the radius $\beta$ and the radius $\alpha$ may be between about 45 degrees and about 110 degrees. In another embodiment the radius $\beta$ and the radius a may be between about 60 degrees and about 100 degrees such that the central tube 50 bends to follow or correspond to the inner lumen of the duodenum 10 at these locations that contain predictably configured bends. In another embodiment the radius $\beta$ and the radius a may be about 80 degrees. While most embodiments of the present invention will include lengths that require adoption of angle $\beta$ and angle $\alpha$, shorter devices adopting one or the other are also included within the scope of the present invention. In these described embodiments of the present invention, it may be advantageous that the central tube 50 be flexible enough to conform to the sharp angulations of the small intestine to avoid kinking. One or more flow reduction elements with a diameter about equal to that of the small intestine are also included along the length of the central tube 50. In some embodiments, this diameter is about 3 cm; in other embodiments this diameter is about 4 cm.

To stabilize an intestinal insert in situ without the need for an anchoring element, the central tube or elongated member 50 may be pre-formed with a configuration that conforms to the duodenal angulations prior to insertion in the body. This embodiment of the present invention may be constrained in a straight configuration by a stiffening rod 110 placed down the inner lumen 59 of the central tube 50 as shown. This stiffening rod 110 may be placed into a separate lumen designed to house this stiffening rod or may be imbedded in the wall of the central tube 50. Upon insertion into the patient with the aid of an endoscope, when the central tube 50 reaches the location of the sharp bends in the duodenum 10, the stiffening rod 110 may be withdrawn, thereby allowing the central tube 50 to assume a pre-formed shape.

In another embodiment that stabilizes in situ without an anchoring member, the central tube or elongated member 50 may have a shape memory alloy wire embedded inside the central tube wall 51 or residing in the inner lumen 59. This shape memory alloy wire has a pre-set bend configuration with a radius $\beta$ and $\alpha$ radius a that matches or corresponds to the bend configuration of the duodenum and is positioned at the central tube 50 at the corresponding location. Upon insertion into the patient with the aid of an endoscope, when the central tube 50 reaches the location of the sharp bend in the duodenum 10 and the shape memory alloy wire reaches a pre-set transition temperature equal to body temperature or about 37° C., the wire assumes the programmed shape and forces the central tube 50 and the central tube wall 51 to assume the same shape.

In another embodiment, the central tube or elongate member 50 may have a spring embedded inside the central tube wall 51 or inner lumen 59. This spring could be pre-shaped to the anatomy of the wall of the small intestine. The spring is held straight during delivery and conforms to the small intestine anatomy after release, and such shape enables the device to remain in place. The shape enables the device to remain in place. In one embodiment, due to its configuration that matches or corresponds to the predictable placement and configuration of the small intestine, the device can remain in place for a period of time within the small intestine without anchoring to the stomach or pylorus of the stomach.

While the present embodiments of the present invention can remain in the small intestine for a period of time without anchoring to the stomach or pylorus, they are not intended to remain indefinitely. In some embodiments, the inserts are endoscopically removed after a predetermined period of time. In other embodiments, the inserts may be formed of one or more biodegradable materials that are eventually degraded and eliminated from the body. The rate of biodegradability of any embodiment of the inventive device may be adjusted by varying the biodegradable aspects of the embodiment, thus allowing for a manufacturing route to control the residency time in the intestinal tract to a clinically appropriate level. Biodegradable composition may be varied in qualitative terms, by varying the composition of the materials. Biodegradability of devices may also be varied in quantitative terms, for example by varying the quantity of material at a location vulnerable to biodegradation. For example, varying the thickness of a junction designed for biodegradable vulnerability may be varied in thickness.

Biodegradable aspects of embodiments of the invention are described further below; all embodiments described herein, and all embodiments as depicted in FIGS. 3-12, and 16-31 may have portions that include biodegradable materials, both within the central tube or member, also referred to synonymously as elongate member 50 and/or any of the various embodiments of the chyme flow reduction elements 200. Exemplary processes of biodegradation are depicted, for example in FIGS. 27A-28B. In the description that ensues, some embodiments are used as specifically illustrative examples that are formed wholly or in part from biodegradable materials, but, as stated, all embodiments may include biodegradable materials, even when not specifically identified as such, including embodiments with and without an anchoring member.

Deployment of Inserts and Flow Reduction Elements

Figure 10:
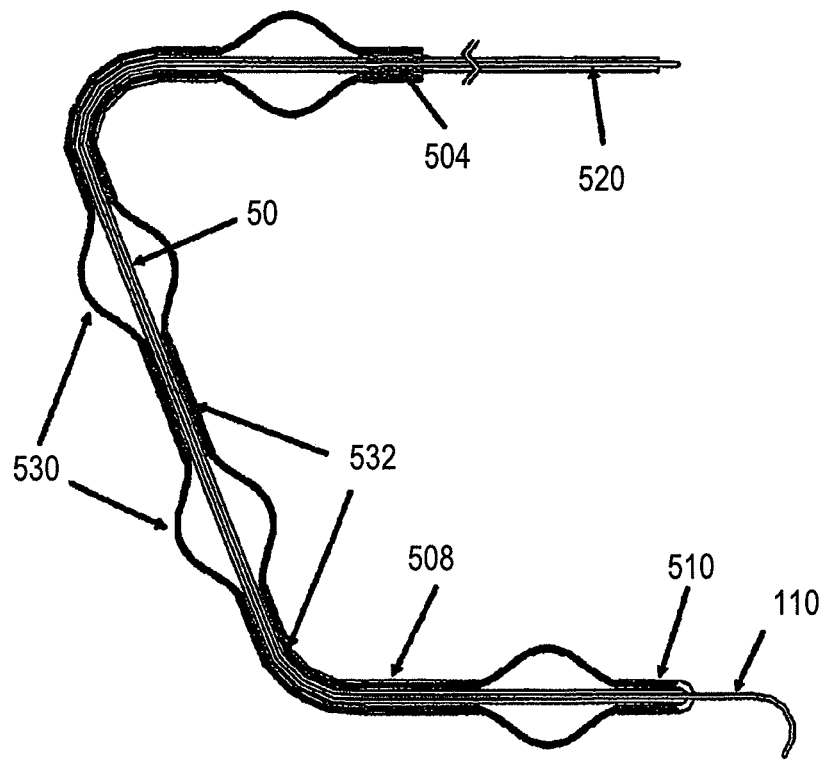
FIG. 10 illustrates a central tube attached to an expandable sleeve, the expandable sleeve allowing expansion of particular segments of the central tube to form flow reduction elements.

The description now turns to considerations related to deployment of the inventive insert, some embodiments of which include flow reduction elements. Flow reduction elements are referenced in a generic sense with the label 200, but some exemplary embodiments make use of different label numbers, for their particular features. FIG. 10 illustrates an embodiment of the present invention where flow reduction elements may be created through the expansion of portions of an expandable sleeve; this embodiment will be used in the context of describing an example of how to deploy a device with flow reduction elements. In the embodiment depicted in FIG. 10, a central tube 50 is attached to an expandable sleeve 508 at the expandable sleeve's distal end 510 near the distal portion of a duodenal/small intestinal insert of the present invention. In a delivery configuration of the depicted embodiment, the opposite proximal end of the central tube 50 is attached to a detachable extension tube 520 that may lock onto a proximal portion of the central tube 50 when the flow reduction elements 530 are expanded (post delivery). One non-limiting method of detachable attachment is the use of one or more screws 504, whereby the extension tube 520 screws into the central tube 50. The central tube 50 may be pre-formed to have a configuration that conforms to the anatomy of the duodenum 10 shown in FIG. 1. A central tube 50 so described would force the expandable sleeve 508 to assume the configuration of the central tube 50. The central tube 50 may be constructed, merely by way of example, of wire, spring, superelastic or shape memory alloys, hollow steel tubing or plastic polymers. In some embodiments a stiffening rod or guide wire 110 may also be inserted through the lumen of central tube 50.

The expandable sleeve 508 herein described is designed to expand at predefined segments to allow the formation of flow reduction elements 530. In some embodiments, the non-expanded segments 532 of expandable sleeve 508 may be coated with a polymer to prevent their expansion. In another embodiment, the flow reduction elements 530 may be covered with a flexible polymer to prevent partially digested food from entering the flow reduction elements 530. In another embodiment, a stiffening rod or guide wire 110 may be inserted through the lumen of central tube 50 to straighten the central tube 50 when the device is delivered into the duodenum.

The expandable sleeve 508 may, merely by way of example be configured as any one or more of a knit, a weave, a mesh or a braid that may be formed, merely by way of example from any one or more of a metal, a wire, a ribbon, a plastic polymer or a biodegradable material.

Figure 11:
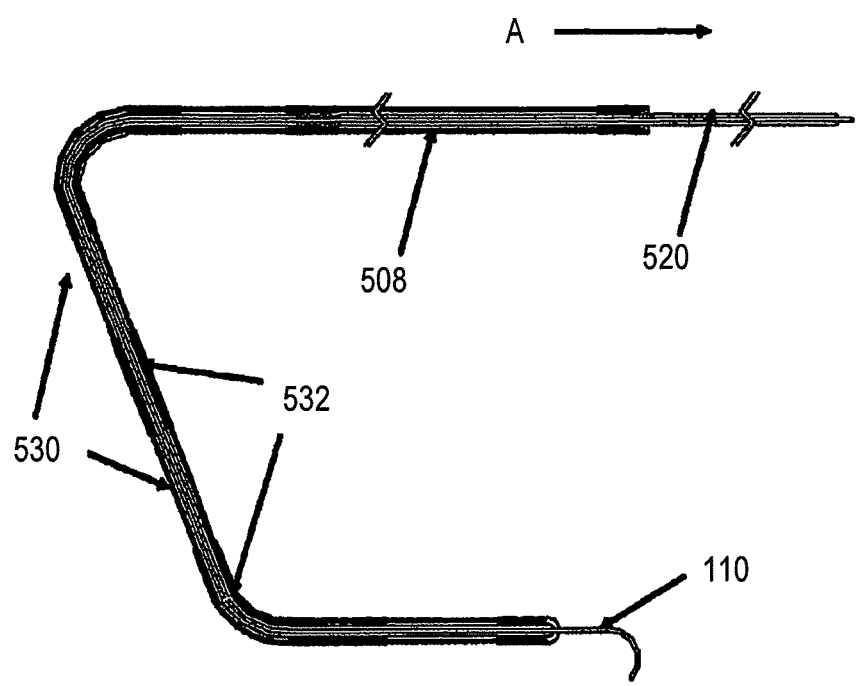
FIG. 11 illustrates an expandable sleeve in a collapsed configuration for insertion into the small intestine.

FIG. 11 illustrates the expandable sleeve 508 consisting of flow reduction elements 530 in a collapsed configuration for insertion into the small intestine. In this configuration a force A is applied to the expandable sleeve 508 to collapse the flow reduction elements 530. The collapsed form may be restrained by a constraining mechanism such as, merely by way of example, a sheath or a tightly wound string, or by applying sustained traction on the proximal end of the expandable sleeve 508. FIG. 11 also shows portions of the central tube that will remain unexpanded 532, a detachable extension tube 520 and a guidewire 110.

The expansion of the flow reduction elements 530 in the embodiments depicted in FIGS. 10 and 11 may occur passively or actively. One example of passive expansion may be the removal of a constraining mechanism to allow the flow reduction elements 530 to expand to an original expanded state. Another non-limiting mechanism can be to release traction on the proximal end of an expandable sleeve 508 to allow the flow reduction elements 530 to expand to an original expanded state.

The flow reduction elements 530 of the embodiments depicted in FIGS. 10 and 11 can expand in a distal to proximal fashion, a proximal to distal fashion or in a central fashion depending on their relative position in relation to, in some embodiments, motion of the expandable sleeve 508 and the central tube 50 to one another. For example, if the proximal end of the flow reduction element lumen is held in the duodenal bulb and the central tube 50 is pulled back, the distal end of the flow reduction element lumen may expand first. Expansion in this direction may be advantageous because the position of the proximal end of the flow reduction element lumen remains in the duodenal bulb.

Figure 12:
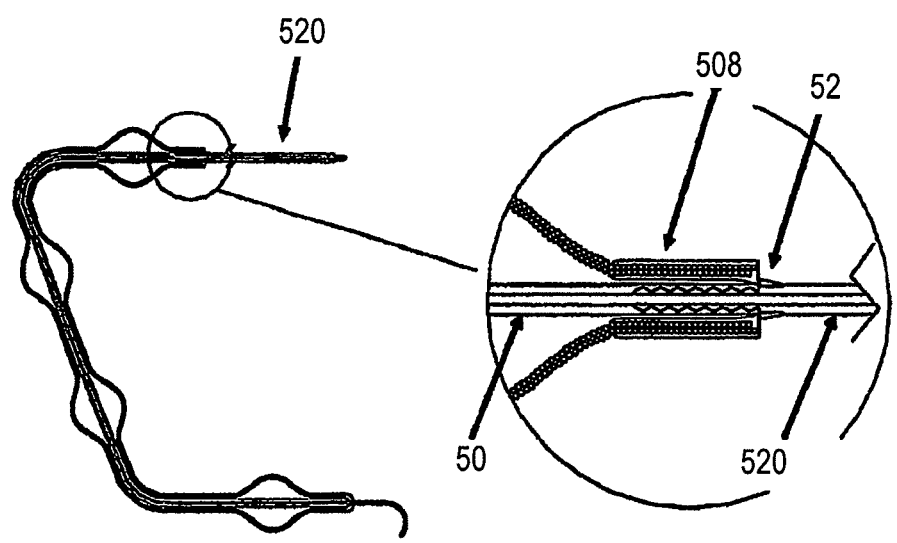
FIG. 12 illustrates one mechanism for keeping flow reduction elements formed with an expandable sleeve in a desired expanded configuration.

FIG. 12 illustrates some embodiments of the present invention that may lock the proximal end of the expandable sleeve 508 to the central tube 50 at a position to keep the flow reduction elements in a desired expanded configuration. Traction on the extension tube 520 retracts central tube 50 until wedge 52 engages the proximal end of the expandable sleeve 508. The central tube 50 may have multiple ratchet-like wedges that may lock the expandable sleeve 508 at different degrees of expansion. The extension tube may be unscrewed from the central tube 50 after deployment of the device and expansion of the expandable sleeve 508.

Biodegradable Features

While the present embodiments of the present invention may remain in the small intestine for a period of time, they are not intended to remain indefinitely. In some embodiments, the inserts are endoscopically removed after a predetermined period of time. In other embodiments, the inserts may be formed or partially-formed of one or more biodegradable materials that are eventually degraded and eliminated from the body. In some embodiments, the device may include some material that is biodegradable and some material that is not biodegradable. In some embodiments that include non-biodegradable materials, the degradation of the biodegradable portions of the device may facilitate the breakdown and eventual elimination of the non biodegradable portions.

Biodegradable is used in a broad sense, so as to include the any type of material breakdown or disintegration of any type that may occur in a biological environment, such environment being defined primarily by the biological host, but also by any microorganisms within the host. Other terms that biodegradability broadly embraces include bioabsorbability and bioerodibility. Biodegradation, per embodiments of the invention, may occur, for example, by dissolution, by effects of pH, such as action of acids, by hydrolytic mechanisms, by hydration, by digestive or enzyme-catalyzed effects such as cleavage, or by physical effects of bodily or muscular movement. An example of biodegradation is provided by the hydrolysis, dissolution, or reaction to pH, or enzymatic lysis that results in a scission of the polymer backbone of an inserted device. Microorganisms such as those that reside in the intestine, may eat or digest polymers, and also initiate a mechanical, chemical, or enzymatic aging. The biodegradable materials of embodiments of the invention are also biologically compatible, as well as are breakdown products of biodegradable materials, as included in embodiments of the present invention. Biodegradable materials may include organic and inorganic compounds. Some representative inorganic compounds are described below in the section related to "device features to accommodate bioactive agents"; in this section, a description of biodegradable polymers is provided for inclusion as embodiments of the present invention.

Figure 27A:
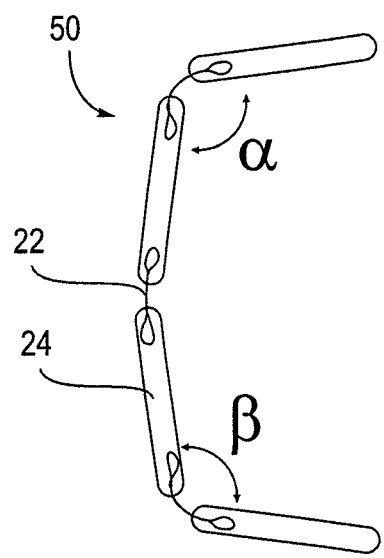
FIG. 27A shows the central member in an intact configuration.
Figure 27B:
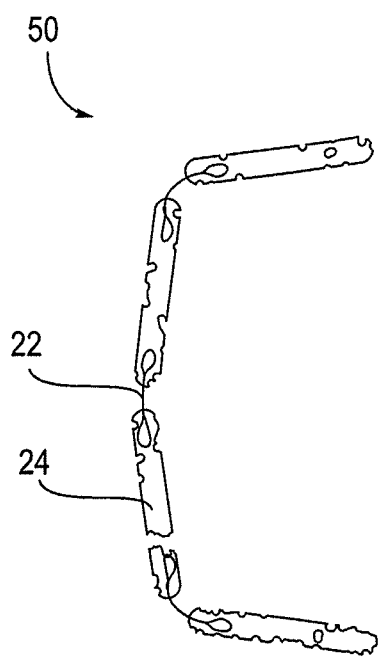
FIG. 27B shows the central member after biodegradation.
Figure 28A:
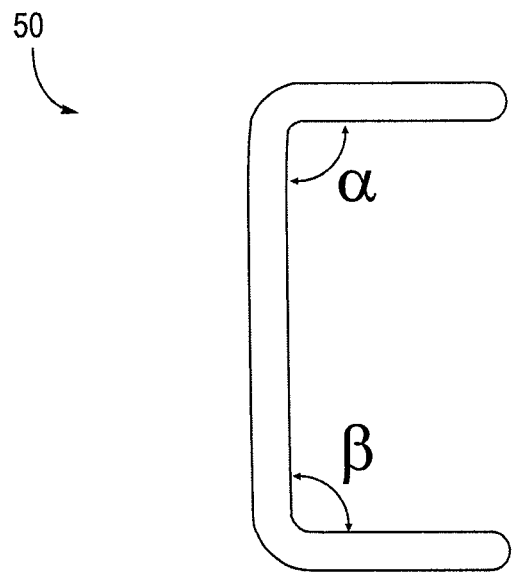
FIG. 28A shows the central member in an intact configuration.
Figure 28B:
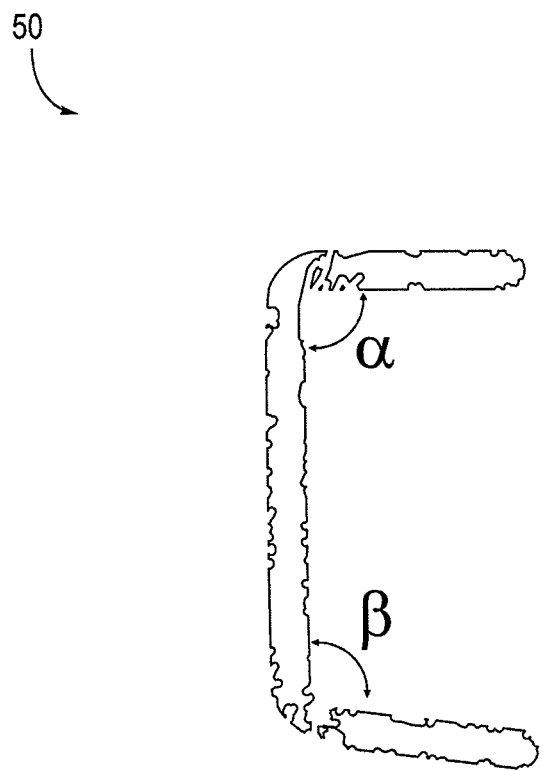
FIG. 28B shows the central member after biodegradation.

As mentioned above, some embodiments of the invention may include a resilient shape holding portion, and in some embodiments, a shape memory portion that supports the maintenance of an advantageous configuration of the device, particularly with regard to maintenance of angles alpha and beta of the inventive C-shaped duodenal insert device. Metals as well as some polymers are capable of resiliently holding a shape. Shape memory materials include metal alloys as well as biodegradable polymers. Shape memory alloy elements of the device are not biodegradable, but these alloy structural elements may be combined or joined with polymeric elements that are biodegradable, and upon such degradation, the alloy elements are released in a form that allows their elimination. Such embodiments are depicted in FIGS. 27A and 27B, as described below. Other embodiments or the invention may include biodegradable shape memory polymeric elements. Biodegradable shape memory polymers have been described in various publications, including U.S. Pat. No. 6,160,084, U.S. Pat. No. 6,281,262, U.S. Pat. No. 6,388,043, U.S. Pat. No. 6,720,402, and US Published Applications US 20050075405A1, US 20030055198A1, US 20040015187A1, US 20040110285A1, US 20050245719A1, and US 20060142794A1. Embodiments of the invention may include any one or more of such shape memory materials, and further, such materials may be joined together in various ways as depicted in FIGS. 28A and 28B.

A variety of natural, synthetic, and biosynthetic polymers are biologically degradable and may be included as materials that comprise embodiments of the intestinal insert device. A polymer based on the C-C backbone tends to be nonbiodegradable, whereas heteroatom-containing polymer backbones confer biodegradability. Biodegradability may be engineered into polymers by the judicious addition of chemical linkages such as anhydride, ester, or amide bonds, among others. The mechanism for degradation is by hydrolysis or enzymatic cleavage resulting in a scission of the polymer backbone. Microorganisms, such as those that reside in the intestine, may eat or digest polymers, and also initiate a mechanical, chemical, or enzymatic aging.

Biodegradable polymers with hydrolyzable chemical bonds are appropriate as materials for a biodegradable intestinal insert. In addition to being biocompatible, the material should meet other criteria, for example, being processable, sterilizable, and capable of controlled stability or degradation in response to biological conditions. The degradation products often define the biocompatibility of a polymer, not necessarily the polymer itself. Poly(esters) based on polylactide (PLA), polyglycolide (PGA), polycaprolactone (PCL), and their copolymers have been extensively employed as biomaterials. Degradation of these materials yields the corresponding hydroxy acids, making them safe for in vivo use.

Other biodegradable polymers include poly(hydroxyalkanoate)s of the PHB-PHV class, additional poly(ester)s, and natural polymers, particularly, modified poly(saccharide)s, e.g., starch, cellulose, and chitosan. Chitosan is derived from chitin, and is the second most abundant natural polymer in the world after cellulose. Upon deacetylation, it yields the novel biomaterial Chitosan, which upon further hydrolysis yields an extremely low molecular weight oligosaccharide. Chitosan is biocompatible, antibacterial and environmentally friendly polyelectrolyte, thus appropriate for medical devices and as material for controlled release in drug delivery.

Poly(ethylene oxide), PEO, a polymer with the repeat structural unit —$CH_2CH_2O$—, has applications in drug delivery. The material known as poly(ethylene glycol), PEG, is in fact PEO but has in addition hydroxyl groups at each end of the molecule. In contrast to high molecular weight PEO, in which the degree of polymerization, n, might range from $10^3$ to $10^5$, the range used most frequently for biomaterials is generally from 12 to 200, that is PEG 600 to PEG 9000, though grades up to 20,000 are commercially available. Key properties that make poly(ethylene oxide) attractive as a biomaterial are biocompatibility, hydrophilicity, and versatility. The simple, water-soluble, linear polymer may be modified by chemical interaction to form water-insoluble but water-swellable hydrogels retaining the desirable properties associated with the ethylene oxide part of the structure.

Multiblock copolymers of poly(ethylene oxide) (PEO) and poly(butylene terephthalate) (PBT) may also be appropriate for intestinally inserted devices. These materials are subject to both hydrolysis (via ester bonds) and oxidation (via ether bonds). Degradation rate is influenced by PEO molecular weight and content. Additionally, the copolymer with the highest water uptake degrades most rapidly.

A widely used nondegradable polymer is ethylene-vinyl acetate copolymer. This copolymer has excellent biocompatibility, physical stability, biological inertness, and processability. In drug delivery application these copolymers usually contain 30-50 weight percent vinyl acetate. Ethylene-vinyl acetate copolymer membrane acts as the rate-limiting barrier for the diffusion of the drug. In the Type II class of degradable polymers, the conversion of the hydrophobic substituents to hydrophilic side groups is a first step in the degradation process. The tyrosine-derived polycarbonate poly(DTE-co-DT carbonate), may, for example, be an appropriate material for a biodegradable intestinal insert. The material may be made with the pendant group via the tyrosine as either an ethyl ester (DTE) or free carboxylate (DT). Through alteration of the ratio of DTE to DT, the material's hydrophobic/hydrophilic balance and rate of in vivo degradation may be manipulated.

Water-swellable polymer networks may function as hydrogels at one end or as superabsorbers at the other extreme. Hydrogels are characterized by the pronounced affinity of their chemical structures for aqueous solutions in which they swell rather than dissolve. Such polymeric networks may range from being mildly absorbing, typically retaining 30 wt. % of water within their structure, to superabsorbing, where they retain many times their weight of aqueous fluids. Several synthetic strategies have been proposed to prepare absorbent polymers including: polyelectrolyte(s) subjected to covalent cross-linking, associative polymers consisting of hydrophilic and hydrophobic components ("effective" cross-links through hydrogen bonding), and physically interpenetrating polymer networks yielding absorbent polymers of high mechanical strength. These approaches are not mutually exclusive, and materials may include composite gels that are critically reliant on the balance between polymer-polymer and polymer-solvent interactions under various stimuli including changes in temperature, pH, ionic strength, solvent, concentration, pressure, stress, light intensity, and electric or magnetic fields.

Bioactive Materials Deliverable by Embodiments of the Device

As previously stated, in some embodiments, the central tube and/or flow reduction elements of the invention may be adapted to release bioactive materials or bioactive agents that trigger biological satiety signals. In some embodiments, the one or more of the flow reduction elements and/or central tube may be a porous and malleable solid designed to release a signal into the gastrointestinal (GI) tract over time. In some embodiments, nutrient products of digestion are released from the one or more flow reduction elements 200 and/or central tube or elongate member 50 to trigger chemoreceptors within the GI tract to release molecular signals involved in transmitting and/or creating satiety signals.

The description now turns to a consideration of release of bioactive materials from the device in furtherance of reducing appetite or slowing food absorption or intake. The term "bioactive material(s)" refers to any organic, inorganic, or living agent that is biologically active or relevant; the term has been extensively described in U.S. application Ser. No. 11/300, 283, and will described here only briefly. For example, a bioactive material may be a protein, a polypeptide, a polysaccharide (e.g. heparin), an oligosaccharide, a mono- or disaccharide, a lipid, an organ metallic compound, or an inorganic compound, an antimicrobial agent (including antibacterial and anti-fungal agents), an anti-viral agent, anti-tumor agent, immunogenic agent. It may include a living or senescent cell, a stem cell, a bacterium, a virus, or any part thereof. It may include a biologically active molecule such as a hormone, a growth factor, a growth factor-producing virus, a growth factor inhibitor, a growth factor receptor, an anti-inflammatory agent, an ant metabolite, or a complete or partial functional insense or antisense gene. It may also include a man-made particle or material that carries a biologically relevant or active material. A bioactive material also may be a by-product of digestion or an agent that alters the pH of its surrounding environment.

Bioactive materials also may include drugs such as chemical or biological compounds that can have a therapeutic effect on a biological organism. Bioactive materials also may include precursor materials that exhibit the relevant biological activity after being metabolized, broken-down (e.g. cleaving molecular components), or otherwise processed and modified within the body. Combinations, blends, or other preparations of any of the foregoing examples may be made and still be considered bioactive materials within the intended meaning herein. Aspects of the present invention directed toward bioactive materials may include any or all of the foregoing examples.

Examples of bioactive materials included with the present invention include hormones and other compounds that convey satiety promoting signals. Bioactive materials of the present invention may also include other naturally-occurring or synthesized peptide, protein, and steroid hormones. Bioactive agents further may include anti-tumor agents, antimicrobial agents, such as antibiotics: cephalosporins: aminoglycosides:; macrolides: tetracyclines, chemotherapeutic agents, sulfonamides, urinary tract antiseptics, anaerobic infection antibiotics, drugs for tuberculosis, drugs for leprosy, antifungal agents, antiviral agents, chemotherapeutic agents for amebiasis, anti-helminthiasis agents, anti-inflammatory agents, anti-gout agents, centrally acting analgesics, thyroid drugs, including those used in adjunctive therapy, and those used as anti-thyroid agents, viral surface antigens or parts of viruses, bacterial surface antigens or parts of bacteria, surface antigens of parasites causing disease or portions of parasites, immunoglobulins, antitoxins, and antigens that elicit an immune response, such as disease-associated antigens, or bioactive agents such as hormones, enzymes or clotting factors:

Device Features to Accommodate Bioactive Agents for Delivery

The central tube 20 and/or flow reduction elements 200 of the present invention may have bioactive materials adhered to their surface (through dip-coating, spray-coating, sputter-coating and a variety of other techniques known to those of skill in the art) or included in reservoirs or depots accessible to the surface, or may be manufactured so that the materials making up the intestinal insert include and diffuse such bioactive materials. The central tube and/or flow reduction elements of the present invention that diffuse bioactive materials, may be created by a number of different procedures that are referenced in U.S. application Ser. No. 11/300,283 of Binmoeller, filed on Dec. 15, 2005 and published as U.S. Publication 2006/0178691 on Aug. 10, 2006, including references to U.S. Pat. No. 5,019,400 to Gombotz et al. U.S. Pat. No. 6,685,957 to Bezemer et al. and U.S. Pat. No. 6,685,957.

When a hydrophobic bioactive material, such as a steroid hormone is incorporated by the above-described method, at least one hydrophobic antioxidant may be present. Hydrophobic antioxidants which may be employed include, tocopherols (such as α-tocopherol, β-tocopherol, γ-tocopherol, δ-tocopherol, epsilon-tocopherol, $zeta_1$-tocopherol, $zeta_2$-tocopherol, and eta-tocopherol) and 1-ascorbic acid 6-palmitate. Such hydrophobic antioxidants may retard the degradation of the copolymer and retard the release of the bioactive material.

When a loaded polymer made according to the above-referenced technique includes a hydrophilic bioactive material, the loaded polymer may also include, in addition to a hydrophobic antioxidant, a hydrophobic molecule such as, by way of example, cholesterol, ergosterol, lithocholic acid, cholic acid, dinosterol, betuline, or oleanolic acid, which may serve to retard the release rate of the agent from the copolymer. Such hydrophobic molecules prevent water penetration into the loaded polymer, but do not compromise the degradability of the polymer matrix. Further, such molecules may decrease the polymer matrix diffusion coefficient for the bioactive material to be released and thereby provide for a more sustained release of a bioactive material from the polymer matrix.

Methods of dispersing bioactive materials into polymers and the role of lyophilization to include thermoprotectants have been provided in U.S. application Ser. No. 11/300,283 of Binmoeller, filed on Dec. 15, 2005, which has been incorporated by reference.

Non-limiting examples of polymers that may be used in accordance with the present invention, particularly with regard to accommodating and releasing bioactive agents, include polyurethanes, polyesterurethanes, silicone, fluoropolymers, ethylene vinyl acetate, polyethylene, polypropylene, polycarbonates, trimethylenecarbonate, polyphosphazene, polyhydroxybutyrate, polyhydroxyvalerate, polydioxanone, polyiminocarbonates, polyorthoesters, ethylene vinyl alcohol copolymer, L-polylactide, D,L-polylactide, polyglycolide, polycaprolactone, copolymers of lactide and glycolide, polymethylmethacrylate, poly(n-butyl)methacrylate, polyacrylates, polymethacrylates, elastomers, and mixtures thereof. Representative elastomers that may also be used include, by way of example, a thermoplastic elastomer material available under the trade name "C-FLEX" from Concept Polymer Technologies of Largo, Fla., polyetheramide thermoplastic elastomer, fluoroelastomers, fluorosilicone elastomer, sytrene-butadiene rubber, butadiene-styrene rubber, polyisoprene, neoprene (polychloroprene), ethylene-propylene elastomer, chloro-sulfonated polyethylene elastomer, butyl rubber, polysulfide elastomer, polyacrylate elastomer, nitrile, rubber, polyester, styrene, ethylene, propylene, butadiene and isoprene, polyester thermoplastic elastomer, and mixtures thereof.

One of skill in the art can determine the amount or concentration of bioactive material(s) to include on the surface or within the material of the intestinal inserts of the present invention depending on particular treatment objectives and desired release profiles, as described in U.S. application Ser. No. 11/300,283 of Binmoeller, filed on Dec. 15, 2005, which has been incorporated by reference.

In some embodiments, the intestinal inserts of the present invention, or portions thereof, may include a topcoat or barrier to slow the diffusion or release of bioactive materials. Typically, the barrier should be biocompatible (i.e., its presence does not elicit an adverse response from the body), and may have a thickness ranging from about 50 angstroms to about 20,000 angstroms. In some embodiments the barrier may include a polymer provided over the polymer that diffuses bioactive materials.

In some embodiments, a barrier of the present invention comprises inorganic materials, which have been detailed in U.S. application Ser. No. 11/300,283 of Binmoeller, filed on Dec. 15, 2005, which has been incorporated by reference. Further detailed in that application are several methods that may be used to deposit a barrier over the inserts of the present invention. Nitride barrier coatings, such as, by way of example, titanium nitride, titanium carbonitride, chromium nitride, titanium aluminum nitride, and zirconium nitride may be deposited on the inserts of the present invention at relatively low temperatures by cathodic arc vacuum deposition. Such a method may be chosen where bioactive materials included within an insert of the present invention are temperature-sensitive. Further detailed in that application are methods for producing films of pure metals and alloys.

In some embodiments, it is contemplated that the barrier will contain mostly inorganic material. However, other embodiments may include barriers with a mixture of organic and inorganic materials or barriers of all organic materials. Some organic compounds that may be used in accordance with the present invention include, by way of example, polyacrylonitrile, polyvinylidene chloride, nylon 6-6, perfluoropolymers, polyethylene terephthalate, polyethylene 2,6-napthalene dicarboxylate, and polycarbonate. Generally, the solubility of the drug in the material of the barrier is less than the solubility of the drug in its polymer carrier. Also, generally, the diffusivity of the drug in the material of the barrier is lower than the diffusivity of the drug in its polymer carrier. The some embodiments, the barrier may be biodegradable. Appropriate biodegradable materials that may be used to create a barrier include, by way of example, calcium phosphates such as, by way of example, hydroxyapatite, carbonated hydroxyapatite, tricalcium phosphate, β-tricalcium phosphate, octacalcium phosphate, amorphous calcium phosphate, and calcium orthophosphate. Certain calcium salts such as calcium phosphate (plaster of Paris) may also be used. The biodegradability of the barrier may act as an additional mechanism for controlling drug release from the underlying first layer.

Active Control of Bioactive Material Release

Figure 23:
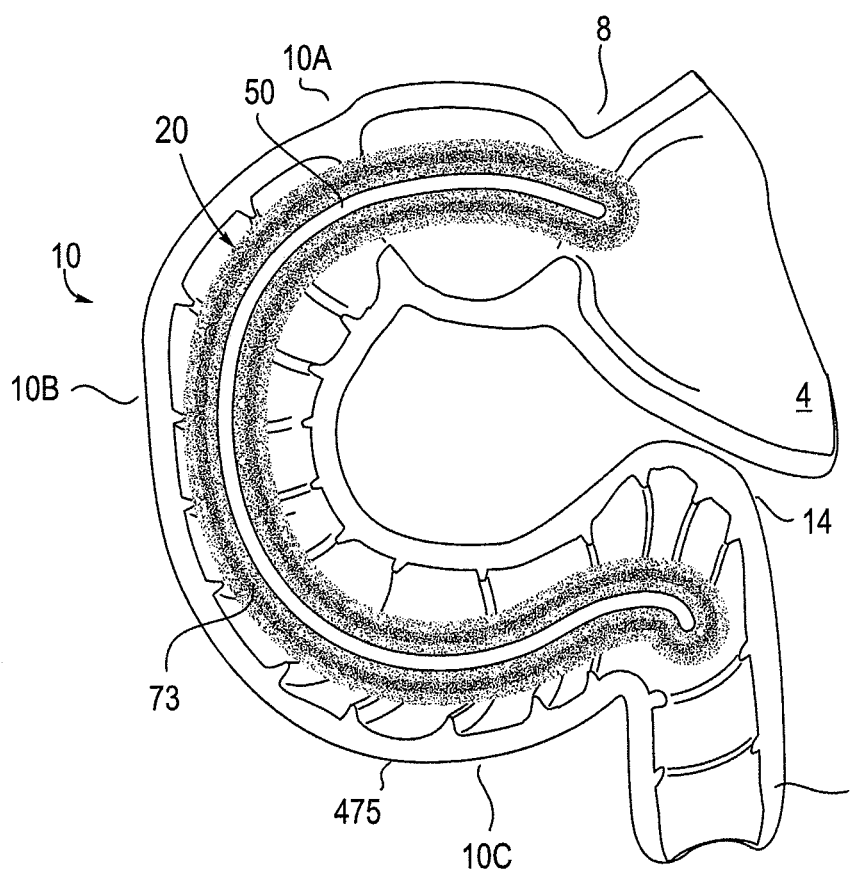
FIG. 23 depicts an embodiment of the insert with bioactive material in reservoirs that passively elute.
Figure 24:
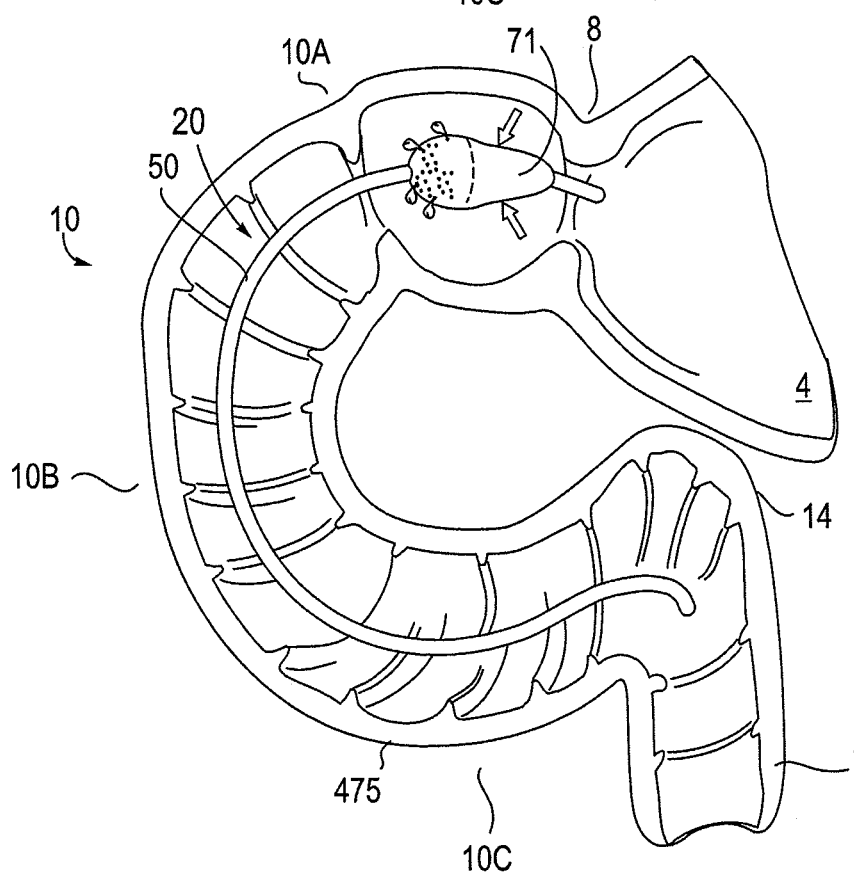
FIG. 24 depicts an embodiment of the insert with a bioactive material-loaded osmotic pump.
Figure 25:
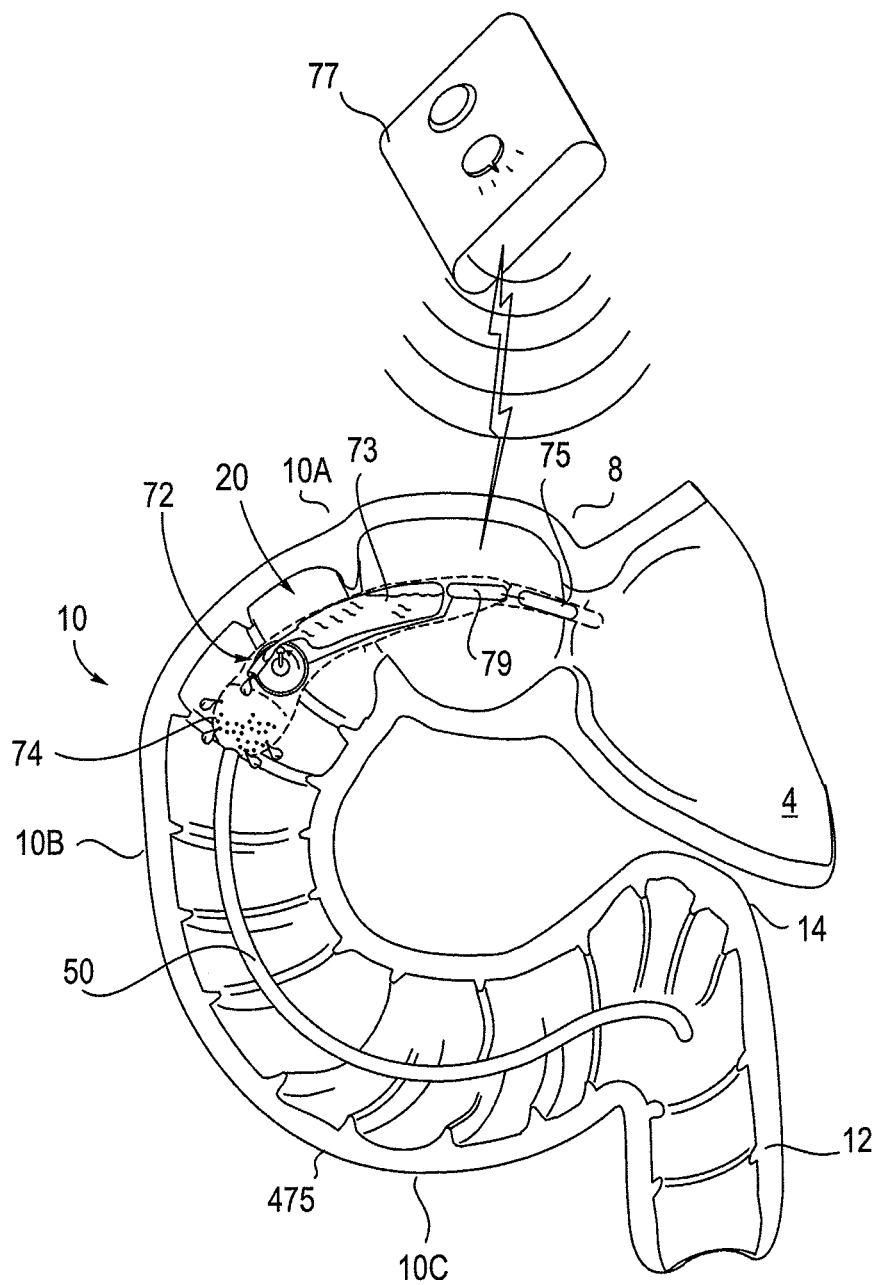
FIG. 25 depicts an embodiment of the insert with a bioactive material loaded reservoir coupled to an electrically driven pump, energy storage unit, and an external control.

Some embodiments of the device and methods provide a more active, i.e., a more controlled, or metered method of delivering bioactive agents, in contrast to the more passive diffusion of drug from surfaces or depots. These approaches are also more amenable to handling the delivery of multiple-drug release. Embodiments of the inventive devise may include a pump to dispense one or more bioactive agents from a reservoir or depot. Pumps may include electrically-driven pumps 72 mechanical pumps, piezo-electric devices that control pores, for example, or pumps may be osmotically-driven pumps 71. The osmotic pump delivery is relatively passive in that it does not require energy input, but it is controllable, predictable, and calibratable. Osmotic pumps typically are driven or urged via pH difference or concentration gradients. Release of bioactive materials may be controlled by external control devices, such as by an electronic signaling device either user-controlled or a programmable pacing/signaling device. Examples of devices that embody these active approaches to the delivery of bioactive materials or agents are described further below, and are depicted in FIGS. 23-25.

There are advantages to a drug delivery site within the intestinal lumen that may, for example advantageously be applied to the delivery of bioactive agents in a broader array than just drugs specific to modulating digestion or appetite. Such other agents may include chemotherapeutic agents, or radioactive particles for anti-cancer therapy. Another type of bioactive material that may benefit from local delivery may include cells, such as stem cells or activated immune cells, for cellular therapy of the intestine. Advantages of the intra-duodenal site of release may include proximity to target sites, taking advantage of specific chemical recovery receptors in the intestine, and minimizing systemic metabolism of drugs that occurs during the passage of the drug through such organs as the liver and kidney that occurs when drugs are delivered intravenously or orally.

In addition to delivering bioactive materials to the small intestine that may reduce food intake, the methods and devices of the present invention may be used to deliver other bioactive materials normally taken orally as well. The release of bioactive materials directly into the small intestine may be advantageous because many bioactive materials, including many drugs that are generally taken orally, are degraded by the harsh conditions of the stomach before they may reach the small intestine to be absorbed. For this reason, many bioactive materials are coated with layers of protective materials. By releasing bioactive materials, including drugs, directly into the small intestine, coatings to protect the bioactive materials may not be required. This lack of required protective coatings may be beneficial for patients because less unnecessary substances are introduced into their systems, and it is further beneficial as a process step reduction and cost reduction measure.

In another aspect of the invention which takes a more active interventional role, embodiments of the device may include an electronic emitter configured to apply an electrical potential to tissue in the stomach or duodenum. This electrical potential will trigger neuron-receptors and/or mechano-receptors, and/or osmo-receptors, and/or chemo receptors to send satiety signals to the brain. Exemplary embodiments of the device such as these are described further below, and depicted in FIG. 26. The role of embodiments of the intestinal insert and methods associated with its use are more generally considered in the context of FIG. 13, as detailed in the following section.

Further Exemplary Embodiments of the Invention

Figure 13:
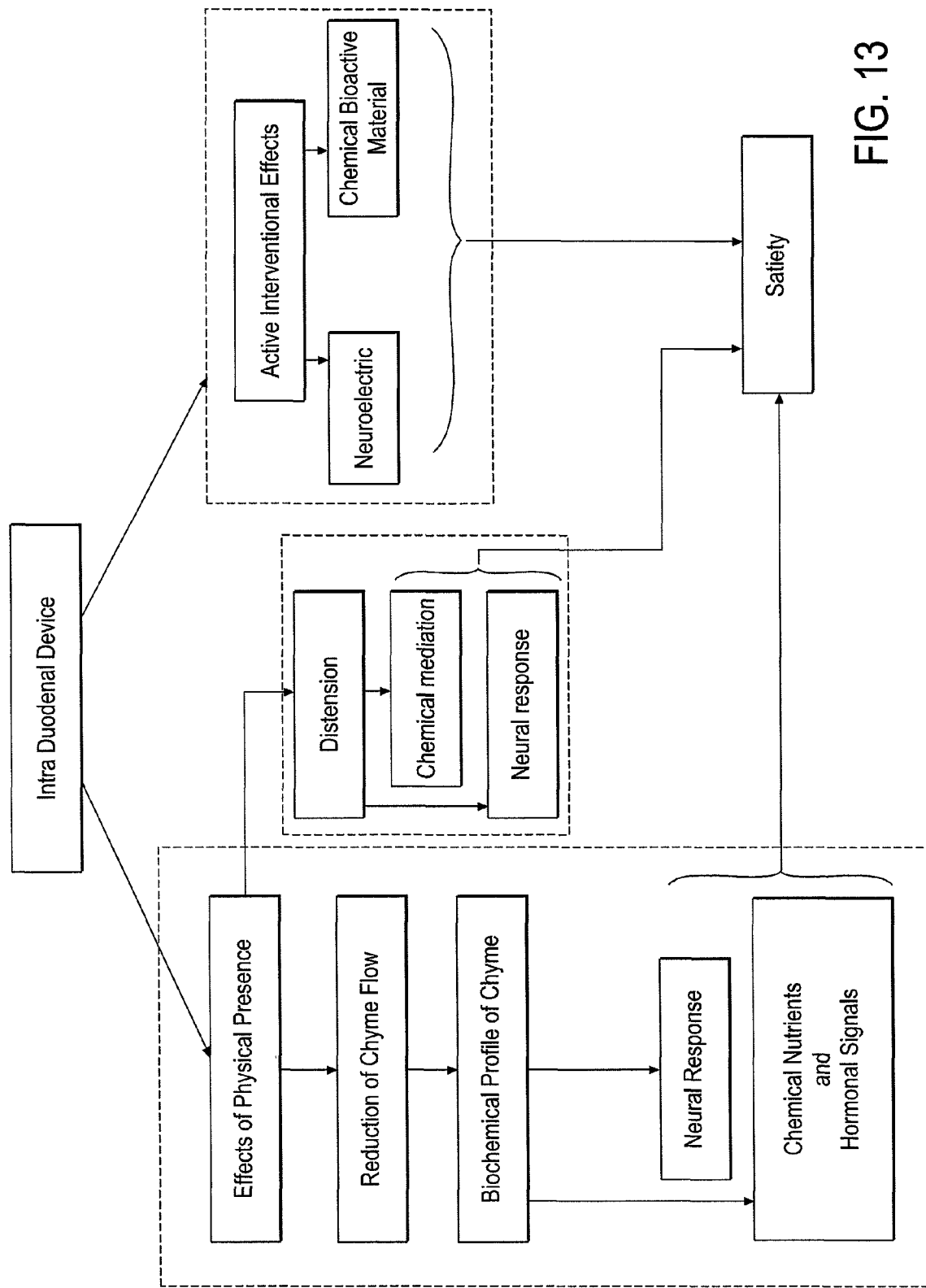
FIG. 13 is a flow diagram depicting the intestinal insert's role in contributing to the generation of one or more signals of satiety.

FIG. 13 is a schematic flow diagram of various embodiments of a method by which embodiments of the device engage the physiology of the host subject, and intervene in ways to generate a sense of satiety that ultimately reduces food intake. Embodiments of the inventive device intervene in the physiology of digestion and satiation by two broad approaches, each of which mimic or exploit the natural mechanisms of satiety. Embodiments may engage the physiology of the host subject by (1) their mere physical presence having effects, and/or (2) they may intervene more directly or actively by the direct provision of bioactive agents or direct neural stimulation. FIG. 13 and this associated description are provided as a simplified theoretical framework for understanding the invention; it is not intended to be complete in all detail; various interactions, dotted lines, and blurring of distinctions are omitted for sake of simplicity.

First, the mere physical presence of a device has two main effects, it has distensional effects and, if it has distinct flow reduction elements, it impedes the flow of chyme. Each of these two broad effects is dependent on the dimensions of the device and its flow reduction system, if the latter is present. First, then, the presence of the device distends the duodenum, and such distension may be neurally-sensed or detected, as for example, by stretch-sensitive neurons in the duodenum. Accordingly, any physical dimension, aspect, or feature, such as, by way of example, any of length, width, total volume, overall conformation or topography, density, weight, or surface properties may affect distension, or may be neurally detected in some way. Secondly, with regard to physically impeding the flow of chyme, this impeding process may alter the biochemical profile of digesting chyme, and chemoreceptors in the duodenum sense that profile as being more fully digested. It may also be that there is neural recognition more specifically of longer chyme residency time, as information separate from the altered biochemical profile per se; an effect such as that also then may be related to neural detection of distension. Neuronal pathways are indeed stimulated by distension, and neuroelectric signals and/or neuropeptides and neurotransmitters may be released for local or more distant sites of action. Joining neural feedback are chemical signals, both from the metabolite profile per se, and by the secretion of hormones such as CCK. Neural and chemical responses emanate to the central nervous system and other organs which, in sum, indicate that enough has been eaten, and satiation is achieved. In further response, the central nervous system supports a cessation of eating and digestive processes slow.

Second, with further reference to FIG. 13, embodiments of the device may intervene in a more active manner, beyond that which is provoked by mere physical presence. Embodiments of the device may assertively provide (1) bioactive agents and/or (2) provide electrical stimulation of nerves which then engage the physiology of satiety and digestion in the much the same manner, or through the same physiological pathways described above. In sum, a variety of effects of the presence of the device in the duodenum result in biochemical effects or signals (such as hormonal responses, and/or biochemical profile of metabolites both within the intestine and in the blood stream) and neural activity involving electrical signals, all of which converge physiologically to result in "satiety", with its complement of sensed satiety, sensed or perceived appetite, psychological correlates, and behavioral and habitual responses. As such, the action of the device or the presence of the device could be part of a method of providing therapy. The therapy may include providing a bioactive agent from the device to a portion of the gastrointestinal site. Moreover, this step of providing may produce a sensation of satiety in the patient.

Embodiments of the invention, a small intestinal insert, typically include an elongated member including at least one angled portion and at least one flow reduction element, for slowing the passage of chyme (or, stated in other terms, increasing the residency time of chyme) in the duodenum, although some embodiments of the device do not necessarily include a flow reduction element (as illustrated in FIGS. 23-26), and in some embodiments, the central or elongated member itself may be configured to reduce flow (FIG. 16, for example). These embodiments typically do have one or two angled portions that correspond to angled target portions of the duodenum. The configuration of the angled portions of the insert, including the flow reduction elements, is such that the device resides stably in the duodenum for a period of time. Embodiments of the insert may include adaptations that contribute to the generation of one or more physiological signals of satiety. Embodiments of the insert may include other features, such as the inclusion of biodegradable portions, a neurological stimulator, and one or more releasable reservoirs of bioactive materials that can be actively released by a bioactive material release mechanism.

Residency time of embodiments of the insert within the targeted angled site within the duodenum will vary according to the configuration of the embodiment and according to the particulars of the biodegradable materials that comprise portions of the device. Degradation of the device by biological processes is typically what causes release or unseating, or disengagement of the device from the target site, and elimination of the device through the intestinal tract. It may be understood therefore, that the device may be configured initially to sit or be seated in the targeted angled portion of the small intestine, and then, following a period of residency and through the effects of biodegradation, then configured to be unseated from the target site, and eliminated from the body by way of defecation. Biodegradability is feature of some polymers, and may be included in polymeric portions of any embodiment described herein and/or as illustrated in exemplary devices of FIGS. 3-12, or any device described herein. Biodegradation is a feature explicitly depicted in the embodiments shown in FIGS. 27 and 28.

Embodiments of the device elicit physiological signals of satiety typically through hormonal or neurological pathways. In some embodiments, the pathways are stimulated by the physical presence of the device, including a portion of or the sum total of a central member and flow reduction elements, whose collective or individual dimensions, either length, width, or total volume, or surface properties, are such that neuronal elements of the intestine, such as mechanoreceptors or stretch receptors, sense the presence of material which is interpreted as the presence of partially digested food, and therefore stimulate neuronal messages to the central nervous system that are interpreted as food satiation. In some embodiments, the central member, elongated body or spine may primarily provide the trigger for signaling. In some other embodiments, one or more flow reduction elements may primarily provide the trigger for signaling. In still other embodiments, a combination of the flow reduction element or elements and the elongated body provide the trigger for signaling.

In other embodiments, the satiety signal may be hormonal. Flow reduction elements slow the passage of chyme being processed in the duodenum, the biochemical profile of the food breakdown products is altered, and chemoreceptors in the duodenum respond to the altered biochemical profile in a manner that conveys satiety to the central nervous system and other portions of the digestive system.

In still other embodiments, the device includes reservoirs of bioactive materials that may be released, either by passive or active mechanisms. In the embodiments, the satiety signals are provided directly by the device, not by the endocrine pathways of the insert's host. Embodiments of the device may include material reservoirs of any type, including, for example, drug coatings that elute passively, or in concert with degradation of a host coating material, and some embodiments include reservoirs that are coupled with pumps. Such pumps may be mechanical, harnessing for example, biological energy conveyed by peristalsis, or electrical energy, or mechanical energy. Some embodiments may include osmotic pumps, which do not require input of electrical energy, but instead tap into the stored energy of osmotic gradients. Embodiments that are dependent on electrical energy for release by a pump typically include an energy storage device, such as a battery or a capacitor. Some of the powered embodiments include, as part of a larger system, a remote stimulator that can control the action of the pump. In some embodiments, the device may provide direct neural stimulation, through electrodes that stimulate local nerves in the duodenum, which convey a sensation of satiety to the central nervous system. As with pumps, devices that include neural stimulation features, may also include energy storage devices and external on/off or variable power control devices that communicate either by direct wired connection or wirelessly, as for example through radiofrequency signals.

Figure 14:
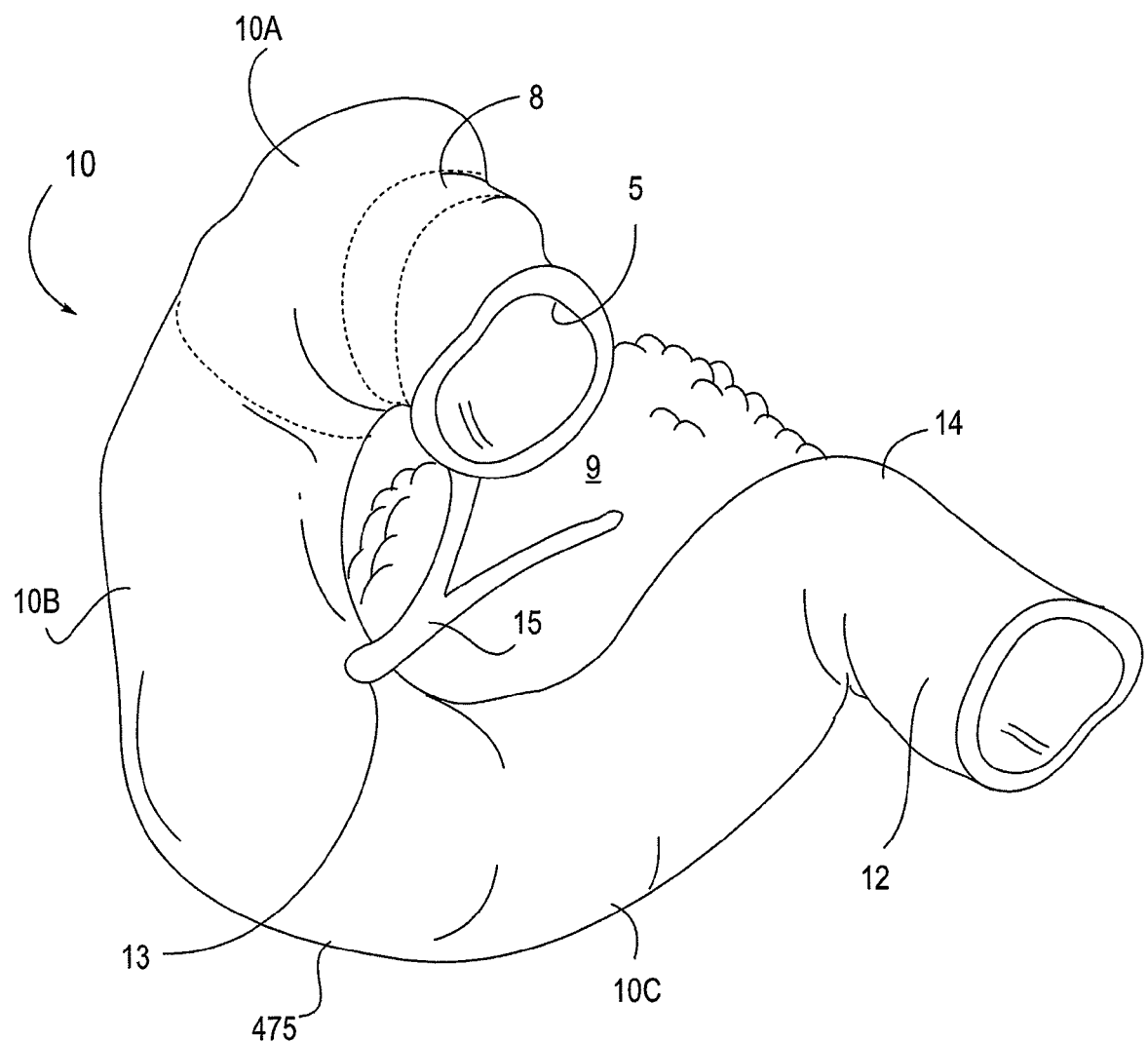
FIG. 14 is perspective view of the duodenum.
Figure 15:
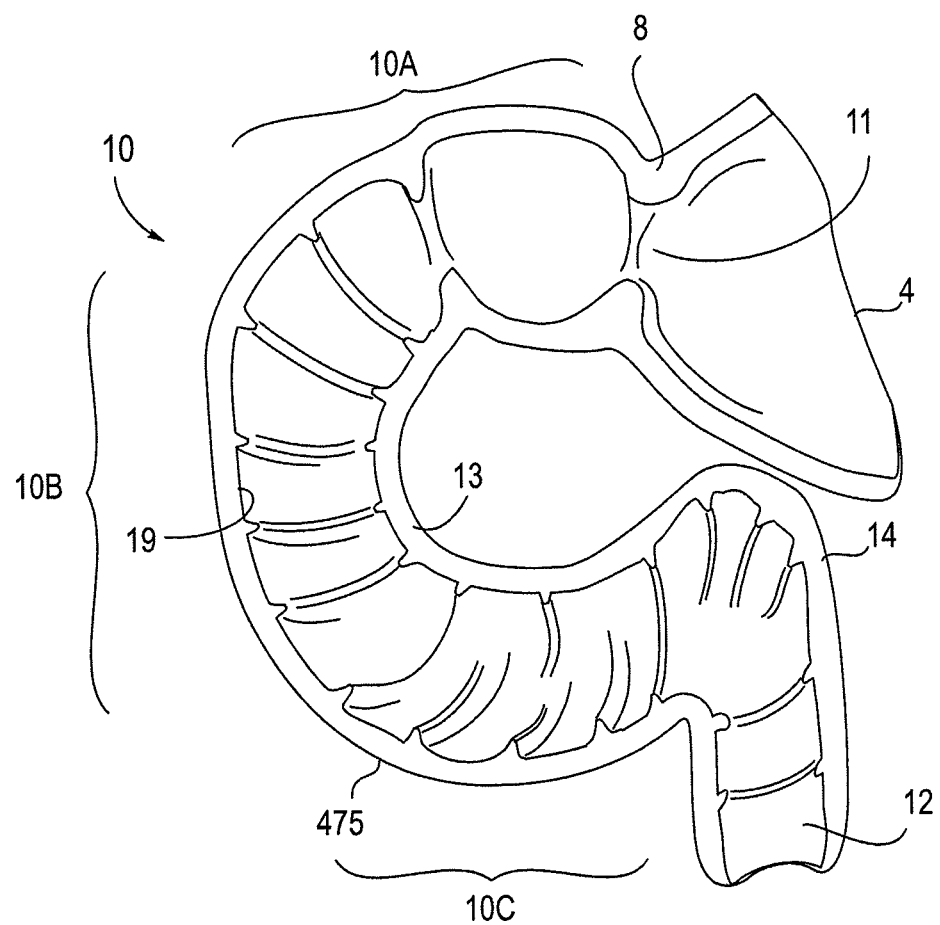
FIG. 15 depicts a side view of the duodenum, showing the folds of rugae that form the periphery of the inner space within which embodiments of the insert device are positioned.

FIG. 14 provides a perspective view of a portion of the human gastrointestinal tract that focuses on the duodenum of the small intestine 10, starting at the antrum-pyloric juncture 5, and extending to the entrance of the jejunum 12. Shown are the ampulla of Vater 13, the site of the entrance of the hepato-pancreatic duct 15, which is formed by the union of the pancreatic duct (from the pancreas 9) and the common bile duct from the liver. The pylorus 8 controls the discharge of contents of the stomach through a sphincter muscle, the pyloric valve 11, which allows the pylorus 8 to open wide enough to pass sufficiently-digested stomach contents. These gastric contents, after passing into the duodenum 10, continue into the jejunum 12 and on into the ileum. The duodenum 10, jejunum 12 and ileum make up what is known as the small intestine; however the individual portions of the alimentary canal are also commonly referred to as the small intestine. In the context of this invention the small intestine can refer to all or part of the duodenum, jejunum and/or ileum. FIG. 15 provides a flattened planar view of the duodenum 10, including the rugae 19, or inner-folding lining portion of the duodenum that form the periphery of the inner space within which embodiments of the insert device are positioned. Also depicted are the pylorus 8, the pyloric valve 11, the duodenal bulb 10A, the vertical duodenum 10B, and the horizontal duodenum 10C, the ampulla of Vater 13, and the initial portion of the jejunum 12. This figure provides a visual background for many of the figures that follow, each of which depicts an embodiment of the inventive inserted device seated within the targeted site of the duodenum.

Figure 16A:
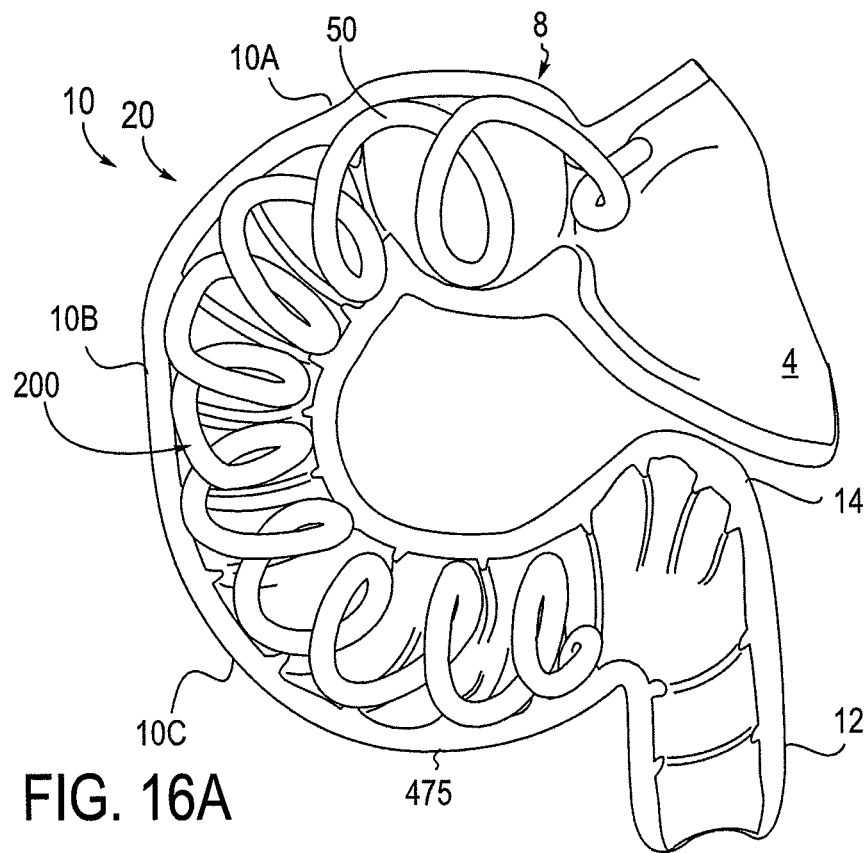
FIG. 16A depicts an embodiment of the insert with flow reduction elements in the form of a simple coil.
Figure 16B:
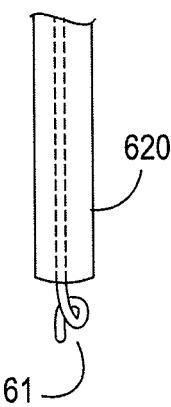
FIG. 16B depicts an end of the device as it emerges from a deployment tube.

FIG. 16A depicts an embodiment of the insert 20 with a central tube or member 50 in the form of a simple coil like a telephone cord; in this embodiment the flow reduction elements 200A may be understood as the individual coiled elements or segments of the extended central member 50. FIG. 16B shows a detail of a proximal or distal end portion of the device that takes the form of a coil 61, as it would emerge from a device deployment tube 620. Coil end portion embodiments may provide utility and advantage during deployment, as well as a stabilizing and non-irritating end-point when the insert is seated in the target site.

Figure 17A:
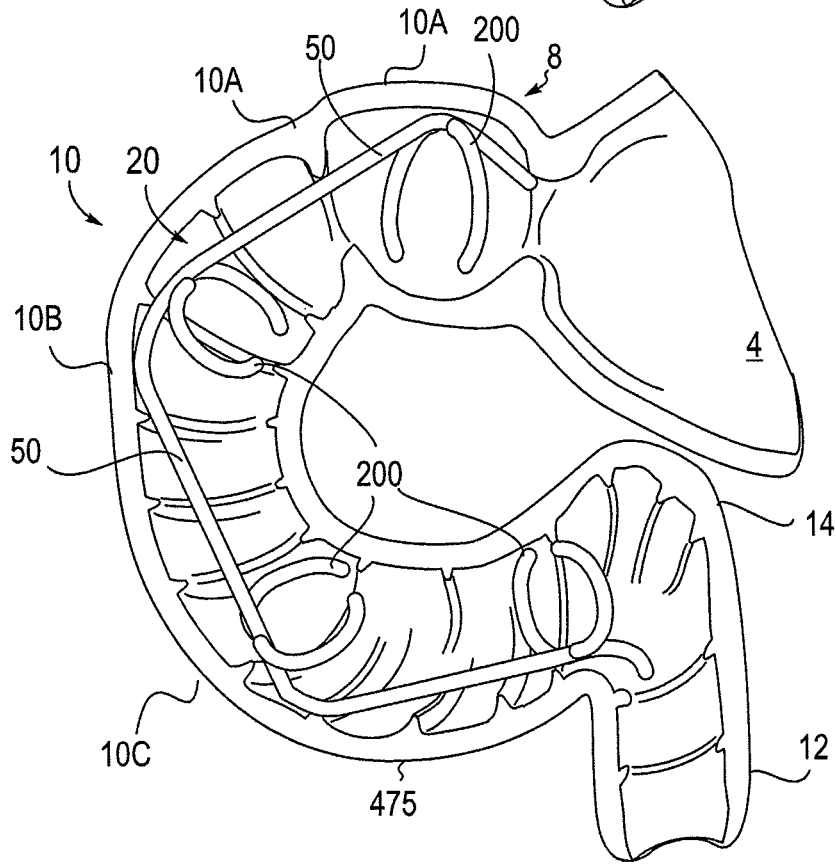
FIG. 17A depicts an embodiment of the insert with flow reduction elements in the form of a spine with ribs.
Figure 17B:
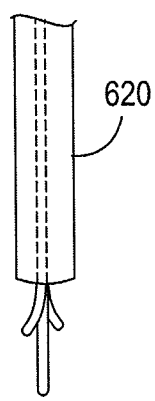
FIG. 17B depicts an end of the device as it emerges from a deployment tube.

FIG. 17A depicts an embodiment of the insert 20 with a central tube or member 50 in the form of a C-shaped spine, similar to the embodiment depicted in FIGS. 3 and 9, with flow reduction elements 200 in the form of ribs attached to the spine. FIG. 17B shows the central member 50 and tips of ribs 200 emerging from a deployment tube 620. Some embodiments of the rib-formed flow reduction elements 200 may be spring-like and outwardly biased, the elements reducing flow by their presence, but also, and advantageously, stimulating the wall of the duodenum 10, thereby contributing to the generation of a satiety signal, and further, contributing to stabilization of the insert as it resides within the targeted and angled site of the duodenum. In the latter regard, the duodenal bulb portion 10A bulges out to a wider radius than the more distal portion of the duodenum, and thus, an expansive element in this site provides a particularly effective stabilization site.

Figure 18:
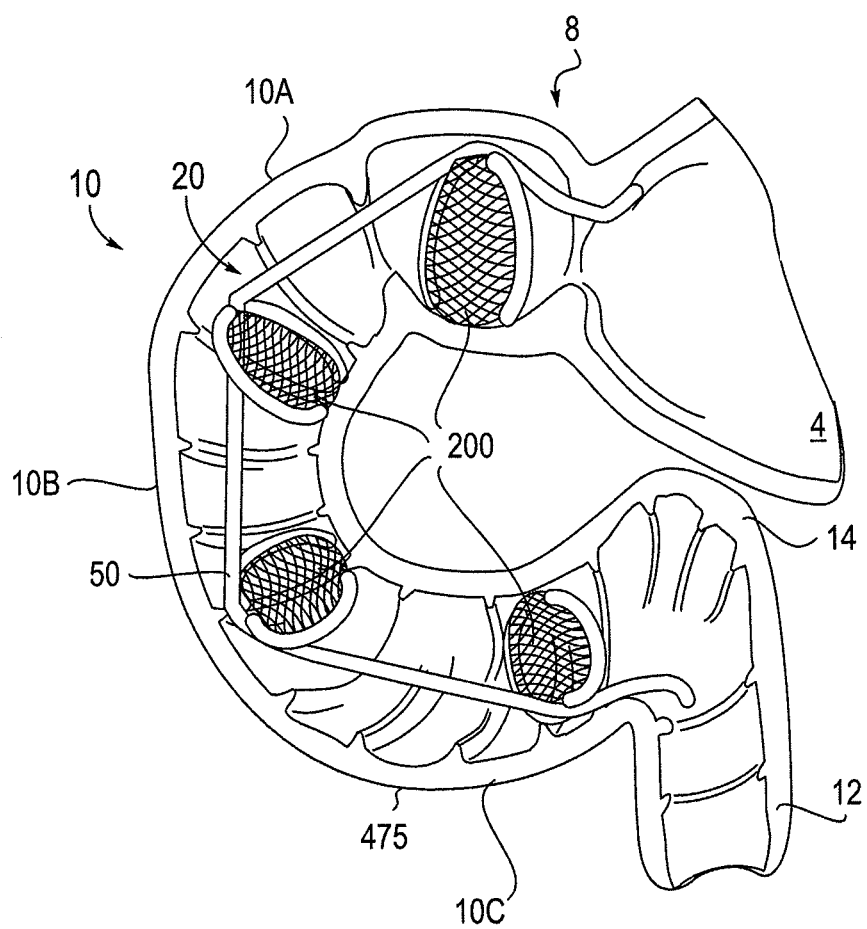
FIG. 18 depicts an embodiment of the insert with flow reduction elements in the form of a spine with nets.

FIG. 18 depicts an embodiment of the insert 20 with flow reduction elements in the form of a spine with nets. This embodiment may be considered similar to that shown in FIG. 17, but with a net, filter, or mesh deployed between expandable ribs. The expandable ribs provide benefits as described above; the netting provides leverage in terms of reducing the flow of chyme being processed through the duodenum 10. By use of mesh of varying pore size in the flow reduction elements 200, the device may be provided in variations that slow the flow rate to varying degree. Further, the mesh elements may be formed of materials of varying properties, such as varied hydrophilicity or hydrophobicity, which may have effects on chyme flow rate. Further still, the mesh may provide a site advantageous by virtue of its high surface area for the adsorption of bioactive materials, which may then passively elute or desorb during the period that the insert 20 resides in the duodenum.

Figure 19A:
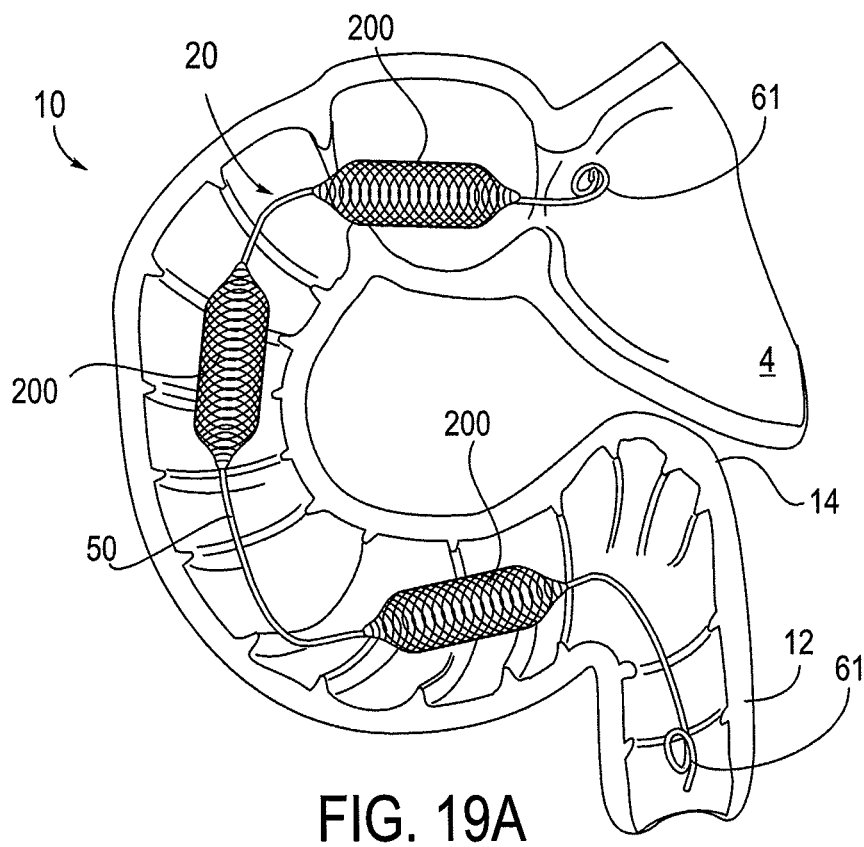
FIG. 19A depicts an embodiment of the insert with flow reduction elements in the form of closed mesh baskets, and further showing coil proximal and distal ends.
Figure 19B:
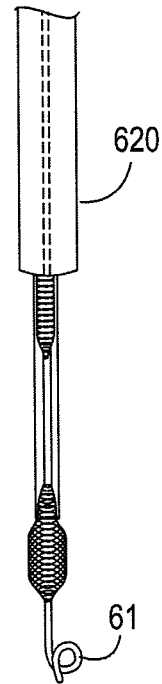
FIG. 19B depicts an end of the device as it emerges from a deployment tube.

FIG. 19A depicts an embodiment of the insert 20 with flow reduction elements 200 in the form of closed mesh baskets along a central member 50 and contiguous with it, and further showing coil proximal and distal ends 61. FIG. 19B shows the device emerging from a deployment tube 620, and expanding on emergence. Embodiments of the mesh baskets are flexible and expandable; the mesh may be of varying dimension and composition. Typically, the basket portions themselves do not form angles, but the interconnecting central portion 50 may form and resiliently hold predetermined angles. The composition of the baskets and the central portion may be identical and continuous, or the compositions may vary from each other. The interconnecting central portion 50, in particular, may further have shape-memory features, as provided either by shape memory alloys or shape memory polymers. The polymeric materials comprising the baskets 200 and/or the central member 50, whether resiliently shape-holding, or shape-memory capable, may further be biodegradable. An embodiment of a device similar to that depicted in FIG. 19A, particularly with regard to the mesh or braid comprising embodiments of flow reduction elements, are described further below, and depicted in FIG. 44.

Figure 20:
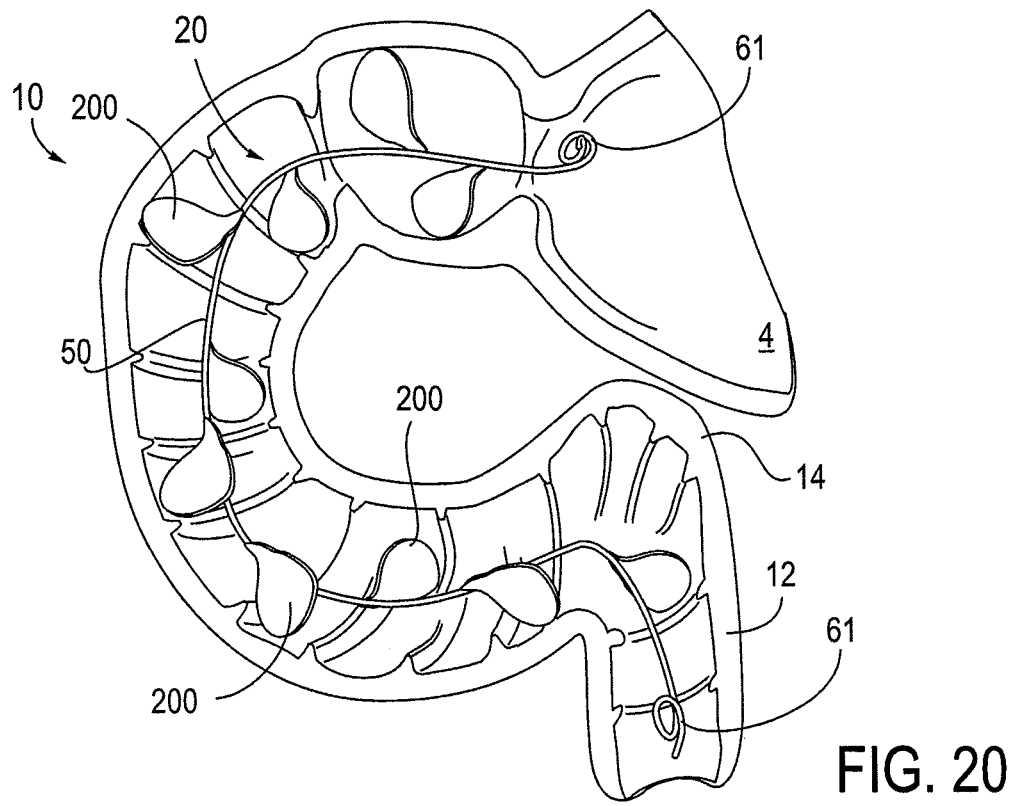
FIG. 20 depicts an embodiment of the insert with flow reduction elements in the form of centrally-mounted outwardly-extending baffles, and further showing coil proximal and distal ends.

FIG. 20 depicts an embodiment of the insert 20 with flow reduction elements 200 in the form of centrally-mounted outwardly-extending baffles, and further showing coil proximal and distal ends 61. The baffles are mounted at spatial intervals on a central member 50 that may include angled portions that are maintained by resiliently-shaped or memory-shaped materials, as described in the context of the embodiment shown in FIG. 20.

Figure 21:
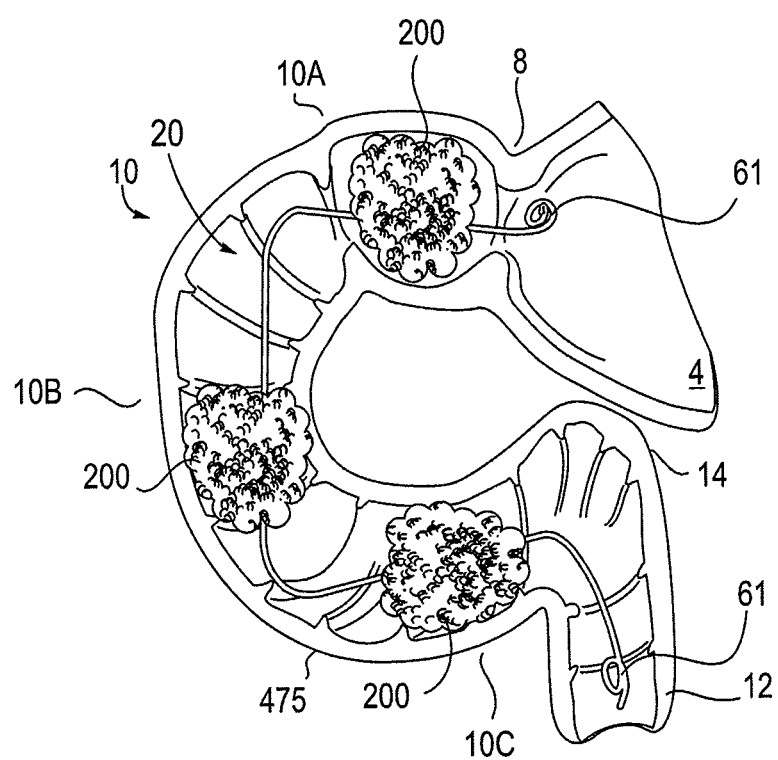
FIG. 21 depicts an embodiment of the insert with flow reduction elements in the form of a foam-like bodies, and further showing coil proximal and distal ends.

FIG. 21 depicts an embodiment of the insert 20 with flow reduction elements 200 in the form of foam-like bodies, and further showing coil proximal and distal ends 61. This embodiment, in broad aspect, is similar to the embodiment shown in FIG. 6. Foam-like flow reduction elements 200 are compressible and expandable, and are thereby amenable to deployment into a target zone through narrow tubes or scopes. The foam-like materials may be of a closed-cell form or an open-cell form, or they may be hydrogels. Such foam-like materials serve the flow reduction function well because they are bulky, compliant, and tend to be space-filling. They also provide a high amount of surface area, which is advantageous for adsorption of bioactive agents, as provided by embodiments of the invention, which may then be passively desorbed during the residency period within the duodenum. Such foam or sponge-like materials may also be wholly or partially biodegradable. The biodegradability generally serves the purpose of providing for a limited residency time, as well as being a way in which to disperse bioactive agents incorporated or adsorbed onto the material.

Figure 22:
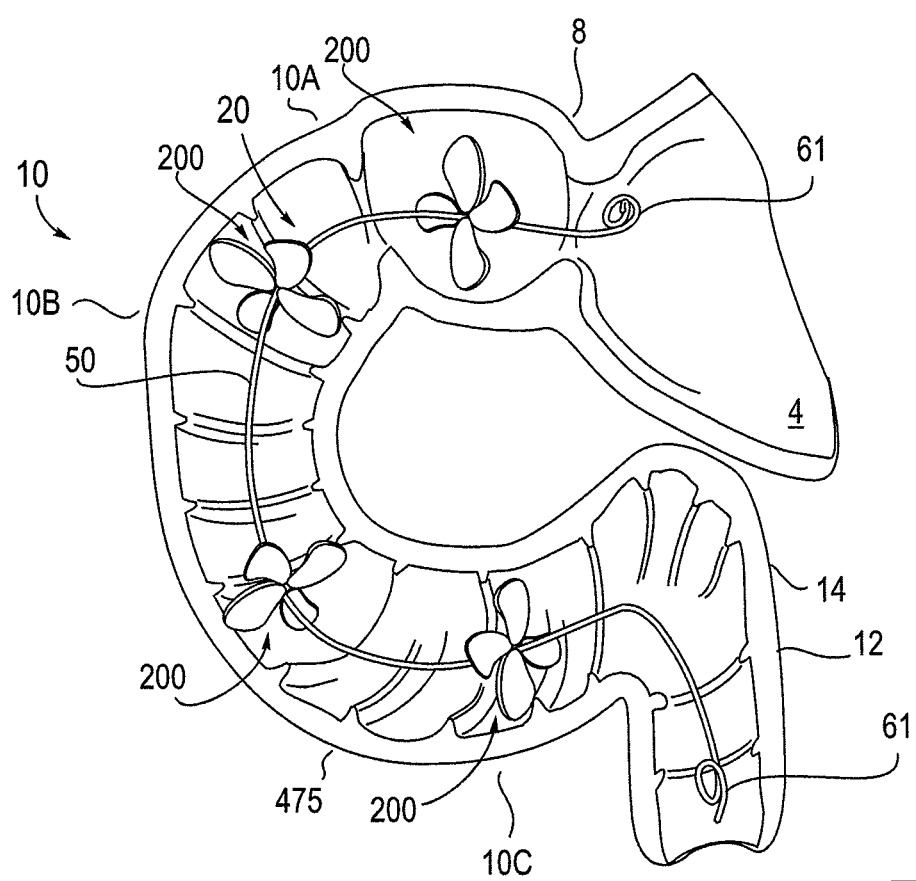
FIG. 22 depicts an embodiment of the insert with flow reduction elements in the form of a centrally-mounted fans, and further showing coil proximal and distal ends.

FIG. 22 depicts an embodiment of the insert 20 with flow reduction elements 200 in the form of a centrally-mounted fans or blades, mounted at spatial intervals on a central member 50, and further showing coil proximal and distal ends 61. Such fan blades 200 may be rotatable, with variable degrees of resistance to rotation, including minimal resistance. To the extent that such flow reduction embodiments 200 do rotate in accordance with the flow of processing chyme, such movement may be beneficial in that mixing of chyme may be a useful process as an adjunct to reducing flow rate.

FIG. 23 depicts an embodiment of the insert 20 with bioactive material in reservoirs or depots, or layered, or adsorbed, or incorporated on the central- or elongated member 50, from which the bioactive agent may passively elute into the duodenum 10. This embodiment emphasizes the bioactive material or agent delivery aspect of the devise, and it is shown without any particularly formed flow reduction element other than its own physical dimension, however, it should be understood that a drug eluting central member 50 such as this may be combined with any of the various flow reduction elements 200 depicted in other figures.

FIG. 24 depicts an embodiment of the insert 20 with a bioactive material-loaded osmotic pump 71, as supported by central or elongate member 50. Osmotic pumps are well known in the art, as provided, for example, by Alza Corporation (Cupertino, Calif.). The actuation of an osmotic pump may occur in various ways; for example, water driven by a chemical potential crosses an osmotic membrane and enters a salt chamber. The increased volume in the salt chamber forces an expansion membrane to deflect into a drug reservoir. As the expansion membrane pushes into the reservoir, the drug is dispensed via one or more outlet ports.

FIG. 25 depicts an embodiment of the insert 20 with a bioactive material loaded reservoir 73 coupled to an electrically driven pump 72, energy storage and dispensing unit 75, all such components being supported by central or elongate member 50, as well as external control 77. As in FIGS. 23 and 24, the presently depicted embodiment emphasizes the delivery of a bioactive agent or material to the targeted duodenal site. Any of these embodiments could include more than one drug. The difference between this bioactive agent dispensing embodiment and those of FIGS. 23 and 24 is that they are relatively passive, running on a predetermined time course as determined by the particulars of bioactive agent release mechanism. In the embodiment depicted in FIG. 25, however, the release of the bioactive material is under active control of a pump, and the pump may be further under the control of an external control that communicates to the pump either by an implanted wire, or, as depicted here, by wireless communication, as for example by radiofrequency transmission. A device may include more than one such unit, or a single unit may include more than one reservoir and pump, thus more than one bioactive agent may be delivered independently from a single device 20.

Figure 26:
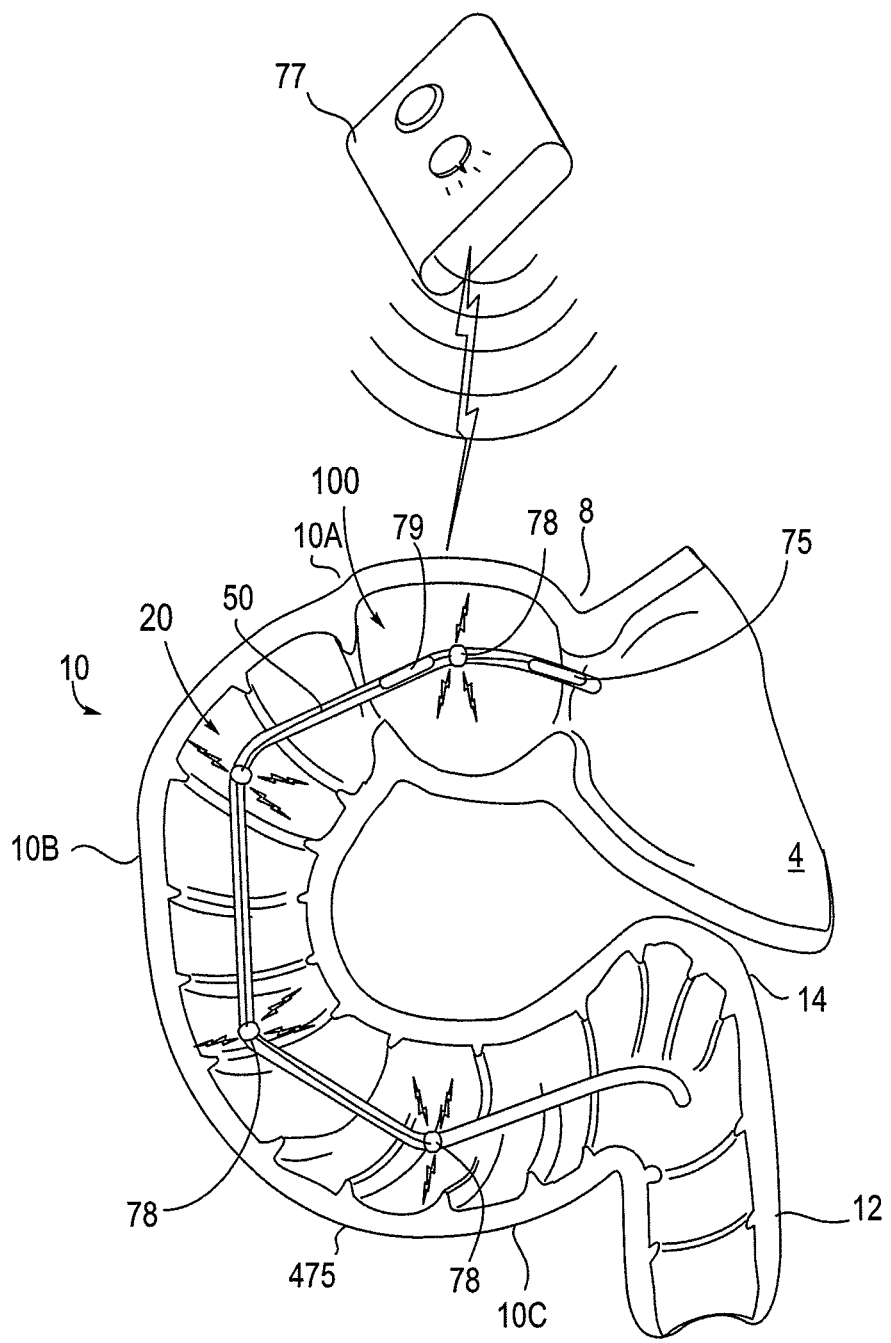
FIG. 26 depicts an embodiment of the insert with electrodes for local neurostimulation, an energy storage unit, and an external control.

FIG. 26 depicts an embodiment of the inventive insert 20 with electrodes 78 for local neurostimulation, an energy storage and delivery unit 75, such as a battery or capacitor, and an external controller 77, all such components being supported either directly or indirectly by the central or elongate member 50. This embodiment is illustrated in such a way so as to focus on neuronal stimulation, but as explained above in reference to drug-eluting devices, the neural stimulatory features of the device may be combined with any of the various flow reduction elements 200. In the present embodiment, the electrodes may be advantageously positioned at sites where nerves are known to reside. Electrodes may target more than one nerve to stimulate, or may target a nerve at more than one point.

FIGS. 27A and 27B depict an embodiment of the central member 50 of an insert 20 that includes biodegradable elements and shape memory elements. FIG. 27A shows the central member in an intact configuration with angles α and β apparent; FIG. 27B shows the central member after biodegradation has begun. At a later point, the central member will deteriorate further, lose its integrity and conformation, and the angles α and β will disappear as the defining arms of the C-shape device disappear. As such, this represents an embodiments of device that is configured first to sit within a targeted site in the intestine, and then following residency and a period of biodegradation, the device is configured to become unseated from the target site, such unseating due to the loss of the initial conforming correspondence to the target site. In the exemplary embodiment depicted here, an insert device 20 is formed from a combination of curved shape-memory alloy portions 22 and relatively straight biodegradable polymer portions. The metal portions 22 and polymer portions 24 are joined together segmentally to create an insert of full dimension and with a complete an angle or curve as desired, such as angles of radius α and radius β depicted in FIG. 9. The metal portions have expanded portions at either end to provide a more substantial joining surface, and to protect the host subject from injury or irritation from sharps, as the metal elements are loosed upon biological degradation of the member 20 as a whole. Metal and polymer portions may be joined together in other ways to complete an angled device, as would be familiar to those skilled in the art.

FIG. 28 depicts an embodiment of the central member 50 of an insert that includes a biodegradable polymeric material; biodegradable polymers have been described extensively, above. FIG. 28A shows the central member in an intact configuration; FIG. 28B shows the central member after biodegradation has begun. At a later point, the central member 50 will further disintegrate, and angles of radius α and radius β will no longer hold their form. In some embodiments, the polymeric material may be capable of resiliently holding an angle, such as angles of radius α and radius β depicted in FIG. 9, and in other embodiments, the polymer may be of a type capable of holding a shape memory, as described above.

Conformationally-Stabilized Devices in a Residence Site: General Considerations

Embodiments of the invention include devices or intestinal inserts with an elongated member with a proximal end and a distal end and an angled or curved portion between the proximal end and the distal end. The curved portion typically corresponds to a curved aspect of a residence site in a lumen of the body, for example, a portion of the gastrointestinal tract, and more particularly, the duodenum. The device is stabilized against distal or proximal movement relative to the residence site by a conformation that corresponds to the residence site, and more particularly, such conformation does not correspond to a site immediately distal and/or proximal to the residence site. Depending on the particulars of device design and location of a residence site, the device conformation may stabilize the device against proximal device movement, distal device movement, rotational device movement or a combination of any of these movements. Typically in luminal sites within the gastrointestinal tract there is a greater accumulation of forces that tend to move a device situated therein in a distal direction than in a proximal direction, as the general flow of contents, and the direction of peristalsis are both distally-directed. Accordingly, it is of particular importance that the device be stabilized against a distal-ward drift. Additionally, devices described herein are also suited to resisting proximal directed forces such as regurgitation. Accordingly, some embodiments of devices described herein are configured to resist gastrointestinal forces that may dislodge the device from a residence site whether the forces are proximally directed or distally directed.

Some embodiments of conformationally-stabilized devices, as described herein, do not rely on a hard or specific attachment or tethering anchor to stabilize at a target residence site, nor do they rely on an anchoring mechanism that resists downward drift by being blocked at a site of radial dimension limitation, such as the pylorus. Instead, embodiments of the device stabilize at a residence site by virtue of the conformation of the device in part or as a whole fitting into the residence site. Moreover, the device has sufficient structural integrity that it resists being moved relative to the residence site because an immediately distal and/or proximal location does not conformationally accommodate the device.

The conformation of a device that provides its stability in a residence site refers to the physical totality of the device, including the dimensions in units of measure such as length, width, and volume, as well as shape, which relates to the distribution of the dimensions in space. While not desiring to be bound by theory, it is believed that a device self-stabilizes at a residence site because that position within the residence site represents the state of least free energy in a system that includes the device and the residence site. In other aspects, ends proximal and distal to the corresponding curved portion are in proximity to one another for further stability.

Aspects of the device that are adapted to provide conformational stabilization at a target site in a lumen of the body include physical dimensions of length and width, as well as angles or curvature assumed by the lumen. Conformationally stabilized (or conformationally-stabilizable devices) may vary with respect to the degree to which their physical aspects of size and shape correspond to the size and shape of the intraluminal residence site to which they are targeted; their characteristic feature is that it is their conformation that stabilizes them against movement from the target site, once situated therein. More particularly, it is typical that such stabilization involves at least one curved or angled portion of the device that is accommodated by a corresponding at least one curved angled portion of the residence site, and the angled portion of the device characteristically provides a curvilinear retaining force within that site.

Some conformationally stabilizable embodiments may further stabilize in a residence site by providing radially outward force that meets the surrounding wall of the lumen. Conformationally stabilizing devices further may vary with regard to their stiffness or compliance in response to forces exerted upon them by the luminal residence site. A device with a high degree of stiffness bends or changes its own shape relatively little in response to forces exerted by the residence site, while a highly compliant device offers little resistance and complies with forces exerted on it by bending or changing shape. A conformationally stabilized device thus must have a sufficient degree of stiffness and overall structural integrity in order for its conformation to maintain its stability.

Some embodiments of a conformationally stabilizing device have a high degree of size and angular correspondence to their target site, in which case the residence site substantially retains its native configuration when occupied by the device. In some of these embodiments with a high degree of correspondence to the target site, the angles and the placement of angles along the length of a device substantially match the shape and linear dimensions of the residence site. In other embodiments, the device, in spite of having a conformation that as a whole stabilizes it at a residence site, the device, or more specifically, the preferred or unconstrained conformation of the device may nevertheless vary in terms of size and shape with respect to the target site. In some embodiments, a device with a preferred configuration that varies with respect to the residence site does not substantially change the shape of the residence site, as the device may be more compliant than the residence site. In some embodiments of devices that vary in conformation from that of the residence site, the device, if provided with sufficient stiffness and conformational integrity, may impart a change of shape to the luminal residence site. Typically, the configuration of devices that changes the shape of residence site is a feature that contributes to the stability of the device in that target site.

Some embodiments of the conformationally-stabilizing device are configured such that the conformation of the structure as a whole, including substantially the totality of physical features, is substantially directed toward providing conformational stability. With other embodiments, however, some aspects of the conformation of various physical features may not be directed specifically toward providing conformational stability, but rather may be directed toward another functional or therapeutic end, such as reducing the flow of chyme (as detailed in U.S. patent application Ser. No. 11/300,283 and 11/807,107), or toward other therapeutic purposes or modalities, as described further herein below. In other embodiments, physical features may not be designed singularly to support conformational stability, but, rather such features may be designed such that they serve one or more functional purposes. A physical feature may, for example, contribute both to providing conformational stability and toward another functional or therapeutic purpose. In any of these aforementioned embodiments that include physical features that are not specifically-focused or singularly-focused on contributing to the stability of the device within the residence site, these embodiments nevertheless have a sufficient total level or amount of conformational features that are directed toward supporting conformational stability that the device is capable of stabilizing in a residence site by virtue of such totality of conformation, particularly in gastrointestinal luminal sites that include one or more curvilinear or angled aspects.

Some embodiments are targeted to the duodenum and described in detail, but other embodiments are targeted to residence sites elsewhere in the gastrointestinal tract. Further, as mentioned above, some devices are configured to align with a high degree of correspondence with their designated residence site, while other vary in correspondence, and by such variance may alter the shape of the residence site. Further, some devices, though stabilized substantially by the conformation of the device which precludes movement that displaces it from the residence site, may further derive site-stabilizing benefit from a balance of materials-based and construction-based features such as structural integrity, elasticity, stiffness, and ability to counter lumen-generated radially-inward force with a radially-outward counterforce.

Conformation refers to the physical totality of the device, including the dimensions in units of measure such as length, width, and volume, as well as shape, which relates to the distribution of the dimensions in space. While the claims to this invention are not bound by theory, to understand the invention it can be theorized that a device self-stabilizes at a duodenal residence site because its residence there represents the state of least free energy in a system that includes the device within the gastrointestinal tract.

Some embodiments of the duodenal device are configured to reside within gastrointestinal tract residence sites completely within the duodenum. The duodenum is anatomically situated distal to the pylorus and stomach and proximal to the jejunum, as illustrated in FIG. 14. Some other embodiments, however, may include portions that extend proximally in a minimal manner, into the pylorus, and some may extend further proximally into the antrum of the stomach. Some embodiments may extend further distally, past the site of the ligament of Treitz, and into the jejunum. However, even these embodiments that include portions extending proximally or distally from the duodenum still rely on conformational stabilization within the duodenum to preclude dislodgment from the residence site and consequent movement of the device as a whole. As a result, such embodiments do not rely, for example, on being constrained from distal or downstream movement by the radial constraint of the pylorus.

The duodenal residence site of embodiments of the device includes at least one angled portion, and the device, accordingly has at least one angled portion that corresponds to that angled portion within the residence site. Other embodiments of the device may include two, three, four, or more angled portions between the proximal and distal end of the device, these angles corresponding to angles in a residence site. The duodenal residence site can also be understood as a continuous curvilinear form, and accordingly, some embodiments of the device are configured as a curvilinear form, without particular angled regions.

Figure 29:
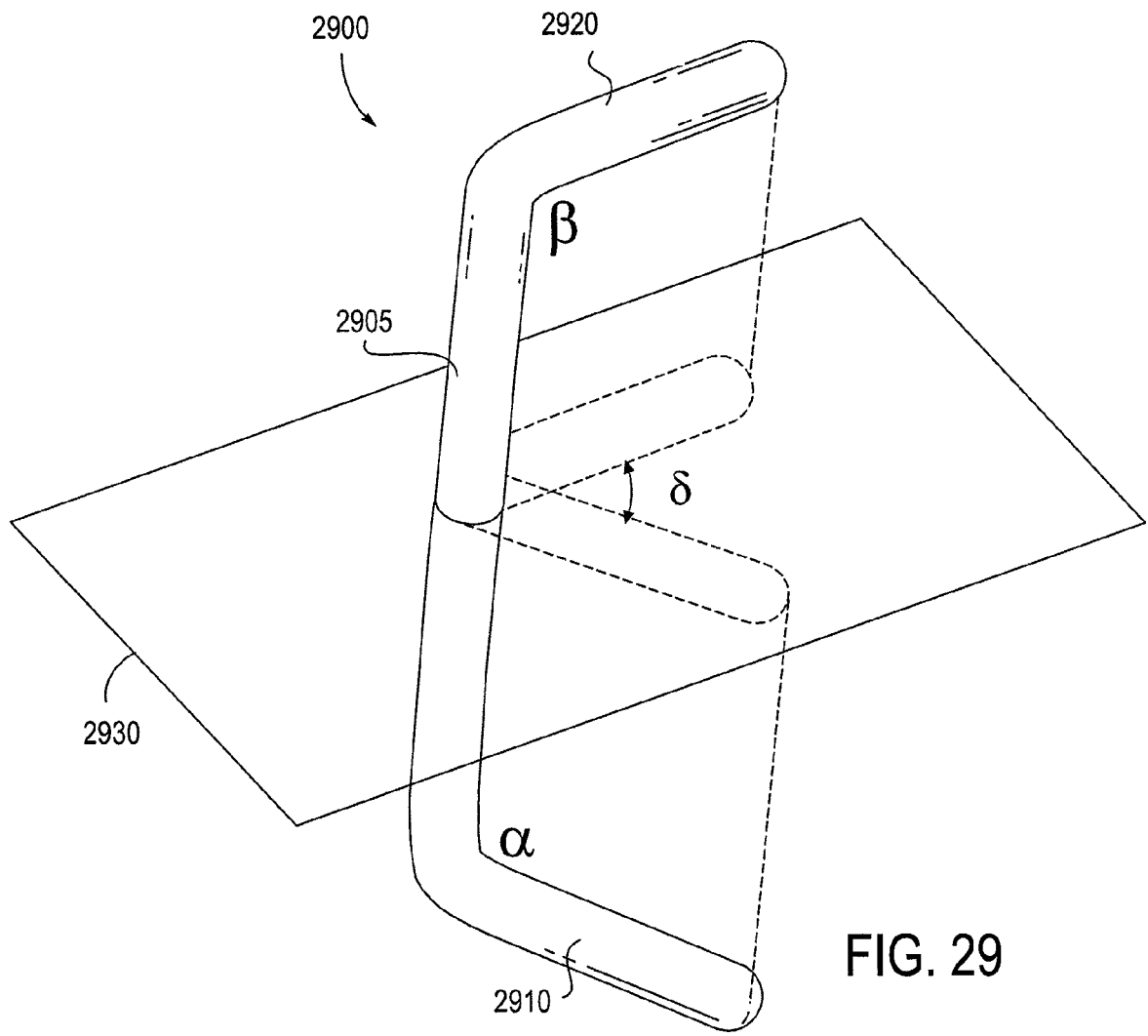
FIG. 29 provides a perspective schematic view of device with three substantially straight central portions of an elongate body, focusing on angles alpha, beta, and delta that determine the relative conformation of the three portions with respect to each other.
Figure 30:
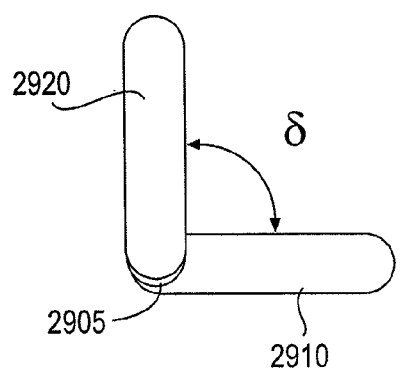
FIG. 30 provides an axial facing view of the device shown in FIG. 29.

FIG. 29 illustrates an embodiment of a conformationally stabilized insert 2900 with at least two angled portions. The insert 2900 may be described as a central segment 2905 with two peripheral segments, a distal segment 2910 and a proximal segment 2920. As described in U.S. patent application Ser. No. 11/807,107, the two angles defined by the junction between the central segment 2905 and the two peripheral segments 2910, 2920 may be understood as angle alpha and an angle beta, respectively. Additionally, a third angle delta may be used to describe the relationship and orientation of the components of an insert. A central segment of the device is disposed between the two angled portions, wherein each angled portion joins the central segment with a first peripheral segment and with a second peripheral segment. The axes of the central segment and the first segment define a first plane and the axes of the central segment and the second segment define a second plane. The lines representing the intersection of each of these two planes on a third plane perpendicular to the axis of the central segment form an angle delta.

As best seen in the perspective view of FIG. 29 the angle delta is formed by the projection of the proximal segment 2920 and distal segment 2910 onto a plane 2930 substantially perpendicular to the central segment 2905. The angle delta is also shown in the top down view of FIG. 30. The angle delta ranges between 0° and 90° in some embodiments. The angle delta range and selected value will vary depending upon the specific anatomy of the targeted residence site or the desired modification of a targeted residence site.

This general description of angle delta as it applies to a device with two angled portions and a central segment situated between two peripheral segments may be generalized to describe a device with more than two angles, indeed any multiple number of angles, and with a segment between each angle. In these embodiments, it can be understood that an angle delta is associated with each individual segment (with the exception of the most peripheral and most distal segments). Thus, each segment is associated with an angle delta that describes the relationship between the two planes defined by the segment and each peripheral segment. The shape of the device may be described based in part on the totality of the angles describing the relationship between adjoining segments along the main axis of the device, and the delta angles associated with the segments.

The totality of the conformation of the device depends not only on the angles, but also on the dimensions of each segment in absolute terms, such as, for example, in units of length, width, and volume. Additional aspects of the total device conformation are described in the embodiments that follow.

Conformationally-Stabilizing Device Examples

Some embodiments of the conformationally stabilized device are structurally based on a central spine that may vary in form, and provide a support base for other structural elements. Such elements may have specific functions, such elements that reduce the rate of chyme flow and increase the residency time or transit time through the duodenum, while other elements attached to the spine may contribute to the overall ability of the device to correspond with the residence site, and contribute to the conformational stability of the device. Attached elements in some embodiments may serve still other functions, such as stimulating neural receptors, such as mechano-receptors within the luminal wall, that are responsive to movement, stretch, or pressure. Other embodied features may serve an atraumatic function. FIGS. 16A and 16B, 19A and 19B, 20, 21, and 22 for example, show coils on the ends of devices, such coils preventing trauma to the luminal wall that could occur from contact with device ends that have stiffer, sharper, or otherwise less forgiving device ends. For purposes of illustration, in some of the figures that follow, the spine is used as a representative embodiment and may be depicted in a size smaller that which would typically be suitable for the targeted residence site so as not to distract the anatomical detail of the targeted residence site.

Figure 31:
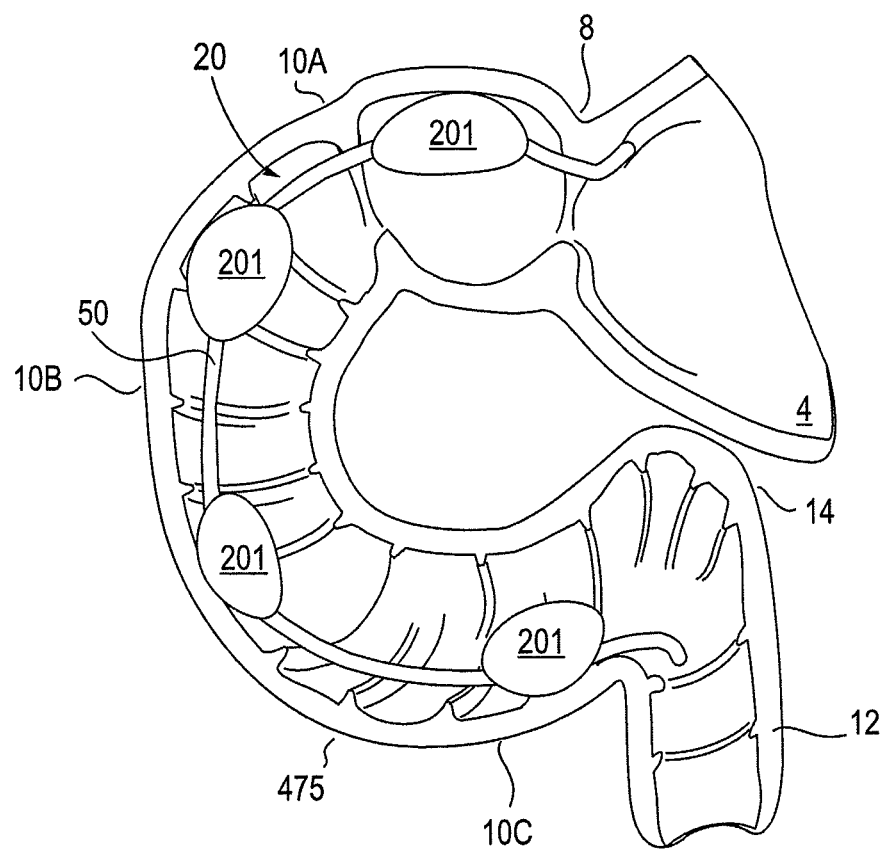
FIG. 31 provides a view of a device with structural feature projecting from a central spine that contributes to conformationally stabilizing the device.
Figure 32A:
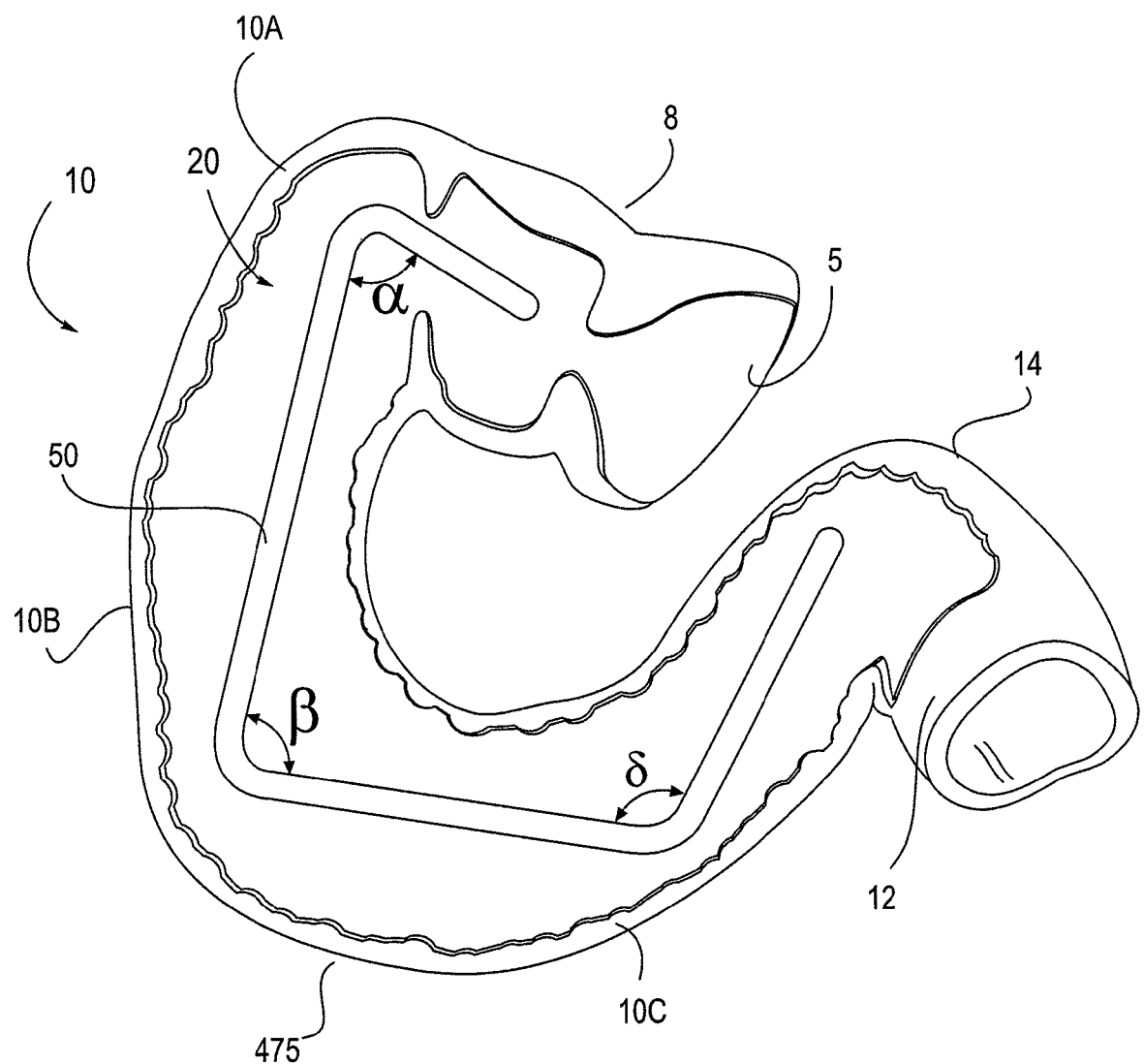
FIGS. 32A-32C show alternative embodiments of conformationally-stabilizing devices, each with substantially straight major segments of an elongate body that vary in length, angles between each segment, and residence site within the duodenum.
Figure 32B:
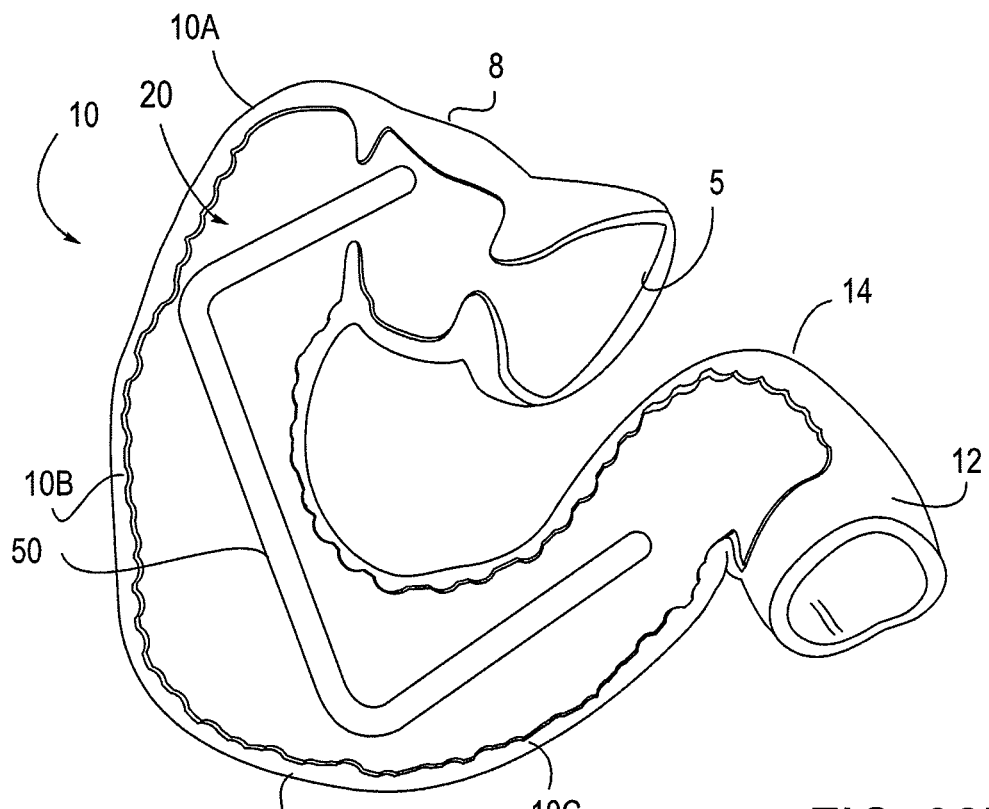
Figure 32C:
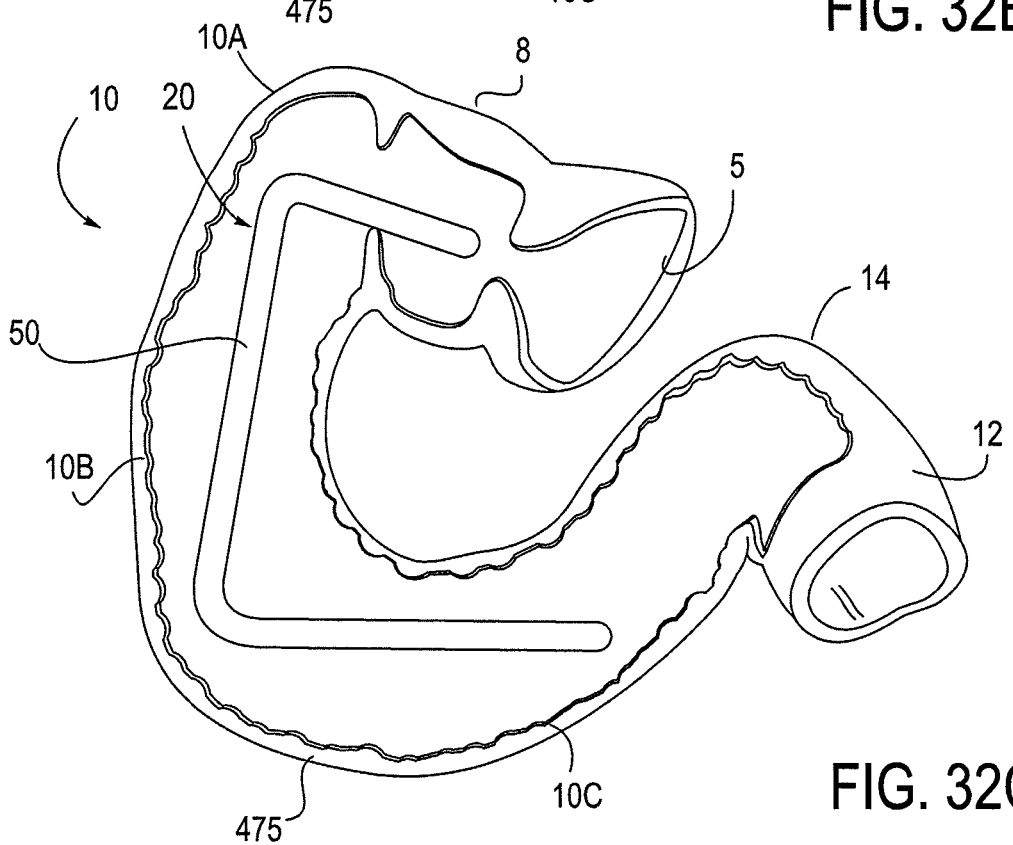
Figure 33:
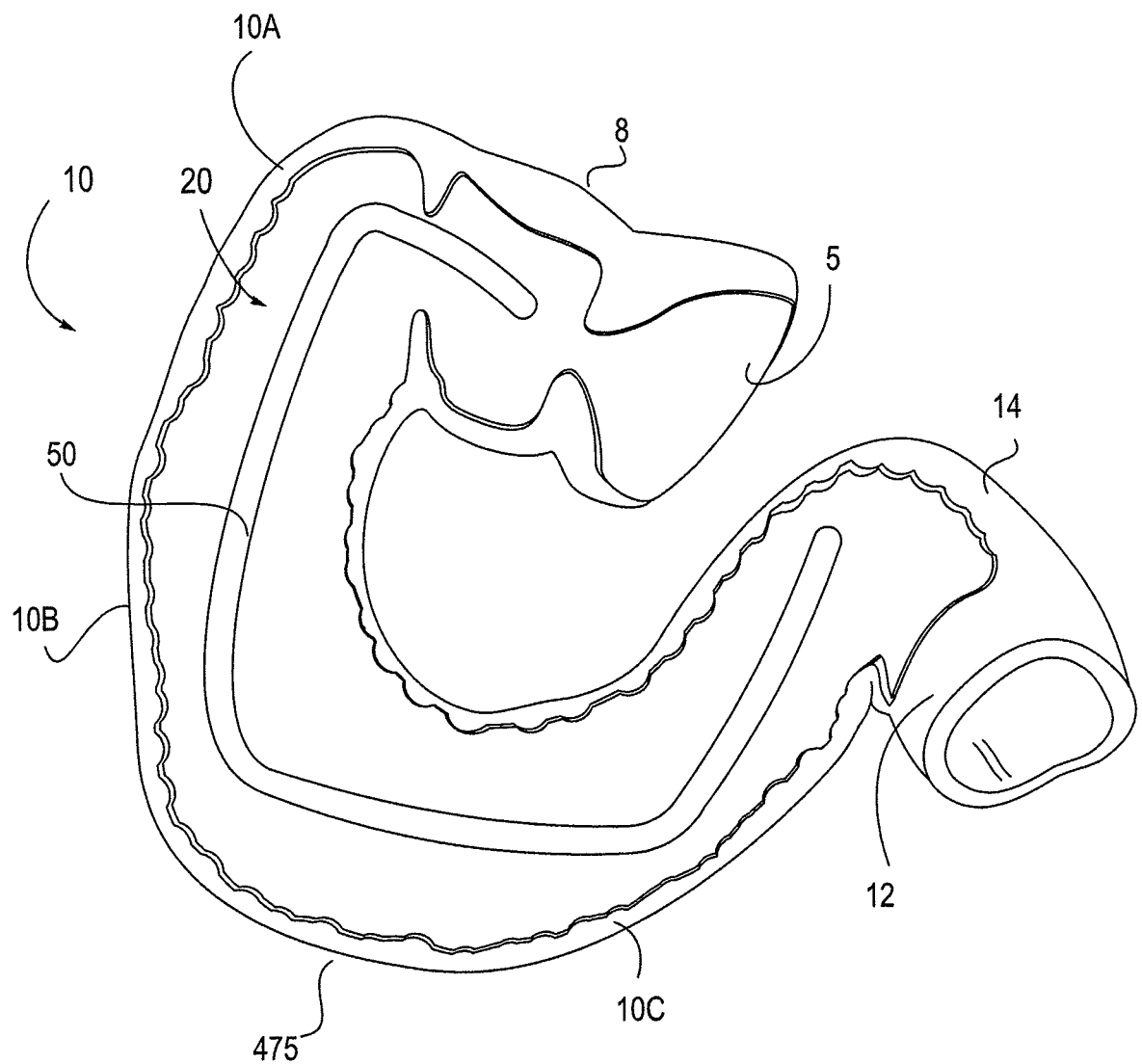
FIG. 33 provides a view of a conformationally-stabilizing device with four curvilinear segments comprising the elongate body.
Figure 34:
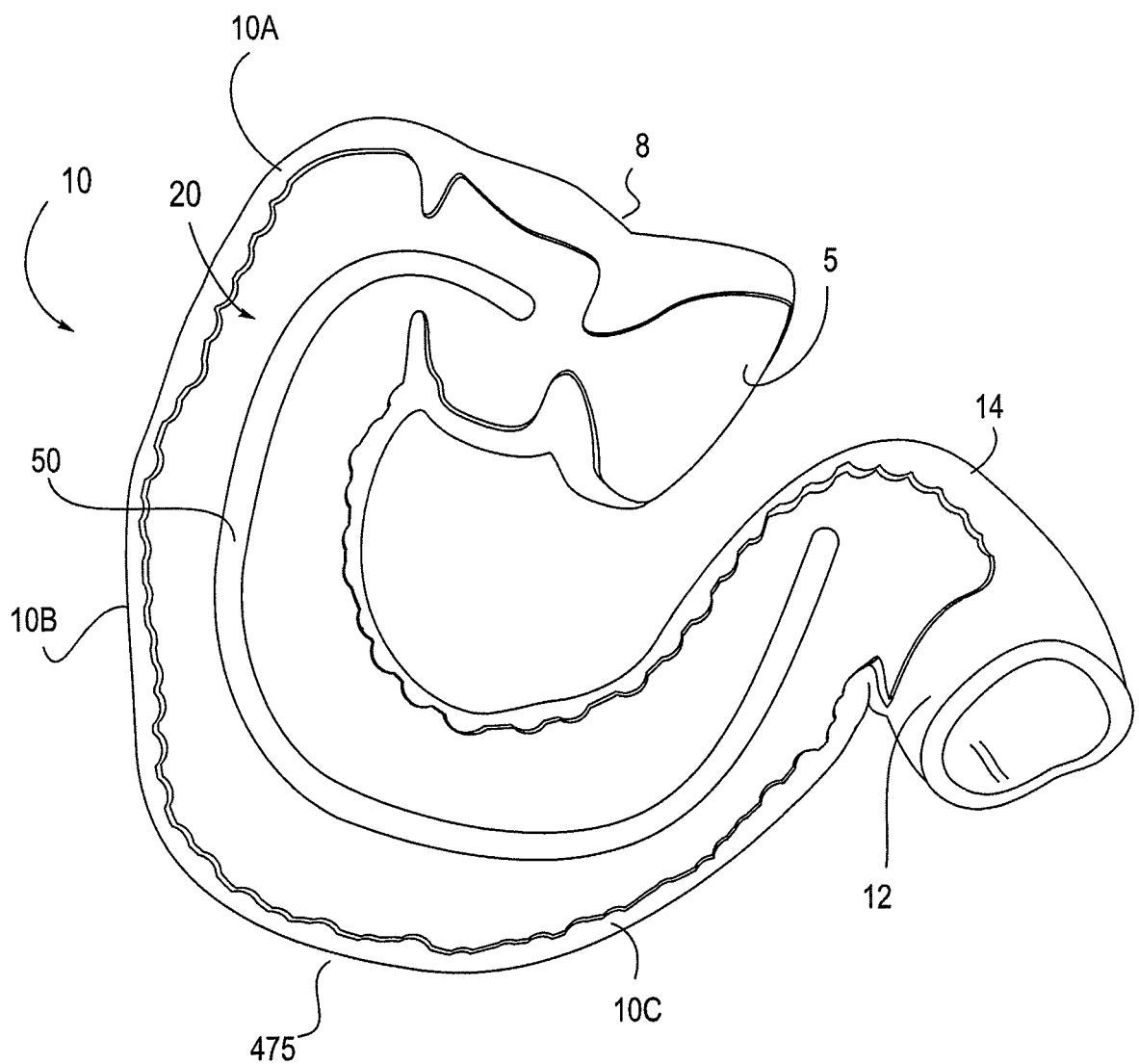
FIG. 34 provides a view of a conformationally-stabilizing device with a single curvilinear portion comprising the elongate body.
Figure 50A:
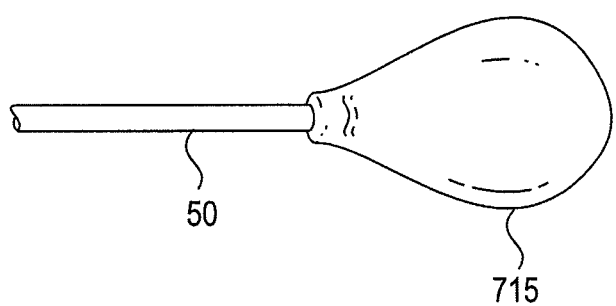
FIGS. 50A-50D shows spoon or paddle shaped atraumatic end features of a conformationally-stabilizing device.

FIG. 31 illustrates a device where a structural feature projecting from a central spine contributes to conformationally stabilizing a device. FIG. 31 includes a cross section view of the duodenum 10 with an insert 20 conformationally stabilized therein. Insert 20 includes structural features 201 distributed at positions along the spine 20 that are shaped to conform to a portion of the duodenal residence site. Structural features may be of any suitable shape and size to conform to the desired location. For example, structural features may be spherical, elliptical, ovoid, circular, rectangular, polygonal, curvilinear or any other compound or simple shape that corresponds to the targeted residence site for that structural feature. As shown in FIG. 31, the structural features 201 have a generally elliptical shape that is bulged or warped to conform to the residence site. It can be further understood that structural features such as these advantageously distribute force that the device is exerting on the wall of the duodenum at contact or pressure points over a wider surface area, reducing the force impinging per unit area at such points, and thereby providing such pressure points a level of protection. These structural features may contribute to flow reduction, but that is not their designated function, which is, instead, to contribute to the stability of the device, and to distribute pressure the device may bring to bear on the gastrointestinal wall over a broad surface area. The same principle of force distribution is seen later in the form of spoon- or paddle-shaped atraumatic ends, as seen in FIGS. 50A-51.

The spine of a spine-based device, in some embodiments may be configured for a radially-central position within the duodenum as shown and described in FIGS. 19, 20, 21, and 22. In other embodiments, the spine is configured for a radially off center position in the duodenum as shown and described in FIGS. 17 and 18.

In some other embodiments the spine is segmented into substantially straight segments, as shown and described in FIGS. 17, 18, and 21. Some embodiments include a spine with three segments such as, for example, the embodiment illustrated in FIGS. 4, 9, and 28. Still other embodiments include a spine with more than three segments such as, for example, FIGS. 3, 26, 27, and 32A Still other embodiments include a segment or segments that assume a more curvilinear form such as, for example, the devices shown in FIGS. 16A, 20, and 22-25, 44, 46A, 46B, 47, 48, and 51.

In still other embodiments, the spine may assume an overall curvilinear form, without discrete segments, as depicted in FIGS. 23, 24, and 25 of U.S. patent application Ser. No. 11/807,107 and in FIGS. 33, 34, 35, and 36. The curvilinear shape can be described by a Cartesian coordinate system or a curvilinear coordinate system. The curvilinear coordinate system is used for a Euclidean space that is based on a transformation of the standard Cartesian coordinate system. As the spine may be described as spherical in shape, a polar coordinate system can specifically be used.

In some embodiments, the spine may assume a convoluted form and the convolutions are used to provide conformational stability, in addition to other functions they may have, such as slowing the flow of chyme. Convolutions in an insert are illustrated and described in FIGS. 16A and 17A.

Some embodied configurations may advantageously include extensions or portions of the device that extend beyond the duodenum, as into the pylorus, or as in further to the antrum of the stomach, or, alternatively, extending distally beyond the duodenum, and into the jejunum. An example of an embodiment that extends beyond the duodenum is provided by FIG. 36, where the proximal portion 20P of the conformationally stabilized device projects through the pylorus and into the antrum of the stomach; and the distal portion 20D extends into the duodenal-jejunal flexure. While this configuration may provide advantageous leverage in embodiments configured to change the shape of the duodenum, these embodiments may also be configured to allow the duodenum to substantially retain its native shape, in which case the portions that extend beyond the duodenum may provide for an increased curvilinear retaining force in general. With regard to a larger view of the gastrointestinal tract, it can be understood that the proximal and distal ends of the device are in close apposition because the anatomical points where they reside (the gastric antrum and the duodenojejunal junction or, externally, the ligament of Treitz) actually are in such close apposition. This particular embodiment (FIG. 36) does not have flow reduction elements, but is otherwise similar in length and placement to the embodiment depicted in FIG. 44, and as shown in a residence site in FIG. 47.

Conformationally-Stabilized Devices that Alter Residence Site Shape

In some embodiments, a device of the present invention corresponds to a residence site in a target location, particularly with regard to an angled site, and the segments or lengths of the device on either side of the angle within the residence site. However, the device may vary in terms of the exactness of the matching of the respective angles of the device to those angles of a residence site at a target location within the body, and it may further or alternatively vary in segment lengths or curvilinear portions between angles. In some embodiments, the device has a resilient bias in an angled portion that is angularly larger than the angled portion of a residence site. In still other embodiments, the angled portion of the device may have a resilient bias that is inward, or angularly smaller than the angled portion of a residence site. Still other embodiments may have a resilient bias that is nearly congruent with the native residence site configuration.

Additionally or alternatively, in devices with angles that correspond to one or more angles in a residence site, some device angles may be more obtuse and some angles may be more acute than the angle to which they correspond. In any of these embodiments where the angles of the device vary with respect to the native angles of the residence or target site, the device may effect a change on the shape of the residence site occupied by the device. Typically, the net effect with regard to the conformational stability of the device is to enhance the stability. However, in some embodiments where the shape of the residence site is changed, the effect of the change is to serve a therapeutic purpose, as elaborated on in a following section, in an organ or system associated with the residence site. While the foregoing examples have used the variation of angled portions of a device, the invention is not so limited. On other embodiments, portions of the device other than or in addition to an angled portion may be modified to produce a shape altering result of a portion of a residence site. It is to be appreciated that shape changing conformational inserts may also pinch, clamp or crimp a portion of a residence site.

Conformationally-Stabilized Devices that Alter the Shape of the Duodenum

Figure 37:
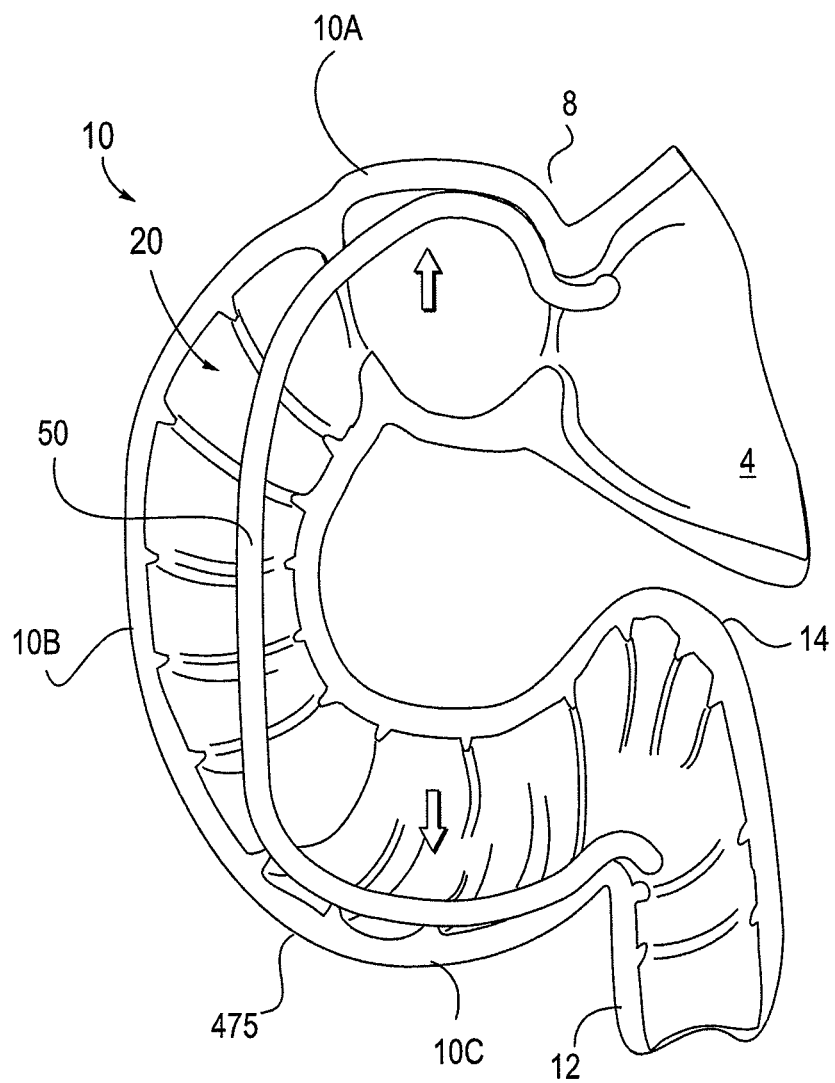
FIG. 37 provides a view of conformationally-stabilizing device with a relatively long central portion, a proximal portion that reaches through the pylorus, a distal portion that terminates near the duodenojejunal junction, and an outwardly deflecting bias that alters the shape of the duodenum by distending it along a cephalad-caudal axis.
Figure 38:
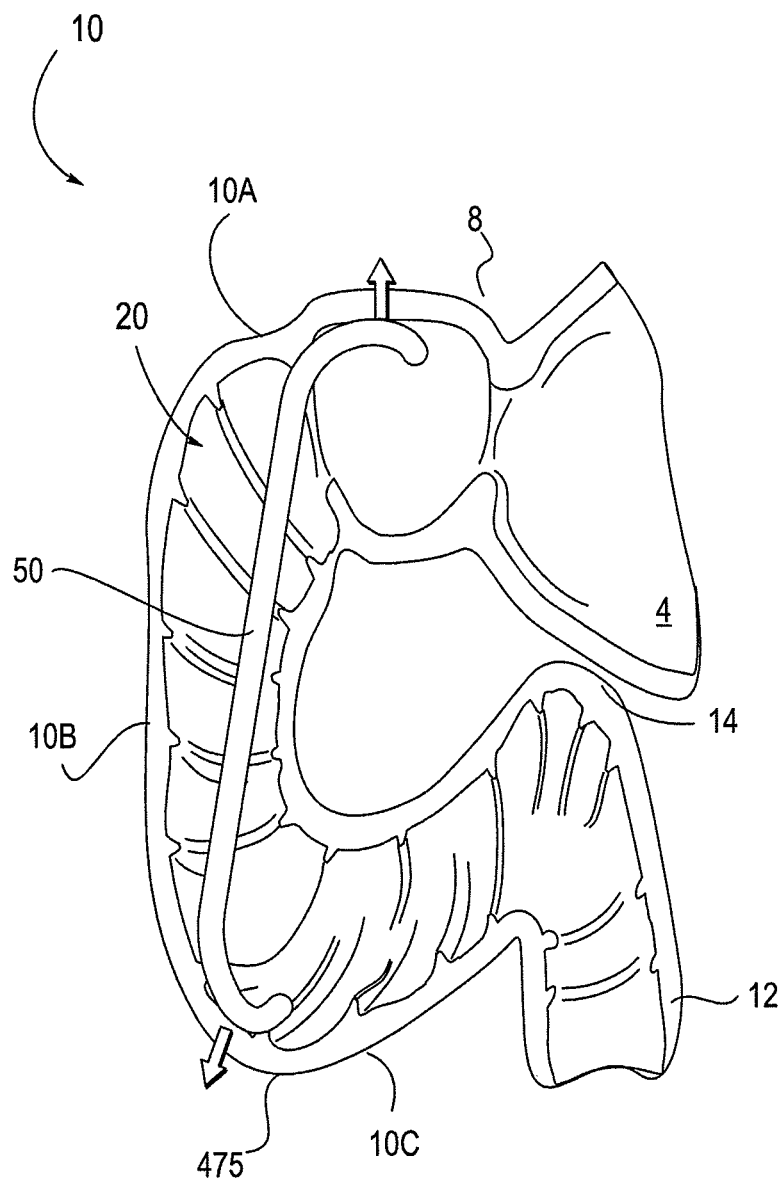
FIG. 38 provides a view of conformationally-stabilizing device similar to that of FIG. 37, with a relatively long central portion, but with proximal and distal portions that terminate well within the duodenum, and an outwardly deflecting bias that alters the shape of the duodenum by distending it along a cephalad-caudal axis.

In some embodiments, device corresponds to the intestinal target location, particularly with regard to an angled site, and the segments or lengths of the device on either side of the angle within the residence site, but may vary in terms of the exactness of the matching of the respective angles of the device to that of the target site. For example, some embodiments have a resilient bias that is outward, or angularly more expansive than the native intestinal site configuration as illustrated in FIG. 37. Other embodiments may cause localized distention of the duodenum as illustrated in FIG. 38. Other embodiments may have a resilient bias that is inward, or angularly more acute than the native intestinal configuration. Still other embodiments may have a resilient bias that is nearly congruent with the native intestinal site configuration. And in devices with angles that correspond to one or more angles in a duodenal residence site, some device angles may be more obtuse and some angles may be more acute than the angle to which they correspond. In another aspect, changes in the shape of devices as affected by changes in angles can also be understood, in some cases, as varying the lengths of segments or varying the lengths of particular curvilinear portions. The length of the central segment or portion of the device shown in FIG. 38 is lengthened in comparison to the analogous portion of the device shown in FIG. 37, and such lengthening changes the shape of the duodenum in which the respective devices reside.

In any of these embodiments where the angles or segments (or portions of a curvilinear section) of the device vary with respect to the native angles or segment linear dimensions of the duodenal target site, the device may effect a change on the shape of the duodenum occupied by the device. In typical embodiments that change the shape of the duodenum, the net effect with regard to the conformational stability of the device is to enhance the stability. In some embodiments where the shape of the duodenum is changed by the intraluminal presence of a device, the effect of the change is to serve a therapeutic purpose, such as, merely by way of example, altering the flow rate of chyme through the duodenum. In other embodiments, changing the shape of the duodenum my benefit the duodenal wall by either the compression or the distension of local regions of the wall that may be associated with an overall shape change. In one example, the device may provide localized distention sufficient to trigger a response from the duodenum, such as activation of stretch receptors and the associated triggering response.

In still another example, an extension, distension, or mild stretching of a luminal wall may benefit the vascularity of a particular region, or generally serve to protect or promote the healing of a region that has been injured or compromised. In another example, altering the shape of the small intestine may facilitate the emptying of the afferent loop in a patient with afferent loop syndrome. In another example, a conformationally stabilizable stent could facilitate the anastamosis process for the roux limb in a Roux-en-Y gastric bypass procedure.

Other embodiments of the invention produce a duodenal shape-change by pinching, clamping, or otherwise applying device end-to-end appositionally-directed force on a residence site or portion of a residence site in the duodenum. In addition to such changes being directed toward a therapeutic end, as mentioned above, duodenal shape-changing embodiments of the device also may advantageously contribute to the conformational stability of the device in the target site. In one shape-altering embodiment of the conformationally-stabilizing inventive device described by FIG. 35, the proximal segment of the spine is configured to reside in the superior duodenum, while the distal segment resides near the duodenojejunal flexure. The spine has sufficient force, more so than the shape-corresponding designs already described, such that the duodenum is altered in shape. This particular embodiment does not have flow reduction elements, but is otherwise similar in length and placement to the embodiment depicted in FIG. 44, and as shown in a residence site in FIG. 47.

Figure 35:
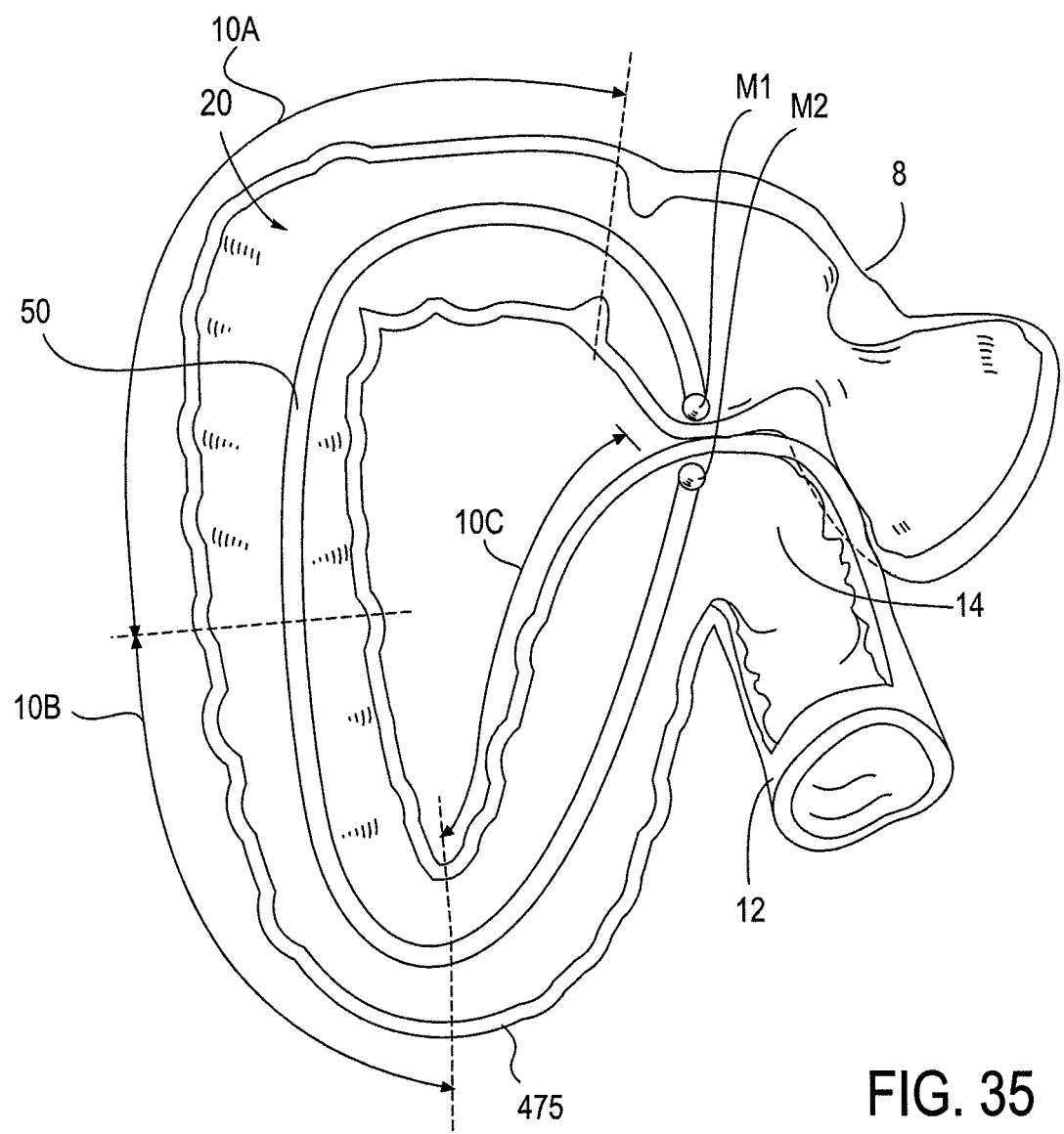
FIG. 35 provides a view of a conformationally-stabilizing device that may alter the shape of the duodenum, the proximal segment resides in the superior duodenum and the distal segment resides near the duodenojejunal flexure, the proximal and distal ends of the device configured to be in close apposition.
Figure 39:
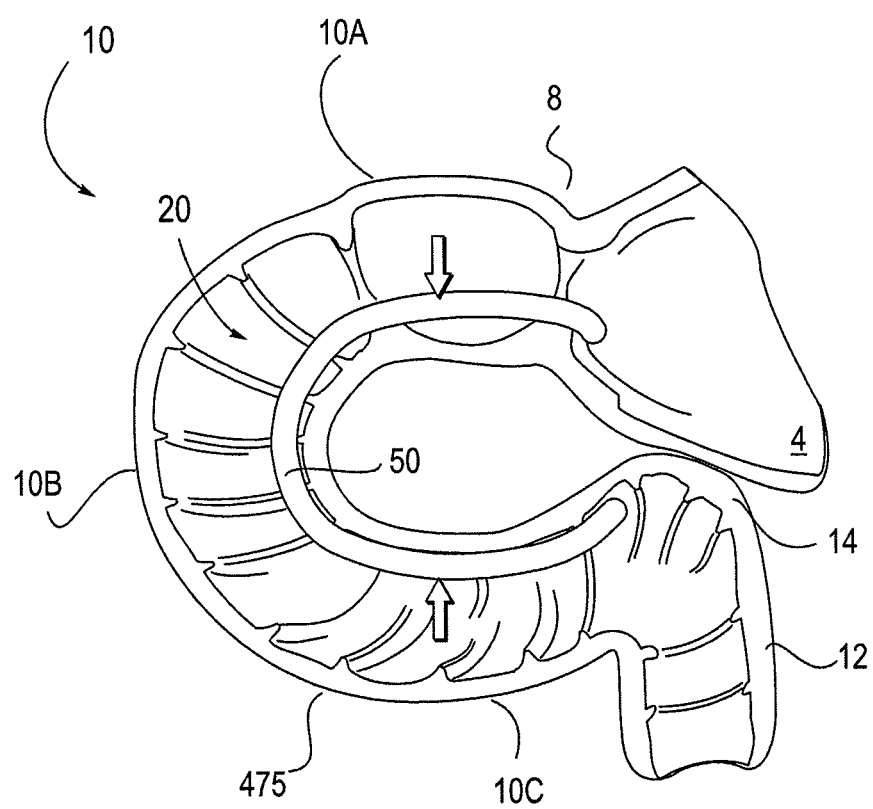
FIG. 39 provides a view of conformationally-stabilizing device comprising a curvilinear elongate body with an acute central angle, and a proximal end terminating just distal to the pylorus and a distal end terminating just proximal to the duodenojejunal junction.

Another such duodenal shape-changing embodiment includes a clamping duodenal insert. If the duodenum is depicted simply as a C-shaped organ, the effect produced by a clamping duodenal insert is the general movement of the duodenum into a partially closed C-shape dictated by the shape of the insert as illustrated in FIG. 39. Magnets may be used to maintain the position of the clamped insert. As shown in FIG. 35, magnets M1 and M2 are positioned in the ends of the device. The magnetic field between M1 and M2, or between a magnet and magnetic material may be adjusted to produce the desired degree of alteration in the duodenal shape. Adjustment of the magnetic field can be used to vary the distance between the ends of the device and shape altering characteristics of the device. Depending upon the anatomical features in a residence site, the device ends or other magnet locations remain in proximity but are not in contact as a result of the strength of the magnetic field. In some cases, it may be desirable to have the magnets pull together completely so that only the tissue of the residence site separates the magnets as shown in FIG. 35. Optionally, the magnets may not be needed, and the device alone may be used to alter duodenal shape as shown, for example, in FIG. 39.

Clamping may also be localized such as where the duodenal angle produced by an angled portion of an insert grasps or secures the duodenum within the clamping angle. Pinching refers to the effect caused on a residence site by when the ends of a partially closed C-shaped insert are moved towards each other. The result exerts an overall pinching effect on the duodenal C-shape and results in a portion of the duodenum or the residence site positioned between the ends of the insert. In some embodiments, a pinching insert moves the ends of the general C-shape toward a nearly O-shaped configuration. Pinching embodiments include: ends of insert come towards one another; ends of insert contact through a portion of the residence site; ends of the insert draw a wall of the stomach into contact with a wall of the duodenum; one end in stomach and the other end in the third or fourth portion of the duodenum; one end in the duodenal bulb and the other in the third or fourth portion of the duodenum. In some embodiments, the ends or portions of the insert could be joined magnetically through the walls of the residence site to other portions or the end of the insert. In one embodiment, the ends of the insert are on opposite sides of the stomach/duodenal wall.

Some of these embodiments may advantageously include extensions or portions of the device that extend either proximally from the duodenum, as into the pylorus, or as in further to the antrum of the stomach, or, alternatively, extending distally beyond the duodenum, and into the jejunum. An example of an embodiment that extends beyond the duodenum is provided by FIG. 36, where the proximal portion of the conformationally stabilized device projects through the pylorus and into the antrum of the stomach, and the distal portion extends into the duodenal-jejunal flexure. An advantage that may be associated with the inclusion of device portions that extend beyond the duodenum (in either the distal or proximal direction) is that such portions may create an overall shape that allows for an increased curvilinear retaining force in general, and greater leverage, if the device is configured to change the shape of the resident site.

Conformationally-Stabilized Devices Targeted to Other Gastrointestinal Residence Sites Embodiments of the present invention have been shown and described with relation to the duodenum. Conformationally stabilized inserts of the invention are not so limited and have application into other residence sites within the body. Moreover, embodiments of the conformationally-stabilized intraduodenal device as described herein may be understood as an example of devices that are configured to conformationally stabilize at other sites in the gastrointestinal tract. In typical embodiments, residence sites include a portion with at least one curved aspect. In one alternative, the curved aspect is provided by the native anatomical curvature of the mammal anatomy. In general, the shape of a portion of the device will conform to at least one anatomic curvature within at least one resident site. Embodiments of the devices described herein may be configured, designed and shaped to conform to more than one residence site. Devices as described herein may be used for providing therapy of any kind, not necessarily directed toward obesity or metabolic disease.

Examples of various sites in the gastro-intestinal tract that have a particular configuration that provides an appropriate residence site for use with a conformationally stabilized device include, but are not limited to: 1) the esophago-gastric junction, 2) the first to second duodenal transition, 3) the duodenal "C", as described in this patent application in detail, 4) the duodenojejunal flexure point, 5) the terminal ileum, 6) the right colic hepatic and left colic splenic flexures, and 7) the sigmoid colon.

Figure 40:
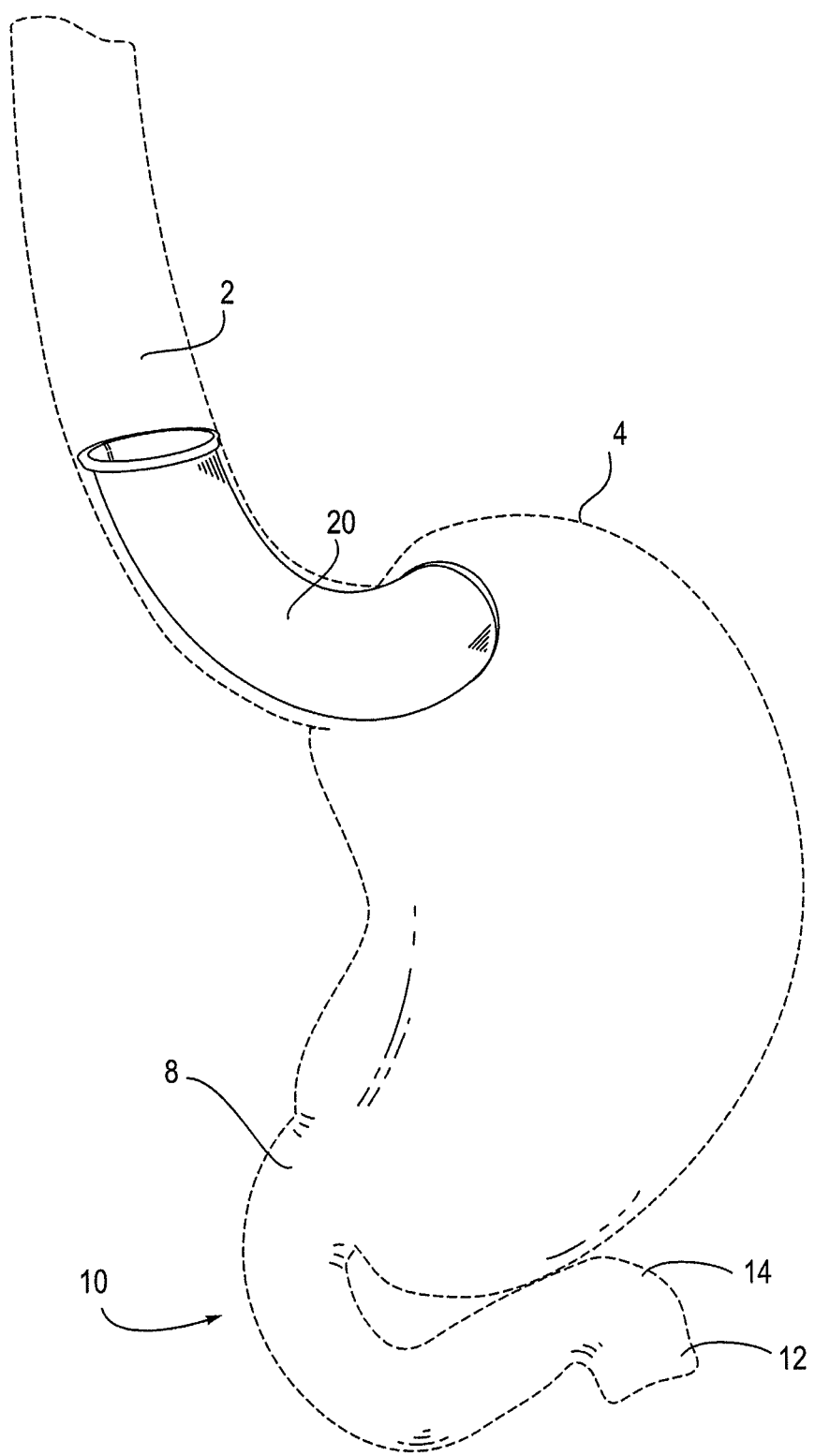
FIG. 40 provides a view of a conformationally-stabilizing device at non-duodenal residence site, within the inferior esophagus and conforming to its curvature.

The unique shape of an esophageal-gastric junction or esophageal residence site is formed when the distal esophagus meets the proximal stomach as it goes posterior to anterior in an almost horizontal component of the cardia while transitioning through the diaphragm. The general direction of the esophagus is vertical, but it presents two or three slight curves in its course. At its commencement it is placed in the median line, but it inclines to the left side as far as the root of the neck, gradually passes to the middle line again, and finally again deviates to the left as it passes forward to the esophageal opening of the diaphragm. The esophagus also presents an antero-posterior flexure, corresponding to the curvature of the cervical and thoracic portions of the spine. It is the narrowest part of the alimentary canal, being most contracted at its commencement and at the point where it passes through the diaphragm. The curvatures of the esophagus provide residence sites for placement of a conformationally stabilized device FIG. 40 illustrates the placement of a conformationally stabilized device within or in proximity to an esophageal-gastric junction resident site, to which it conformationally corresponds. The device 20 can be seen placed in the curved inferior portion of the esophagus 2, the portion prior to gastrointestinal tract opening into the stomach 4. The device is configured in a stent-like manner, pressing radially outward against the wall of the esophagus. The combination of curvature and the radially-outward force prevents distal or proximal movement.

Figure 41:
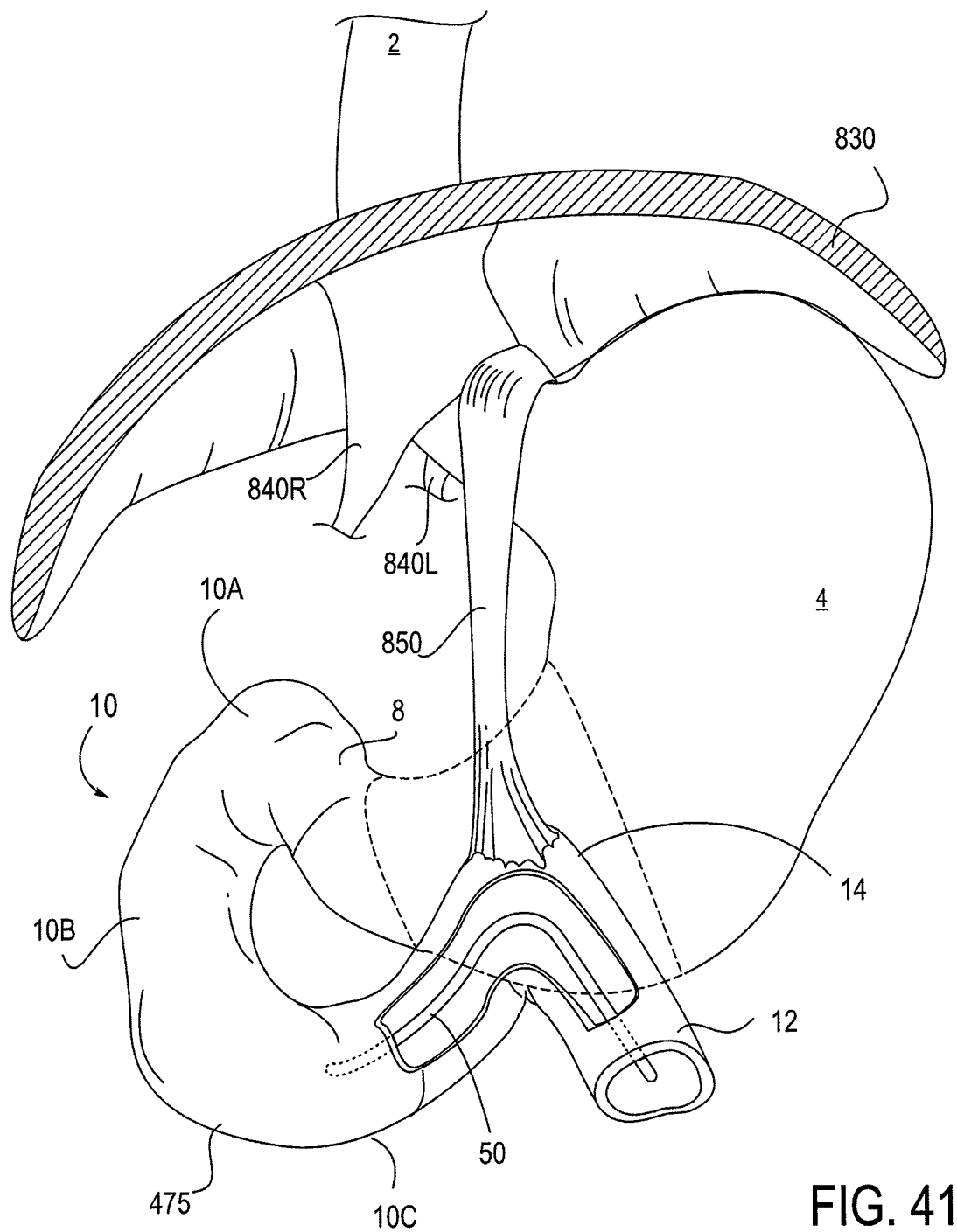
FIG. 41 provides a view of a conformationally-stabilizing device in residence at the site of the duodenojejunal flexure, the device being curvilinear with an acute central angle that conforms to the flexure.

FIG. 41 shows an anterior view of a conformationally stabilized device consisting only of an unadorned spine 50. The device is conformationally stabilized within a resident site located at the duodenojejunal flexure 14 region of the duodenum 10. This unique inverted 'U' shape of the duodenum and flexure is held in place mainly by the Ligament of Treitz 850 and the dropping jejunum 12 that distally follows the duodenum. The Ligament of Treitz 850 is generally supported by the diaphragm 830 and the right crura of the diaphragm 840R and the left crura of the diaphragm 840L.

Figure 42:
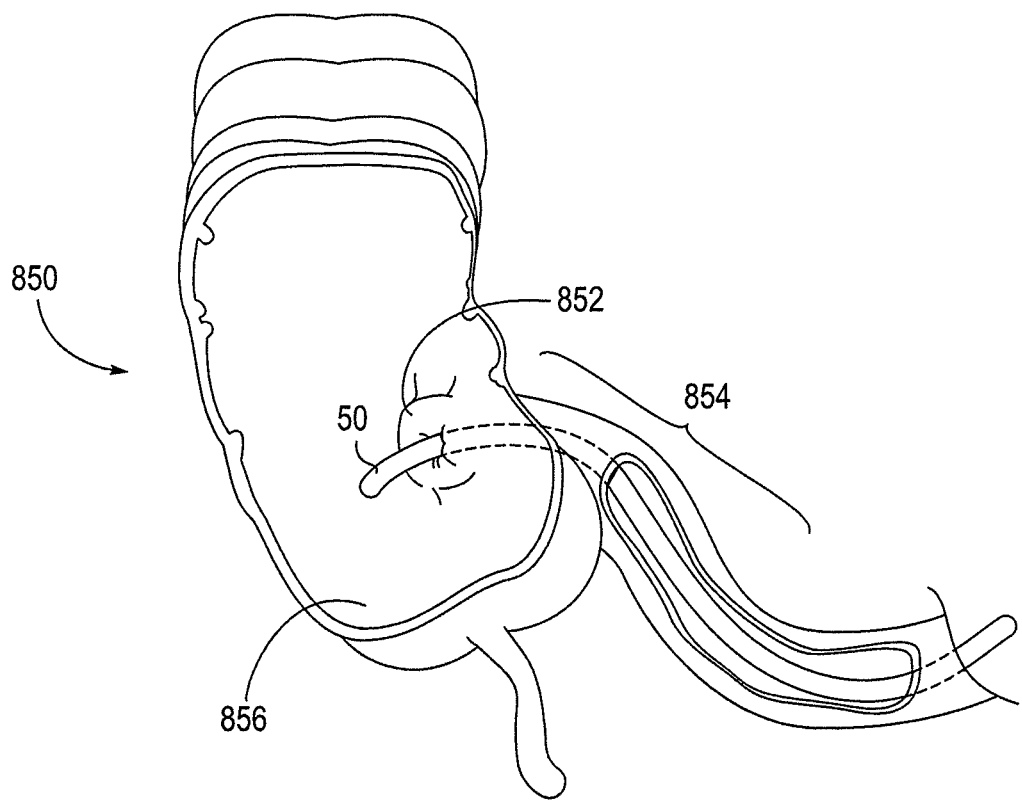
FIG. 42 provides a view of a conformationally-stabilizing device at non-duodenal residence site, the device being curvilinear and residing at site at the junction of the colon and the terminal ileum, the central portion of the device extending through the ileal orifice, the device as a whole conforming to the curvature of the residence site.

FIG. 42 shows an anterior view of conformationally stabilized device having a spine 50. The device is conformationally stabilized within a terminal ileum 854 resident site, penetrating the ileal orifice 852, entering into the ascending colon 850 in the general vicinity of the cecum 856. The unique residence site shape here is formed by the distal ileum just before the junction of the colon, and terminates in the ileocecal valve.

Figure 43:
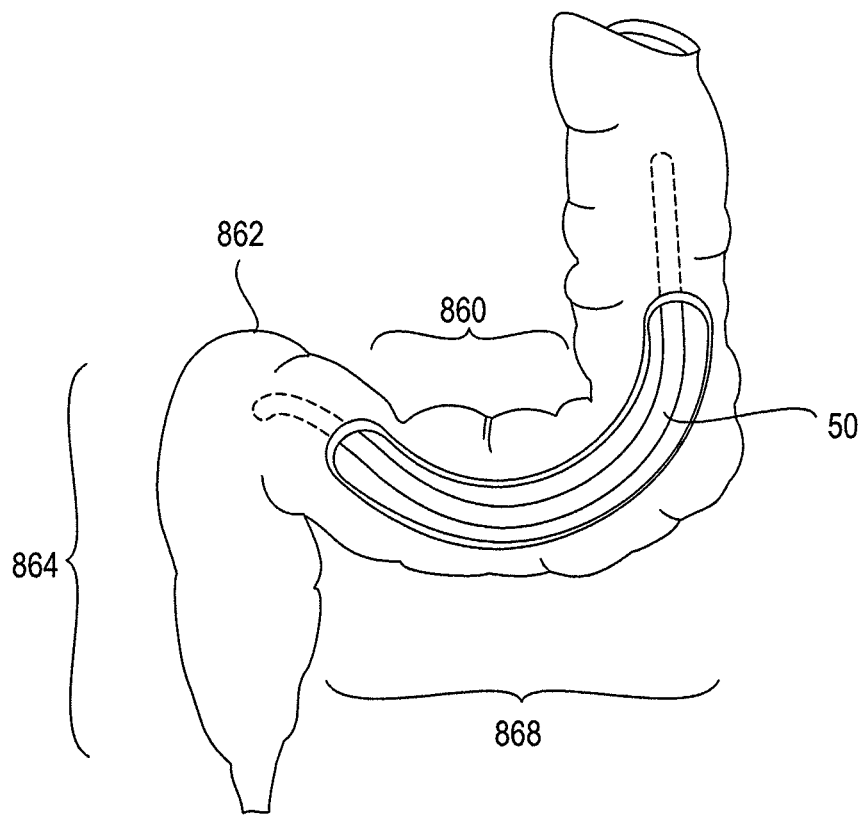
FIG. 43 provides a view of a conformationally-stabilizing device in residence at the site in the sigmoid colon, the device being curvilinear with an oblique central angle and overall length that conforms to the residence site.

FIG. 43 shows an anterior view of a conformationally stabilized device having an unadorned spine 50. The device is conformationally stabilized within a sigmoid colon resident site 868, centered around the sigmoid mesocolon 860. This unique resident site is formed by the distal colon as it approaches the rectum, just proximal to the rectosigmoid junction 862. The resident site is held in place primarily by the surrounding structures, such as the sigmoid mesocolon 860. Although there are variations in patient anatomy with respect to the shape of this anatomical site, it is typically sigmoid in shape.

The preceding series of illustrated residence sites for conformationally-stabilized embodiments of the device in the gastrointestinal tract is not intended to be limiting. Other sites, including, for example, the transition portion of the first to second duodenum, as it courses retro-peritoneal from anterior to posterior, and the hook-like shape it takes on as through the peritoneum, and/or the right colic hepatic and left colic splenic flexures, which include curved portions that typify suitable residence sites, as described above. Additionally, residence sites may be located in various ducts that empty into the gastrointestinal tract. Exemplary but not limiting examples of such ductal sites include the bile duct and the pancreatic duct.

An Intraduodenal Conformationally-Stabilized Device with a Proximal End Terminating in the Gastric Antrum and a Distal End Terminating Near the Duodenojejunal Junction Some embodiments of the devices described and depicted herein generally match, correspond, or conform to the anatomy of the duodenum, and gain a positional stability within the duodenum from that relationship. Positional stability of the device provides resistance to movement relative to the gastrointestinal tract. The device is stable against nutrient flow and peristalsis (both in the downstream direction) and regurgitation (upstream direction). Some embodiments (FIGS. 3, 7, and 8) additionally rely on an anchoring mechanism, a portion adjunct to the major duodenally-residing portion of the device which extends upstream from the duodenum, proximally through the pylorus. The anchoring portion is of a size and configuration that prevents its movement through the pylorus, and thus it anchors the device as a whole. Other embodiments, in addition to the enjoying the stability provided by generally conforming to the duodenal residence site, derive further positional stability from a clamping or distending of the device within the duodenal residence site (FIGS. 32A-35, 37-39). In some instances, this contributes to positional stability because the shape of the device makes the device less amenable to being passed downstream. In some these instances (FIGS. 38 and 39, in particular), the device may alter the shape of the duodenum, thus making the device less likely to being passed downstream in that way as well.

The device embodiments illustrated in FIGS. 36 and 44-51 not only conform to the duodenal residence site, but engage the gastrointestinal tract in a manner that particularly contributes to positional stability in the duodenally-centered residence site. Embodiments of devices described in this section may generally be characterized as having a proximal end that terminates in the gastric antrum, and a distal end that terminates in the region of the duodenojejunal junction, where the Ligament of Treitz is a landmark external to the duodenum. Embodiments in this section (FIGS. 44-51) may also be generally characterized as having a central curved portion that is configured to conform to a duodenal lumen between the proximal and distal ends. The device further may be characterized as being stabilized in its residence site substantially by the fact that its conformation accords with the conformation of the residence site. Embodiments of the device typically do not have any piercing elements that attach to the gastrointestinal wall for securing the device within the site. Further, embodiments of the device, and particularly embodiments of the portion of the device that resides proximal to the pylorus are typically able to freely pass through the pylorus, such that the device does not have an anchoring mechanism that depends on the pylorus as a pass-through restraint.

It is to be appreciated that other earlier described devices may be modified to include one or more aspects of conformal stabilization. Embodiments of the devices described herein are modified to configure a specific embodiment of a device to have the curved central portion that at least partially conforms to a portion of or all of a residence site along with proximal and distal ends that, in use, are near or in proximity to one another. Those of ordinary skill will appreciate that the devices may be modified by lengthening or adding a curved central portion of desired geometry, modifying or adding proximal end or distal ends or other changes according to the specific characteristics of the device and the targeted residence site.

Conformationally-stabilizing devices, as particularly illustrated in FIGS. 44-51 provided herein include features that are particularly configured so as to be advantageous toward an objective of providing safety, conformational stability, and performance to a device as it resides in the duodenum. Other features relate to the ability of the device to have two configurations and the ability to easily transition from one to the other. The two basic configurations are: (1) a stowable configuration for accommodation in the working channel of an endoscope, or within a sheath that can be delivered endoscopically, and (2), a deployed configuration for functioning once the device is situated in a residence site within the gastrointestinal tract. These features relate to numerous aspects of the device, as, for example: the elongated member of spine of the device as a whole, end portions and end features of the spine, a unitary construction, a shape memory alloy composition, an end-end crossover design, the length of the device, a thermoplastic polymeric coating, and the composition and configuration of the braid of a flow reduction element. These features and the particular benefits derived there from are described in detail, below, and then followed by a description of exemplary embodiments as shown in FIGS. 44-51.

The end portions of the spine of embodiments of the device are generally tapered prior to a terminal expansion into bulbous features, as described below. This tapered aspect of the spine of the device allows for a relatively thick central portion that provides for sufficient stiffness to hold an angle that stabilizes the device in the duodenum. The diameter of the central curved portion of embodiments of the device typically ranges between about 0.025 inch and 0.055 inch; the diameter of some embodiments range between about 0.036 inch and 0.046 inch, and the diameter of particular embodiments is about 0.042 inch. The stiffness allows the device to have a tight central radial aspect, while the device as a whole nevertheless has an elasticity from the material properties of its alloy composition (described below) that allows it to straighten out for accommodation in an endoscope. The smaller diameter end portions that taper from the thicker central portion are advantageously more flexible. Each of the tapered end portions transition into a coil end, and ultimately culminate in a bulbous feature, both as described further below. The relative flexibility associated with the narrow diameter end portions, the coils, and the bulbous end features all contribute, advantageously, to a safe and atraumatic end to the device.

The end-portion tapering of embodiments of the device is preferably accomplished by uniform radial reduction in dimension, rather than by chamfering. The uniform radial reduction precludes the formation of a discontinuous transition point, in specific contrast to a chamfered tapering, which could create a point of weakness or bending vulnerability. The smaller diameter of the tapered ends permits a high degree of flexibility that allows the tight-radius coil ends to straighten out for accommodation in the working channel of an endoscope.

The shape of each of the two ends of device embodiments has features that contribute to an atraumatic configuration that precludes irritation or injury to the lining of the gastrointestinal tract. Coils formed from or on the terminal end portions of the spine or elongated body are used as atraumatic features. Coils may refer to the shape of the distal end of the device or to the type of wire formed added to or taken by the elongate body. An end-point of the diameter of the tapered end-portion of the device, even if on a coiled end, that is merely blunted could still too sharp for atraumatic contact with a gastrointestinal wall. An exemplary form of a soft or atraumatic end feature is a bulbous tip, although other features that present only smooth surfaces and oblique angles to a tissue surface may serve the same purpose, and are included as embodiments of the invention. Thus, the diameter of the end point of the device may be increased from the tapered diameter of the end portions to assume a generally bulbous, ovular, ball-shaped, or spherical form, with a diameter in the same range as that of the central curved portion of the device. The bulbous form also provides a stop-surface or shoulder against which the Hytrel® coat (see further detail below) abuts from its central portion. This center-biased confinement advantageously serves to stabilize that Hytrel® in place, preventing slippage of the coating from the center toward either of the end points of the spine of the device.

Other types of atraumatic ends, alternatives to coiled ends, are depicted in the Figures and described in greater detail below. Briefly, however, these atraumatic end features may include polymeric shape memory components that can assume a linear form for deployment, but expand in a lantern-like manner upon release from the linear constraint of an endoscope working channel. In other embodiments, a braided mesh bumper, similar to the flow reduction element is bonded to the ends of the device, and can assume a linear form for deployment and assume radially-expanded form once released from being stowed in the endoscope. In another embodiment, the atraumatic end features are paddle- or spoon-shaped. These end features offer the advantage of presenting a substantially flat or shallow convex surface that distributes force over a wide area against the wall of the gastrointestinal tract. The substantially spoon-shaped end features, being composed of a resilient or shape-memory material, have a rollable bias that allows them to be compressed into a substantially linear stowable configuration that unrolls into the spoon shape as the device is released from the constraint of an endoscopic working channel or a holding sheath. In some embodiments, the composition may include Nitinol or an alloy with similar properties, or alternatively a resilient polymer, or a combination such a metal core with as a polymer-coat. Some of these embodiments may be mounted on a swivel mechanism, which facilitates orientation of the flat or convex surface against the luminal wall.

The spine of a typical embodiment of the device is formed from a single piece of alloy, and in some embodiments, the unitary construction can include the atraumatic bulbous ends, as described above. Single-piece construction is advantageous over multi-piece construction for absence of points of bonding that can fail or be points vulnerable to bending.

The relatively proximal portion of the device residing in the pylorus is typically a portion of the spine of the device that does not include any flow reduction elements; and it is of a sufficiently narrow diameter that the pylorus does not react to its presence. Accordingly, the device is effectively invisible to the pylorus. The invisibility of the device is further supported by the smooth surface presented by a Hytrel® coating (see below). The blindness of the pylorus to the spine of the device advantageously allows normal and desirable functioning of the pylorus.

Embodiments of the device are typically encased in thermoplastic polyester elastomer, such as Hytrel® (Du Pont Engineering Polymers, Wilmington, Del.). The Hytrel® material is applied to the device as a tube fitted over the spine, thus forming a single unitary outer layer, without bonding sites that could be vulnerable to failure. The Hytrel® tubing covers the entirety of the Nitinol spine, even over-lapping the ends. In the process of manufacture, the tubing, once fitted over the Nitinol core, is heated to sufficiently melt, shrink and seal it as a skin around the metal. Other methods of applying the Hytrel®(t to the metal core (included as embodiments of a method of making the device) include dipping the metal core into molten Hytrel, or spraying Hytrel® on the metal through a deposition process. This application of Hytrel® creates a sealed environment for the Nitinol, which protects it from the corrosive environment of the stomach. The Hytrel® covers the tapered Nitinol sections as well, further contributing to device safety as it protects the thinner Nitinol from being over stressed by providing a flexible and resilient buffering layer that distributes any point-specific strains over a broader region, similar to a strain relief.

Embodiments of the device include a shape memory alloy such as Nitinol as a primary component of the composition, which provides the device a flexibility that allows easy and atraumatic accommodation in the gastrointestinal tract. The flexibility or superelastic feature of Nitinol further supports the ability of the device to assume the straight configuration required for placement in the working channel of an endoscope, and to assume the curved deployed configuration when released from the constraint of the working channel. When the Nitinol surface has been appropriately finished, its surface has exceptional corrosion resistance. The Nitinol surface is substantially covered by the Hytrel® coating, but the properties of the Nitinol surface provide a fall back layer of corrosion resistance in the event of any compromise of the Hytrel® coating.

Each of the two ends of embodiments of the device forms a lever arm with respect to the center of main section, and thus with increasing lever arm length, less force is required to displace the end of the device with respect to the center. As there are constraints on device diameter, the formed shape or preferred shape of the device can be varied to accommodate a variable length of the device. From the perspective of the effect of the device on the gastrointestinal tract, approximately the same amount of appositional force from the ends of the device is desirably applied to the two ends of the resident site, regardless of the length of the lever arm. Thus, for example, one embodiment of a device with a relatively long length (e.g., greater than about 35 cm) is one in which the end-end crossover dimension is relatively large (FIG. 46A), in contrast to shorter devices (e.g., less than about 25 cm), in which the end-end crossover dimension is relatively small (FIG. 46B). The relative amount of crossover (in addition to the overall length of device) is a feature that can be varied, either in terms of a range of product options, or as a patient-specific custom fitting. Thus, by way of example, a patient with a ligament of Treitz that is located a relatively short distance from the gastric pylorus might be provided a device with a preferred configuration that has a relatively small amount of or even no end crossover. Devices that vary with regard to their preferred configuration or the amount of end-end crossover can be characterized in terms of "separation force" or "native resiliency", as these are the metrics that interact with tissue.

Embodiments of the device have an appropriate length that to a considerable degree corresponds to the minimal length required to prevent its distal migration into the colon. Such appropriate length may range between about 32 cm and 52 cm; some embodiments have a length that ranges between about 35 cm to 43 cm; and particular embodiments have a length of about 39 cm. These lengths may be considered broadly appropriate for human patients, however, embodiments of the invention include custom fitting of devices to individual patients, and accordingly, the appropriate length of the device, as determined by anatomical landmarks (as described below), can vary according the gastrointestinal anatomy of the individual patient. This length is measured from the distal and proximal points of the device where the tapered portion begins, prior to the transition into coiled end features. This length corresponds to the designated residence site of the device in the gastrointestinal tract, a site spanning the duodenum and having the proximal anatomical landmark at the gastric antrum and the distal landmark of ligament of Treitz, in the region of the duodenojejunal junction.

The reason the device stabilizes in the duodenum is that this resident site spans two points where the anatomical position is fixed, thereby holding the duodenum in a particular shape, unlike the rest of the small intestine which has a general freedom of conformational movement. These fixed points are, respectively, in the proximal duodenum, where the duodenum goes retroperitoneal, and in the locale of the duodenojejunal junction, just distal to the fourth portion at the suspensory Ligament of Treitz. Once the device is situated in the residence site, the proximal and distal coiled ends are in substantial apposition with each other in spite of the curvilinear intraduodenal distance that separates them. The gastric antrum and the duodenojejunal junction, though at some distance from each other along the length of the gastrointestinal tract, are close together because of the overall configuration of the gastrointestinal tract (see, for example FIGS. 36, 47, and 51).

The values for the appropriate and minimal length of the device were a consensus result of a number pieces of data, including standard anatomical references, published studies, a computer tomography scan data of 12 patients that was compiled into a three-dimensional model, fluoroscopy measurements of a single patient with a wire placed in the Ligament of Treitz to a nearby point in the gastric body, autopsy data of a patient unrelated to study of the invention, resected duodenum measurements of a patient (unrelated to study of the invention) who had undergone a pancreaticoduodenectomy, and X-ray images of 12 patients showing a 25 cm embodiment of a device of the present invention that had been placed in the resident site.

Some embodiments of the device include chyme flow reduction elements that may have any of a variety of forms; see FIGS. 44-48, and 51 (as well as earlier examples, as in FIGS. 16-23) and further detailed description below. A considerable amount of description will be devoted to detailing aspects of the flow reduction elements, because these are important features for the embodiments that include chyme flow reduction as an objective. Some embodiments of the invention, however, may not have that as an objective. Some embodiments, for example, may be directed to providing a platform for the release of bioactive agents, or for providing a platform for neuronal stimulation. In such embodiments, flow reduction elements may not be included, and the profile of the device may be substantially bare compared to the embodiments that include the flow reduction elements.

Returning to description related to particular embodiments of flow reduction elements, some flow reduction elements include braided forms that collapse to substantial linearity around the spine when in a stowed configuration within the working channel of an endoscope, and open into radially expanded form, their preferred configuration, when ejected from the working channel and deployed at the residence site. These flow reduction elements may be formed by braids of polymeric material, such as polyamides, or nylon, or any suitable material. The elements may be generically referred to as spheres, but may assume any of a variety of angled forms. The number of braided flow reduction elements may vary according to the length of the device and to other variables related to the dimension and spacing of the flow reduction elements, but typical embodiments include a number of elements that ranges between 1 and 10 elements per device, the range in some embodiments is between 2 and 8, and particular embodiments include between 3 and 7 flow reduction elements per device. Also, however, some embodiments may include a long single flow reduction element, or an embodiment may have a plurality of short elements placed closely enough together so they would functionally act a single flow reduction elements.

The flow reduction braid surrounds the portion of the spine where it resides; it is attached or fused to a site on the distal portion of the device, near the beginning of the tapered end portion. The braid is otherwise not attached to spine and can slide freely, within limits, up and down the spine in a coaxial manner. The limits of slidability include the overall length of the braid; using the proximal end of the braid as a reference point, the proximal end can extend proximally only so far as the length of the braid permits, whereupon the braid is substantially linearized around the spine, and there is no longer any lengthening slack from radially-expanded segments of the braided flow reducing element. Braid sliding is also limited in the distal direction by a stopper feature that constitutes a fused radial stop piece located at the approximate midpoint of the spine, within the space bounded by the surrounding braid. The force of the downstream flow of chyme can tend to push the braid, more particularly the expanded segments of the braid in the downstream or distal direction. The degree to which the flow reduction element segments are pushed distally is a result of the sum of the downstream force of the chyme and the countervailing stiffness of the braid. However, it does not serve the function of the device for the braid to be pushed to a distal extreme, and such movement could cause a janning of the braid and consequent blockage (rather then impedance) of chyme flow. Thus, the function of the stopper feature is to prevent distal movement of the braid beyond a point where the flow reduction function is served.

The relative level of stiffness or compliability of the flow reduction elements is affected by a number of variables. With stiffer plastics (e.g., polyethylene terephthalate or nylon), braided radially-expanded forms are more resistant to radial compression, whereas with softer plastics (e.g., low density polyethylene or low-durometer Pebax) the flow reduction elements radially compress more easily. The resistance to compression also relates to the resistance that the flow reduction elements provide to the downstream flow of chyme through the duodenum.

The number of filaments used in the braid also relates to stiffness of the braided flow reduction elements, as the use of more filaments increases the overall stiffness of the flow reduction element, and the resistance to compression or yielding to chyme flowing downstream. The diameter of the filaments used also impacts the stiffness of the flow reduction elements: thicker individual filaments impart greater stiffness to the braided flow reduction element.

There are a number of variables in the construction of the braid used for the flow reduction elements that impart performance features to the braided flow reduction element. For example, expansion of the spheres is maximized by choosing a picks-per-inch value that allows for maximum angular movement of one braid strand with regard to another. By way of further explanation, a pick in braiding parlance refers to the point where one fiber crosses another. Thus, with increasing picks per inch, the braid becomes denser and stronger. Further, however, as braid becomes more dense, the radial vector of braid length increases with respect to its axial vector, and accordingly the braid becomes less able to radially expand because it already has a radial configuration. Thus, picks-per-inch becomes a parameter of significance in determining the radial expandability of the braided flow reduction elements. Exemplary braid embodiments include a picks-per-inch value range between 8 and 16 picks-per-inch; some particular embodiments have about 13 picks-per-inch.

Sphere expandability is also a function of the size of the mandrel over which the braid is formed. For example, braiding over a mandrel of infinitely small diameter ("braiding over air") maximizes expandability. This approach creates a braid with the most acute angle of one strand with regard to another when in a compressed state, thereby allowing maximum angular movement when in an expanded state. Sphere expansion is one of the variables that relates to the degree to which the braid effectively prevents or allows the flow of chime through or around it.

Filament size, the number of filaments, and the relative level of filament crossing all also collectively contribute to the total volume of braid per unit length of braid. This total amount of braid volume becomes a parameter of significance when the device as a whole is configured into a collapsed or stowable configuration as it needs to be to be accommodated in an endoscope working channel. The collapsed cross-sectional profile can be understood to have three major components, an inner core of the Nitinol spine, an intermediate layer of Hytrel®, and an outer layer of braid. There is relatively little discretion in the diameter of the Nitinol spine, as that thickness is largely determined to stiffness considerations as described above, and there is relatively little variability in the thickness of the Hytrel® layer, as it is already preferably of a reasonably minimal thickness. Thus, there may be a constraint on the thickness of the Hytrel layer as represented by the diameter of the working channel of the current standard for therapeutic endoscopes, which is about 3.7 mm.

The angle by which the flow reduction form rises from the axial baseline also relates to the relative degree of stiffness or compliance of flow reduction forms. Typical embodiments of braided flow reduction elements are linearly symmetrical (i.e., the distal-facing and proximal-facing angles are the same); although this is not necessarily the case, and embodiments include flow reduction elements that are asymmetrical in this aspect. A relatively steep facing angle such as 45-90 degrees imparts a resistance to radial compression, whereas a relatively shallow angle, such as 1-45 degrees, imparts compliance to radial compression. On the other hand, a relatively steep-facing angle is more susceptible to inversion, or longitudinally collapse in the face of pressure from chyme flowing downstream. And, flow reduction elements that have a shallow facing angle are less susceptible to longitudinal collapse when encountering downstream flow. In sum, accounting for the consequences of facing angles being too shallow or too steep to maintain the integrity of their shape, generally preferred embodiments of the braided flow reduction elements of the invention have a face angle, in their preferred or non-constrained or non-stressed configuration that ranges between about 35 and 50 degrees, more typically ranges between about 40 degrees and 50 degrees, and in some particular embodiments is about 45 degrees.

Another variable in the overall configuration of a device that makes use of braided spheres as flow reduction elements relates to the spacing between the flow reduction forms. Within the length of the device that is occupied by the plurality of flow reduction elements, the relative amount of length occupied by the elements and by the inter-element space can be varied. As relative amount of inter-element space increases, so may increase the amount of chyme being held or slowed by the device. Variation in such holding amount may be reflected by a covarying amount of chyme residence time, and may, accordingly, have an effect on the biochemistry of the chyme and the neural or endocrine response of the duodenum to its content. In other aspects, the amount of neural stimulation that the flow reduction forms provide to the inner wall of the duodenum may relate to the total amount of surface contact, thus, a higher level of surface contact (either flow reduction forms of greater length, or more forms per unit length of the device) could provide more stimulation, and a greater source of input that it perceived as satiety.

Another variable that relates to braid parameters such as filament size and count relates to the degree to which the braid effectively prevents or allows the flow through of chyme. In general, a higher density of braid material (filament thickness, count, and picks-per-inch) creates a higher level of resistance to chyme flow-through, and a lower density of material permits some degree of flow-through. These variables can be adjusted in embodiments of the flow reduction form to achieve different levels of desired flow-permeability. Another feature of the braid material can relate to surface properties. Non-stick surfaces may be relatively permissive of flow through, whereas sticky surfaces may encourage accumulation of chyme that itself tends to clog the pores within the braid, and create impermeability to chyme. In some embodiments, the flow reduction elements may be purposely designed to clog, or the braid may be overlaid with an expandable layer that prevents chyme from flowing through the interior of the flow reduction elements.

During deployment of embodiments of the device, a physician can see device with the visual capability provided by an endoscope as the device emerges from the working channel of the endoscope. In some embodiments of the invention, portions or sites of the Hytrel® coating can be color coded in such a way so as to be informative as to the position on the device that such marking occurs; this allows the physician to know exactly which portion of the device has emerged from the working channel.

Other forms of marking may be included on the device to facilitate placement and visualization of the device once it has been placed in the residence site. Radiopaque markers, for example, may be created by doping certain sections of the Hytrel® with barium sulfate or other radio dense materials. These radiopaque markings may be used to identify particular features of the device with X-ray imaging, such identification and localization can be useful in deployment, retrieval, or to visualize the placement of the device in the gastrointestinal tract.

Some embodiments of the device include feature molded into the Hytrel® coating of the distal end of the device that specifically mates with the delivery system to facilitate device delivery into the gastrointestinal tract. This feature is described further below and shown in FIG. 44.

Other features of the spine and the flow reduction elements relate to deployment and maintenance of configuration once deployed. A pusher feature of the device, for example, provides a proximal-facing and pushable shoulder edge (see FIG. 44) against which the delivery system can push the device distal ward for device delivery from the working channel of an endoscope. The shoulder is adapted such it provides a proximal-facing surface that is sufficiently flat and broad to be able to absorbing the pushing force without allowing an override or slippage, yet configured with sufficient smoothness that the shoulder does not provoke tissue irritation. Such a pusher feature can be molded directly into the Hytrel® coating.

Examples of Duodenal Conformationally-Stabilized Devices with a Proximal End Terminating in the Gastric Antrum and a Distal End Terminating Near the Duodenojejunal Junction Turning now to illustrative examples (FIGS. 44-51) of embodiments of devices and various features, as described above, which have a proximal end terminating in the gastric antrum, a distal end terminating in the region of the duodenojejunal junction, and a central curved portion configured to conform to a duodenal lumen between its proximal and distal ends. The device is stabilized in its residence site because its conformation accords with the conformation of the residence site. Embodiments of the device do not have any piercing elements that attach to the gastrointestinal wall for securing the device within the site, and portions of the device that reside proximal to the pylorus are able to freely pass through the pylorus, such that the device does not include an anchoring mechanism that depends on the pylorus as a pass-through restraint.

Figure 36:
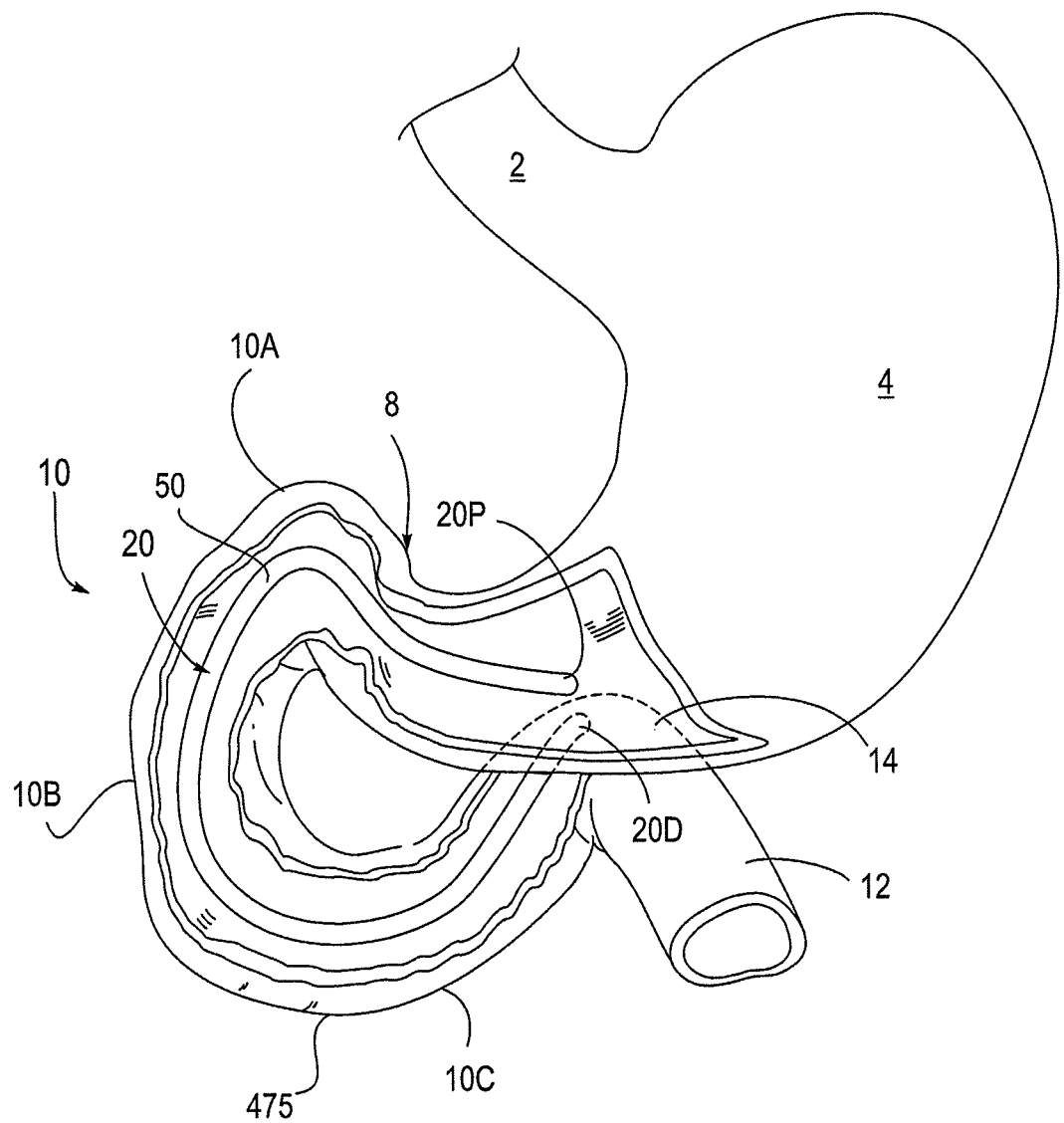
FIG. 36 provides a view of a device with a proximal portion extending upstream from the duodenum, through the pylorus, and into the gastric antrum, and with the distal end extending to the duodenojejunal junction. This device does not necessarily alter the shape of the duodenum or gastrointestinal tract in any substantial way. The proximal and distal ends of the device are in close apposition because the anatomical points where they reside are actually in such close apposition. This particular embodiment does not have flow reduction elements, but is otherwise similar in length and placement to the embodiment depicted in FIG. 44, and as shown in a residence site in FIG. 47.
Figure 44:
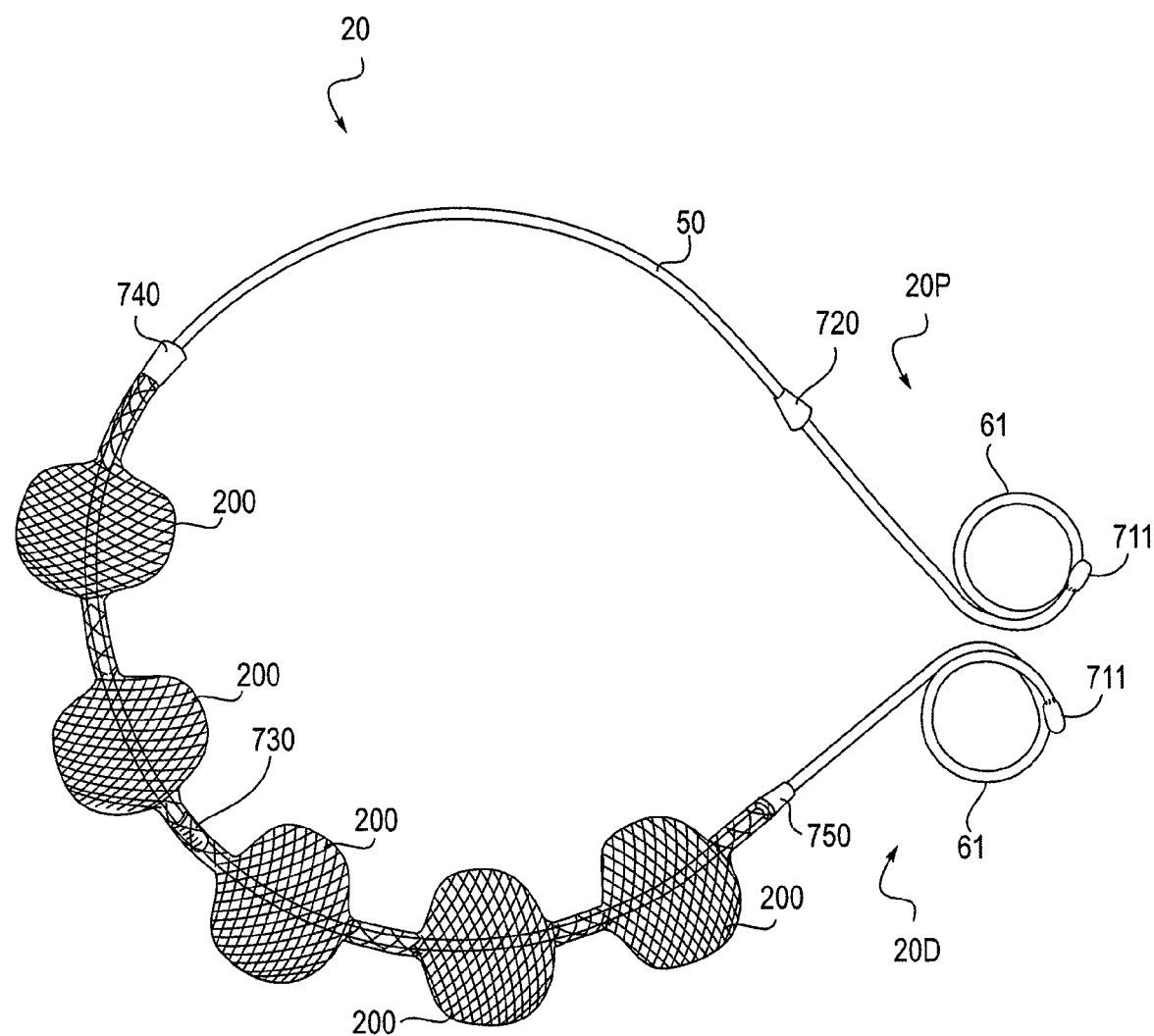
FIG. 44 shows an embodiment of a conformationally-stabilizing device that has a similar flow reduction element as that of the device shown in FIG. 19A, and with a residence site similar to that of the device shown in FIG. 36, with a proximal portion that terminates in the gastric antrum; and the distal portion terminates near the duodenojejunal junction.
Figure 45A:
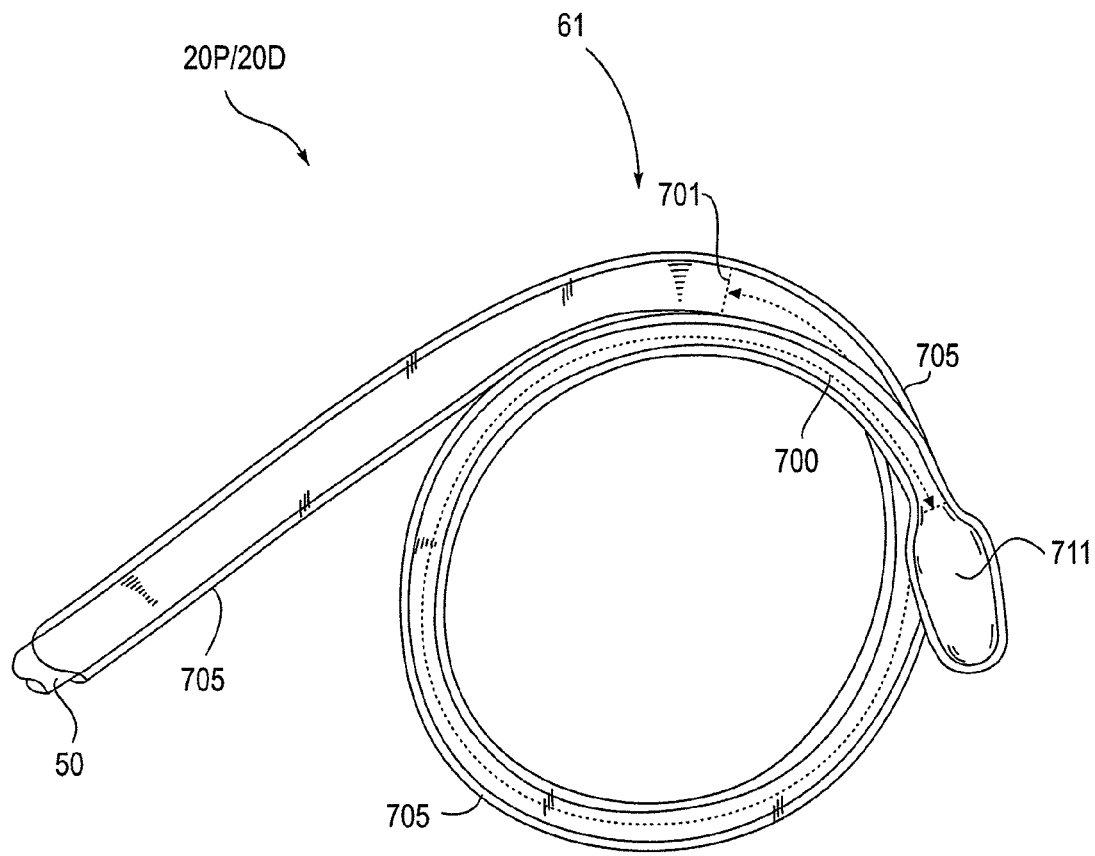
FIG. 45A provides a detail view of a tapered end portion, with a coil feature and a terminal bulbous feature.
Figure 45B:
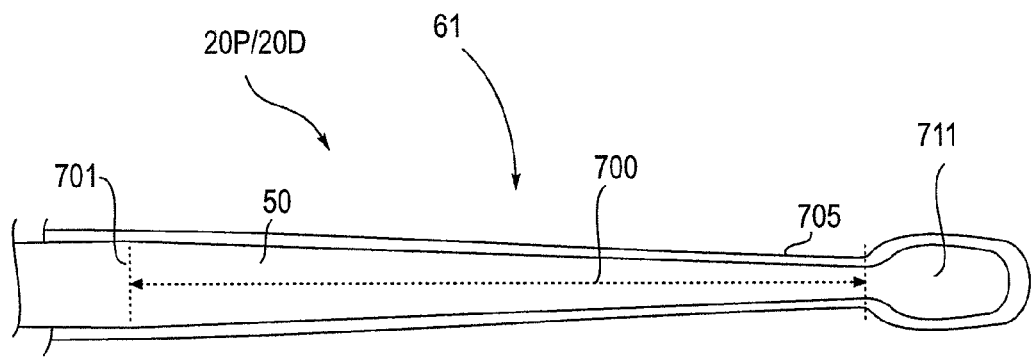
FIG. 45B is the view of FIG. 45A straightened to more clearly show the diameter transitioning regions and the bulbous feature.

FIG. 44 shows an embodiment of a conformationally-stabilizing device 20 similar in the form of its flow reduction element including expandable braided baskets to the device shown in FIG. 19A, and similar in its residence site placement to the device shown in FIG. 36, with a proximal portion 20P that terminates in the gastric antrum; and the distal portion 20D that terminates near the duodenojejunal junction. The spine 50 of central curved portion forms a loop, with the proximal 20P and distal 20D ends coming to be in near apposition with each, and in some cases crossing each other near their termini. In FIGS. 45A and 45B, and as described above, the ends of the device have a tapered portion 700, which starts at a transition point 701 where a radial tapering begins. The end portions include atraumatic features such as coil ends 61, and bulbous end termini 711. The device is depicted into its preferred configuration, i.e., the configuration it assumes at rest. As described above, the devise can be forced into a linear configuration for inclusion in the working channel of an endoscope in preparation for deployment. Once implanted in the residence site in the gastrointestinal tract, the overall configuration of the device approaches the preferred configuration, but is generally slightly constrained. For example, the overall curvature may be made slightly more obtuse, by the counterforce exerted by the gastrointestinal tract on the device.

Also depicted in FIG. 44 is a flow reducing element 200 comprising braided filaments that form a plurality of radially-expanded segments; the braided element is arranged in a coaxial manner around the Nitinol body of the device. The figure depicts five segments, but the number may vary, as described above. The braided flow reduction element 200 is fixed to the device at its distal end, but freely slideable on its proximal end within limits. A proximal sliding movement limit is represented simply by the length the braided element. The slack for sliding comes from the trade-off between radial expansion of the expandable segments and the absolute linear length of the braid as the expandable segments are drawn in. The distal limit on the slideable range of the braided element is provided by slide stopper feature 730. This feature is fused to the Nitinol body and has a radial profile over which the braided element 200, itself, can freely slide, but sufficiently high that it blocks distal movement of an end ring 740 at the proximal terminus of the braided element 200. The purpose of this stop feature 730 is to prevent an extreme distal movement or collapse of the braided element as whole, which could defeat its function (i.e., to reduce chyme flow, not to block it).

Also depicted in FIG. 44 is a pushable shoulder 720 on the proximal portion of the device, the purpose of which is to provide a surface against which a pushing element can eject the device (in its linearized configuration) from the working channel of an endoscope. This description of FIG. 44 in the preceding paragraphs is also generally applicable to FIGS. 48, 51, 52 and 53, which provides an embodiment of the device that differs only in that the flow reduction element 200 is a single large expandable segment rather than being segmented.

FIG. 45A provides a detail view of a proximal portion 20P of a device, and its tapered end portion 700 (internal dotted line with terminal arrows), which begins at a transition point 701. The position of the transition point may vary according to the design choices of a particular design. The transition point may be more proximal or distal from the locations illustrated in the exemplary embodiments. The device terminates generally with a coiled end feature 61 and a terminal bulbous feature 711. Also visible is a layer of Hytrel 705 which covers the entirety of the Nitinol spine of the device. FIG. 45B is the detail view of FIG. 45A straightened to show the detail of the diameter transition regions and the bulbous end.

Figure 46A:
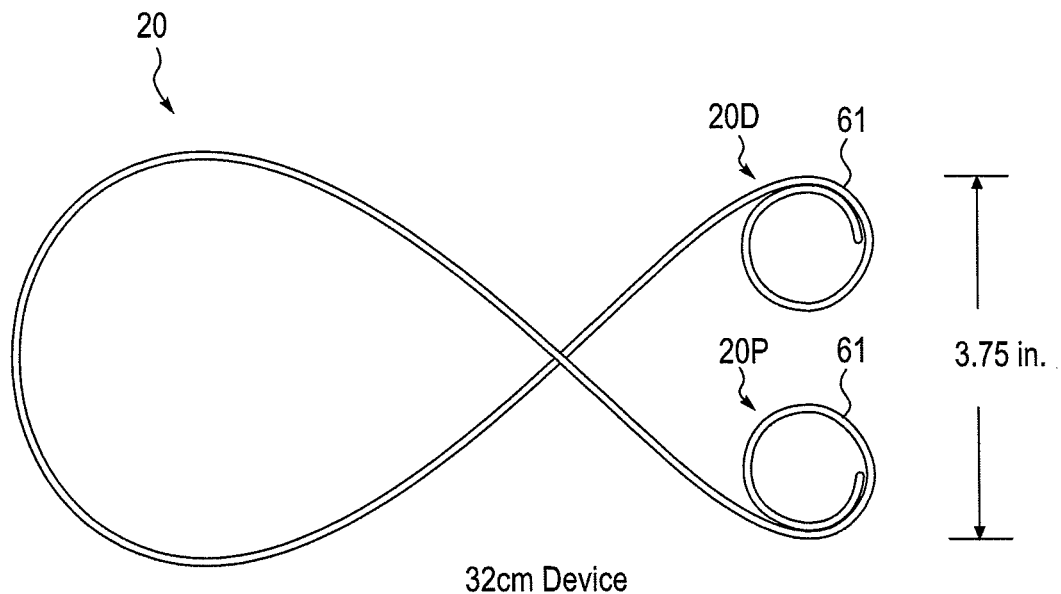
FIGS. 46A and 46B show two devices with a varying amount of end-end crossover.
Figure 46B:
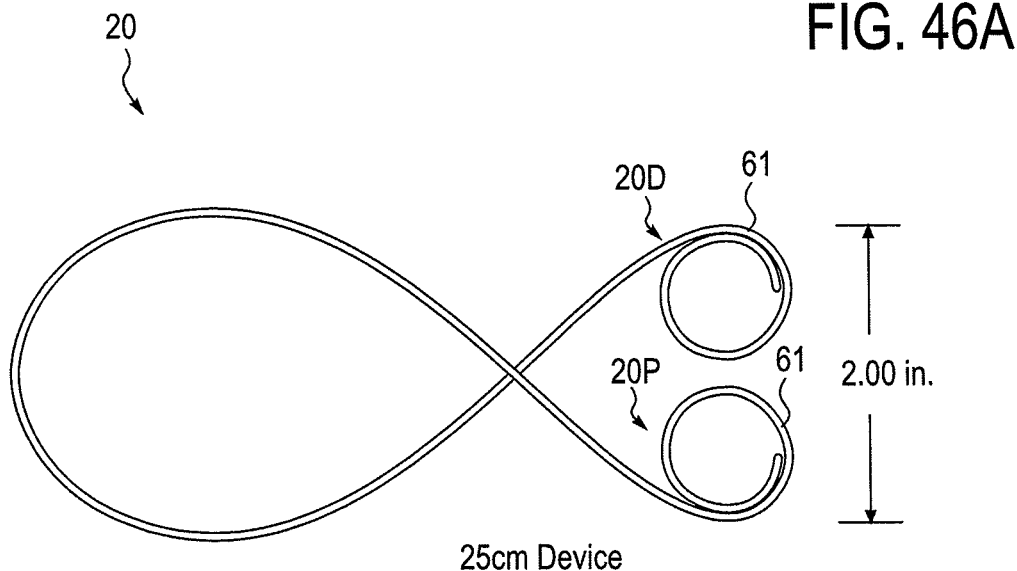

FIGS. 46A and 46B show two devices with a varying amount of end-end crossover; these devices are schematic representations, not drawn to scale in order to emphasize differences in end-end crossover as a function of the length of the device. FIG. 46A depicts a device with a relatively long separation between ends (a 32 cm device) and a relatively large end-end cross over span (3.75 inches). FIG. 46B depicts a device with a relatively short separation between ends (a 25 cm device) and a relatively small end-end cross over span (2 inches). As described above, it is desirable that the end portions of the device exert approximately the same amount of end-end appositionally-directed force, regardless of the length of the lever arm that the distance from the center of the device to the ends represents. Thus, the longer device (FIG. 46A) has a greater degree of crossover, the greater degree of crossover compensating for the greater length of the lever arm. These end-end crossover spans were determined empirically in a test where devices that varied only their length were strained to create a separation force of about 0.04 pounds.

Figure 47:
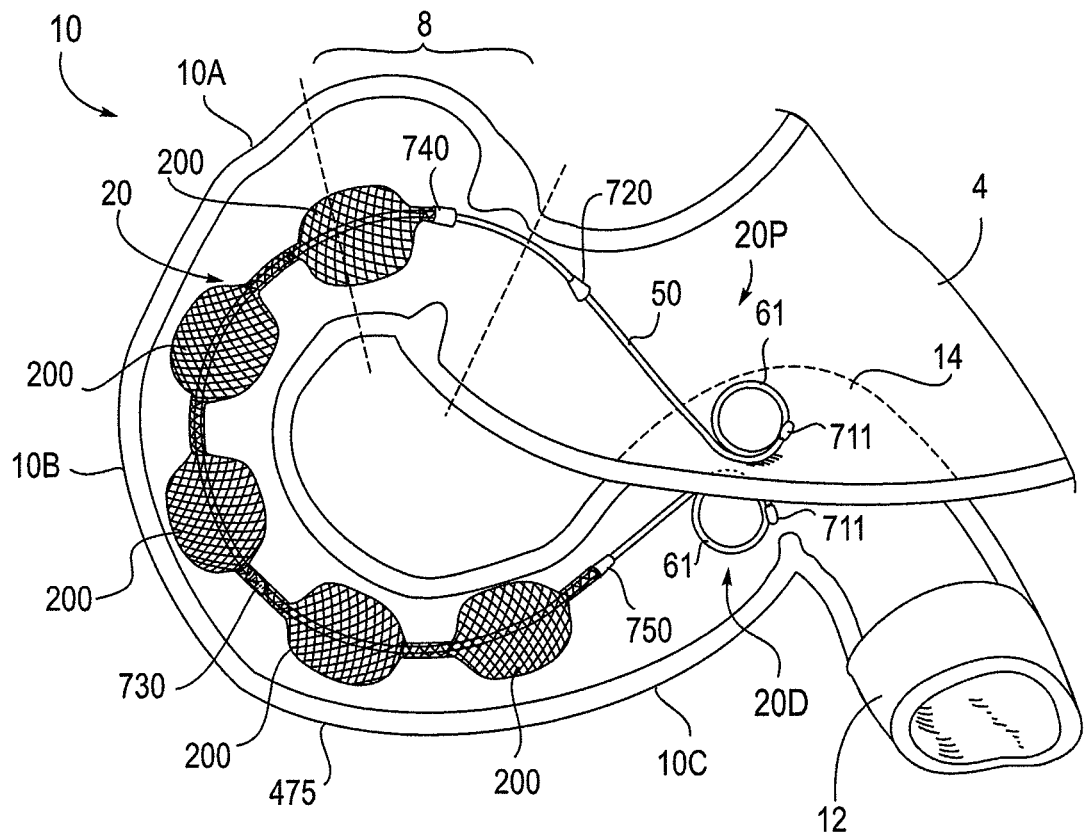
FIG. 47 shows the device depicted in FIG. 44 in a gastrointestinal residence site, with the proximal portion terminating in the gastric antrum, and the distal portion terminating near the duodenojejunal junction.

FIG. 47 shows the device 20 depicted in FIG. 44 in a gastrointestinal residence site, with the proximal portion 20P of the device terminating in the gastric antrum, and the distal portion 20D terminating near the duodenojejunal junction or the duodenojejunal flexure 14. It can be seen that the portion of device 20 that transits through the pylorus 8 is a bare portion of the device, without the flow reduction element 20. The dimension of the spine 50 alone is sufficiently small that the pylorus does not feel its presence, an advantageous feature as described above.

Figure 48:
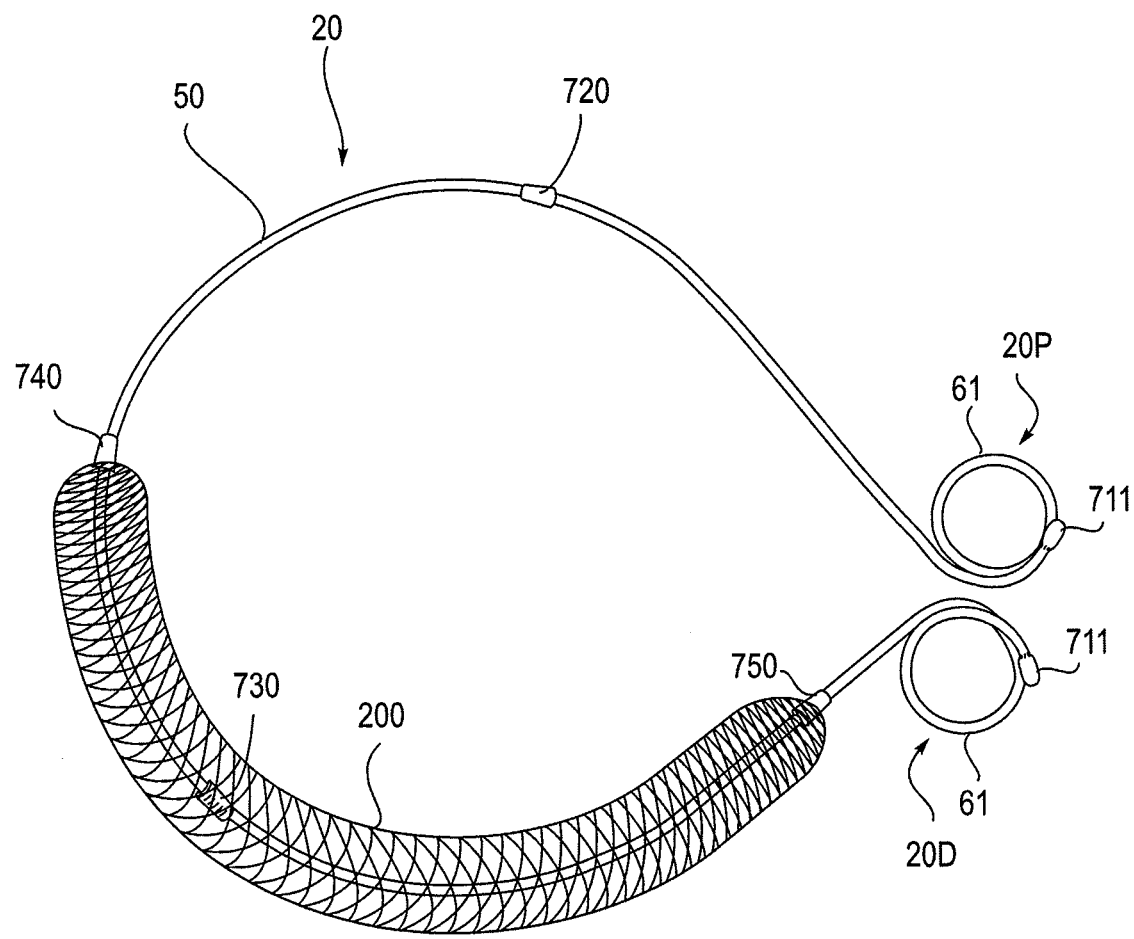
FIG. 48 shows an alternative embodiment of a device similar to that shown in FIG. 44, with a large single flow reduction element.

FIG. 48 shows an alternative embodiment of a device 20 similar to that shown in FIG. 44, with a large single flow reduction element. Other features of the device are substantially the same as those described above with reference to FIG. 44. This embodiment may have therapeutic advantages for some particular applications of the device.

FIGS. 49A-49D show alternative atraumatic end features 710 of an embodiment of a device such as that shown in FIG. 44. FIG. 49A shows an end piece 710 on a distal or proximal portion 20P, 20D of a device that is formed from shape memory material that radially expands in a lantern like fashion when released from linear constraint. The terminal feature has a blunt aspect 711. FIG. 49B shows an end view of the end piece 710 of FIG. 49A, with the radially expanded arms expanding outward from the spine 50 of the device. FIG. 49C shows an end piece 710 in the form of an expandable braided sphere with a blunt distal end 711. FIG. 49D shows an end piece in the form of an expandable braided sphere 710 with an invaginated distal sphere end and a blunted terminal feature 711. All these variants of atraumatic end features 710 are designed to distribute force and prevent abrasion or injury that could arise from the end of a device engaging the surface of gastrointestinal wall.

Figure 50B:
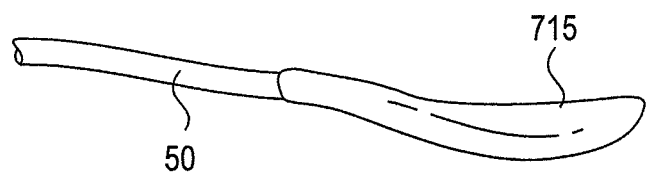
Figure 50C:
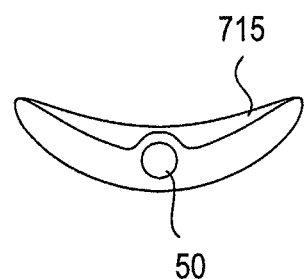
Figure 50D:
Figure 51:
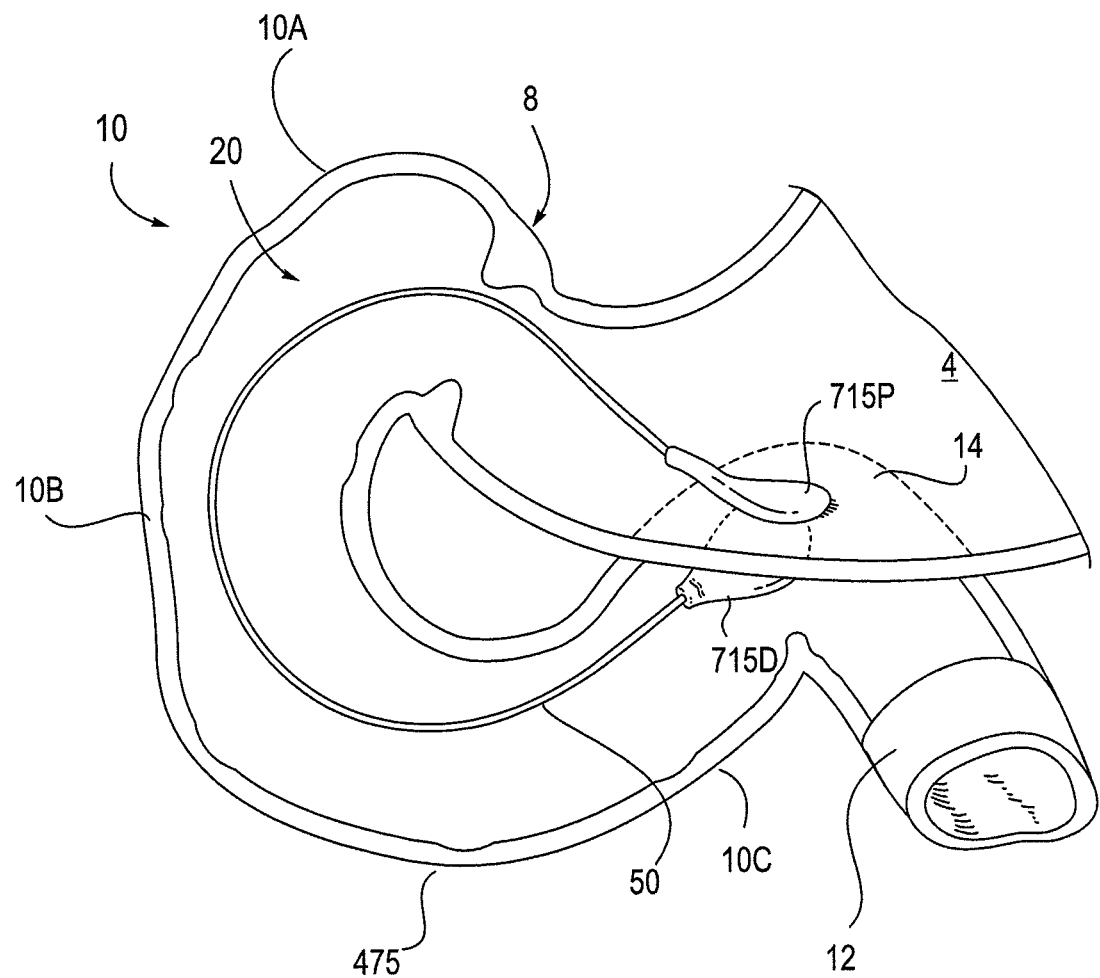
FIG. 51 shows a conformationally-stabilizing device such as depicted in FIG. 50A-50E, the device situated in a gastrointestinal tract residence site, with the proximal end and spoon-shaped end feature pressed against the wall of the gastric antrum, and the spoon-shaped end feature of the distal end pressed against the wall near the duodenojejunal junction.

FIGS. 50A-50D shows spoon or paddle shaped atraumatic end features 715 of a conformationally-stabilizing device, mounted on an end of a spine 50 of the device. FIG. 50A shows a top view of the spoon-shaped feature 715. FIG. 50B shows a side view. FIG. 50C shows an end view of feature 715, depicting a curvature that reflects a rollable bias. FIG. 50D shows an end view of the spoon feature 715 rolled into a stowable configuration for inclusion in an endoscope working channel or delivery sheath. This form of atraumatic feature differs from others generally in that it has a particularly expansive surface that is advantageous in distributing force that may applied against a gastrointestinal wall. By virtue of properties of a shape-memory superelastic alloy such as Nitinol, the feature can be rolled for inclusion within the constraints of the working channel of an endoscope or a delivery sheath, and then automatically unroll upon being released from constraint for deployment in a residence site. In broad form, these spoon- or paddle shaped features 715 are very similar in form and function to the force distribution features 210 shown in FIG. 31.

FIG. 51 shows a conformationally-stabilizing device 20 such as that depicted in FIGS. 50A-50D except that it is depicted only as a bare spine 50, without flow a reducing element. The device is situated in a gastrointestinal tract residence site, with the proximal end of the device 20P and spoon-shaped end feature 715P pressed against the wall of the gastric antrum, and the spoon-shaped end feature of the distal end 715D of the device pressed against the wall near the duodenojejunal junction or the duodenojejunal flexure 14. Apparent in this figure is the very close proximity these two anatomical sites are, in spite of the curvilinear distance separating them within the gastrointestinal tract. It can also be seen that the spoon-shaped end features 715 align flatly against the gastrointestinal wall at both sites, ensuring that the engagement between the device end and the wall surface is without traumatic effect.

Figure 52:
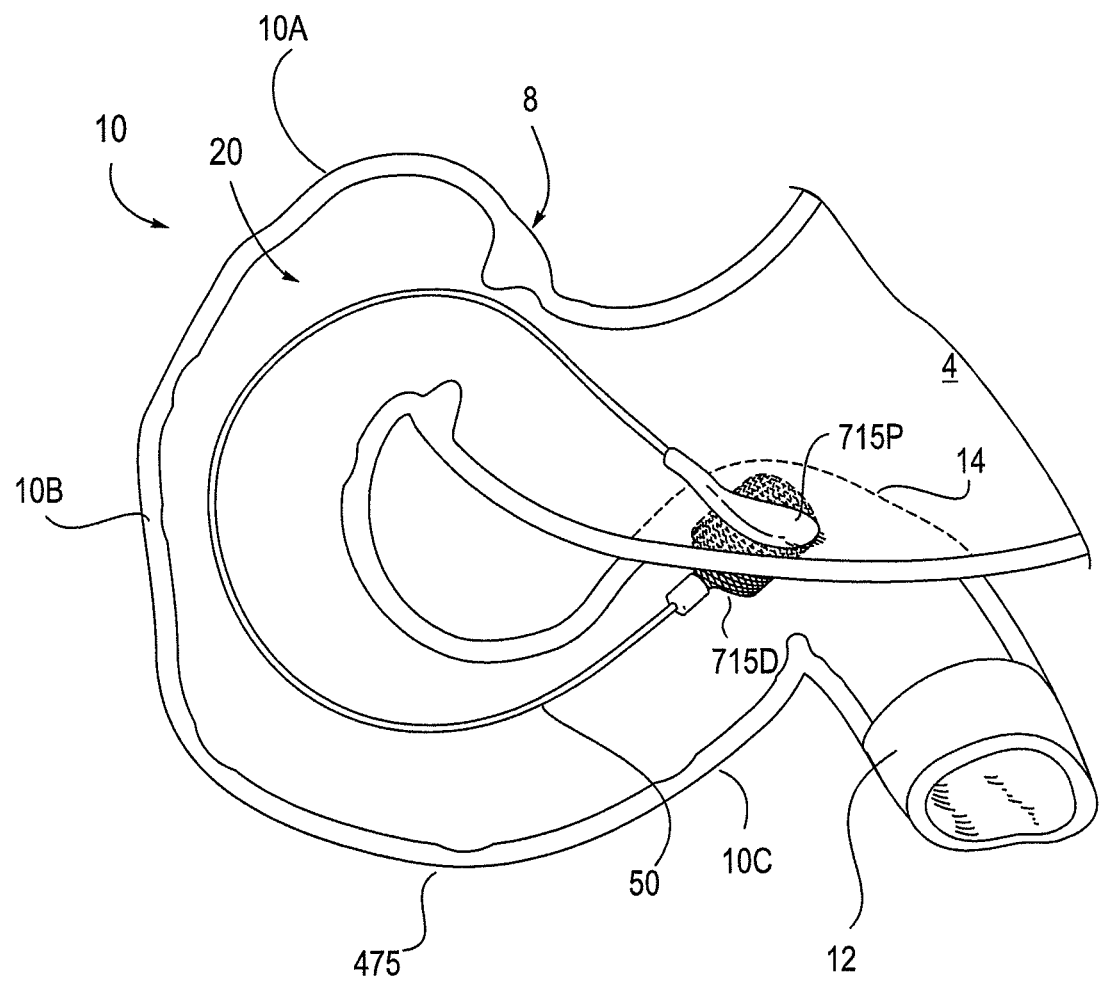
FIG. 52 shows a conformationally-stabilizing device such as depicted in FIG. 51, the device situated in a gastrointestinal tract residence site, with the proximal end and spoon-shaped end feature pressed against the wall of the gastric antrum, as in FIG. 51, and a bulb shaped end feature of the distal end as in FIG. 49C or 49D pressed against the wall near the duodenojejunal junction in a complementary position relative to the proximal end feature.

FIG. 52 shows a conformationally-stabilizing device 20 such as that depicted in FIG. 51 except that it is depicted only as a bare spine 50, without flow-reducing element(s). The device is situated in a gastrointestinal tract residence site, with the proximal end of the device 20P and spoon-shaped end feature 715P pressed against the wall of the gastric antrum, and the basket feature (see FIG. 49C or 49D) of the distal end 20D of the device 715D pressed against the wall near the duodenojejunal junction or the duodenojejunal flexure 14. Apparent in this figure is the very close proximity these two anatomical sites are, in spite of the curvilinear distance separating them within the gastrointestinal tract. In one aspect, the basket on the distal end may be deformed by the force applied by the proximal end feature into a shape complementary to the proximal end feature. In another aspect, the spoon-shaped end feature 715P and the basket 715D may align flatly against the gastrointestinal wall at both sites, ensuring that the engagement between the device end and the wall surface is without traumatic effect.

Figure 53:
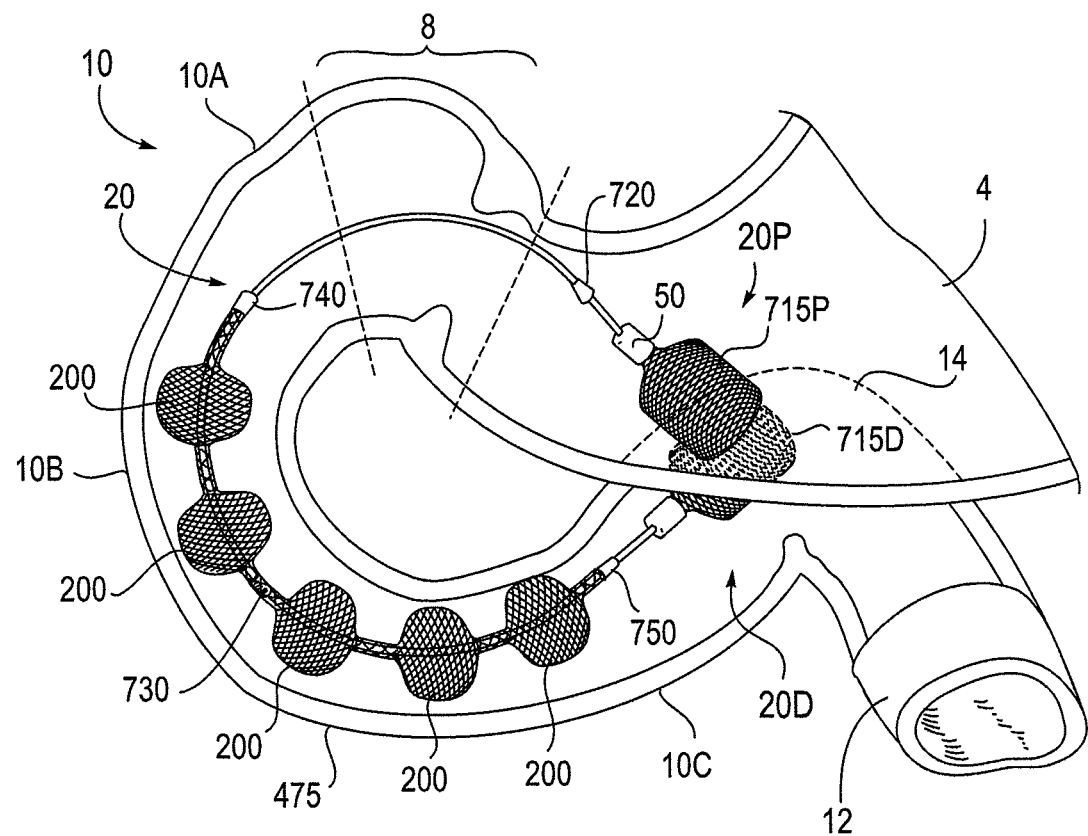
FIG. 53 shows a device similar to that depicted in FIG. 47 in a gastrointestinal residence site, with the proximal portion terminating in the gastric antrum and the distal portion terminating near the duodenojejunal junction with an atraumatic features as in FIG. 49C or 49D an in complementary relation to the proximal end feature.

FIG. 53 is a device configured similar to that of FIG. 47. In the device of FIG. 53, the proximal and distal ends comprise the mesh or braid baskets of FIGS. 49C and 49D. As before, the device 20 is in a gastrointestinal residence site, with the proximal portion 20P of the device terminating in the gastric antrum, and the distal portion 20D terminating near the duodenojejunal junction or the duodenojejunal flexure 14. It can be seen that the portion of device 20 that transits through the pylorus 8 is a bare portion of the device, without the flow reduction element 20. The dimension of the spine 50 alone is sufficiently small that the pylorus does not feel its presence, an advantageous feature as described above. One advantage of the basket structures on both proximal and distal ends is the ability of the ends to deform into complementary shapes in order to provide greater stability and resistance to migration.

In some embodiments of the inventive device, one or more flow reduction elements may be positioned on the device so that when implanted the flow reduction element is within a specific portion of the anatomy or within a position where the flow element with produce a desired result. Possible locations for one or more flow reduction elements include: (a) within the duodenal bulb; (b) within the proximal duodenum; (c) distal to the duodenal bulb; (d) distal to the duodenal bulb and within the vertical duodenum; (e) within 5 cm of the pylorus; (f) one or more positions within the duodenum selected to increase the probability of rector activation in the duodenum (for specific location examples see Ritter article mentioned above and specifically incorporated by reference).

Numerous alternative embodiments of the atraumatic ends are described herein. It is to be appreciated that numerous and various combinations of features and the orientation between them is possible. For example, a convex surface on a proximal feature may, in use, be directed towards a convex surface on a distal feature. Alternatively, a convex surface on a proximal feature may, in use, be directed towards a concave surface on a distal feature. In still another alternative, one atraumatic feature may have a fixed shape while the other feature may have a deformable shape (see FIG. 52). In still other alternatives, both the proximal feature and the distal feature may include deformable shapes (See FIG. 53). The various atraumatic features described herein may be used in any combination. Moreover, the general construction, size, shape and dimension of the proximal and the distal atraumatic features may be converted to structures that may be inflated with gas, liquid or gel.

In one aspect of the present invention, the proximal and distal ends of the device are in close proximity once the device is implanted into a residence site. In one aspect, the proximal end is within 1 cm to 7 cm the distal end. In another aspect, the proximal end is within 1 cm to 3 cm of the distal end. In still another aspect, the proximal end is within 1 cm to 5 cm of the distal end. In still another aspect, the proximal and distal ends be separated by 1 cm or less or may even urge the adjacent tissue into contact. However, in these embodiments, the contact will urge tissue movement and may produce contact between the stomach and the duodenum but without providing sufficient pressure against the involved tissue to form a pressure necrosis or cause erosion or damage to the involved tissue.

Terms and Conventions

Unless defined otherwise, all technical terms used herein have the same meanings as commonly understood by one of ordinary skill in the art of gastrointestinal interventional technologies. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A duodenal device comprising:
   an elongate body having a proximal end, a distal end and a central longitudinal axis extending from the proximal end to the distal end, wherein the central longitudinal axis has a pre-set curvature prior to insertion in a gastrointestinal tract that mimics a transition from a duodenal bulb to a vertical duodenum and a transition from the vertical duodenum to a horizontal duodenum, wherein the central longitudinal axis is configured to return to the pre-set curvature after insertion into the gastrointestinal tract to provide conformational stability for the elongate body; and
   at least one flow reduction element positioned on the elongate body along the central longitudinal axis.

2. The duodenal device of claim 1 wherein at least the distal end is sized for atraumatic passage through a pylorus.

3. The duodenal device of claim 1 wherein the device is configured to remain in position within the gastrointestinal tract without connecting to a wall of the gastrointestinal tract.

4. The device of claim 1 further comprising: an atraumatic feature on the proximal end or the distal end.

5. The device of claim 1 wherein the elongate body comprises a tapered end portion near the proximal end or the distal end.

6. The device of claim 1 wherein the elongate body comprises a shape memory material.

7. The device of claim 6 wherein the shape memory material is Nitinol.

8. The device of claim 1 wherein the elongate body is formed from a single piece of shape memory material.

9. The device of claim 1 further comprising: a coating around the elongate body.

10. The device of claim 9 wherein the coating is a polymer.

11. The device of claim 1 wherein the at least one flow reduction element comprises a braided structure.

12. The device of claim 11 wherein the braided structure ranges from 8 picks per inch to 16 picks per inch.

13. The device of claim 11 wherein the braided structure comprises polymer filaments.

14. The device of claim 11 wherein a portion of the braided structure is secured to the elongate body and a portion of the braided structure is freely slideable relative to the elongate body.

15. The device of claim 14 wherein the braided structure assumes a preformed shape when the portion of the braided structure that is freely slideable moves towards the portion of the braided structure that is secured to the elongate body.

16. The device of claim 15 wherein the preformed shape comprises a plurality of flow reduction forms.

17. The device of claim 1 wherein the at least one flow reduction element is arranged around the elongate body.

18. The device of claim 1 wherein the at least one flow reduction element includes one or more radially expandable segments.

19. The device of claim 1 wherein a portion of the at least one flow reduction element is attached to the elongate body.

20. The device of claim 19 wherein a portion of the at least one flow reduction element is freely slideable over the elongate body.

21. The device of claim 20 further comprising: a stopping feature on the elongate body adapted to prevent movement of the freely slideable portion of the at least one flow reduction element.

22. The device of claim 21 wherein the stopping feature is positioned on the elongate body proximal to the portion of the at least one flow reduction element that is attached to the elongate body.

23. The device of claim 1 further comprising: a feature on the elongate body distal to the proximal end configured to engage a deployment device.

24. The device of claim 1, wherein the length of the elongate body is such that, in use in the gastrointestinal tract, the proximal end is within the stomach and the distal end is adjacent to a duodenojejunal junction.

25. A method of providing therapy in a gastrointestinal tract comprising:
straightening a central longitudinal axis of a device from a pre-set curvature, the device including a proximal end, a distal end, the central longitudinal axis extending from the proximal end to the distal end, and a flow reduction element positioned on the elongate body along the central longitudinal axis, wherein the pre-set curvature mimics a transition from a duodenal bulb to a vertical duodenum and a transition from the vertical duodenum to a horizontal duodenum;
after straightening the central longitudinal axis, positioning the distal end of the device into a first portion of a gastrointestinal tract residence site;
conforming a central portion of the device to a second portion of the gastrointestinal tract residence site by returning the central longitudinal axis to the pre-set curvature to provide conformational stability for the elongate body; and
positioning the proximal end of the device into a third portion of the gastrointestinal tract residence site.

26. The method of claim 25 the positioning the distal end of the device step further comprising: deploying an atraumatic feature into contact with the first portion of a gastrointestinal tract residence site.

27. The method of claim 26 wherein after performing the deploying step the proximal end of the device is separated from the atraumatic feature by a portion of the stomach wall and a portion of duodenal wall.

28. The method of claim 25 the positioning the proximal end of the device step further comprising: deploying an atraumatic feature into contact with the third portion of a gastrointestinal tract residence site.

29. The method of claim 28 wherein after the deploying step the atraumatic feature is in contact with the stomach wall in the antrum.

30. The method of claim 28 wherein after performing the deploying step the distal end of the device is separated from the atraumatic feature by a portion of the stomach wall and a portion of duodenal wall.

31. The method of claim 25 wherein the first portion of a gastrointestinal tract residence site is distal to the vertical duodenum.

32. The method of claim 25 wherein the first portion of a gastrointestinal tract residence site is within the horizontal duodenum.

33. The method of claim 25 wherein the first portion of a gastrointestinal tract residence site is within or distal to the horizontal duodenum and adjacent to the third portion of the gastrointestinal tract residence site.

34. The method of claim 25 wherein the first portion of a gastrointestinal tract residence site is within or near the duodenojejunal flexure.

35. The method of claim 25 wherein the first portion of a gastrointestinal tract residence site is within or near the portion of the duodenum adjacent to the Ligament of Treitz.

36. The method of claim 25 wherein the third portion of a gastrointestinal tract residence site is proximal to the pylorus.

37. The method of claim 25 wherein the third portion of a gastrointestinal tract residence site is within the antrum of the stomach.

38. The method of claim 25 further comprising: maintaining the position of the device within the gastrointestinal residence site without impairing pyloric function or gastric emptying.

39. The method of claim 25 further comprising: maintaining the position of the device within the gastrointestinal residence site while atraumatically withstanding peristaltic action.

40. The method of claim 25 wherein after performing the positioning and conforming steps the proximal end of the device is separated from the distal end of the device by a portion of the stomach wall and a portion of duodenal wall.

41. The method of claim 25 the conforming step further comprising: moving the device relative to the gastrointestinal tract residence site to assume a portion of a preformed device shape.

42. The method of claim 25 the conforming step further comprising: moving the device relative to the gastrointestinal tract residence site to obtain a preselected alignment of the proximal end and the distal end of the device.

43. The method of claim 41 or 42 wherein the force to accomplish the moving step is provided by a shape memory component of the device.

44. The method of claim 25 further comprising:
providing therapy from the device.

45. The method of claim 44 the providing therapy step further comprising:
deploying at least one flow reduction element from the device to reduce the flow of chyme past the device.

46. The method of claim 44 the providing therapy step further comprising:
providing electrical stimulation from the device to a portion of the gastrointestinal tract residence site.

47. The method of claim 46 wherein the electrical stimulation produces a sensation of satiety in the patient.

48. The method of claim 44 the providing therapy step further comprising:
providing mechanical stimulation from the device to a portion of the gastrointestinal tract residence site.

49. The method of claim 48 wherein the mechanical stimulation produces a sensation of satiety in the patient.

50. The method of claim 44 the providing therapy step further comprising:
providing a bioactive agent from the device to a portion of the gastrointestinal tract residence site.

51. The method of claim 50 wherein providing a bioactive agent produces a sensation of satiety in the patient.

52. The method of claim 44 wherein the providing therapy step is selected to cause loss of excess weight in a patient.

53. The method of claim 44 the providing therapy step further comprising:
positioning the device to provide slowing of chyme flow through the duodenum.

* * * * *